United States Patent [19]
Tuomanen et al.

[11] Patent Number: 6,015,560
[45] Date of Patent: Jan. 18, 2000

[54] ANTIBODY RECOGNIZING ENDOTHELIAL CELL LIGAND FOR LEUKOCYTE CR3

[75] Inventors: Elaine Tuomanen; H. Robert Masure, both of New York, N.Y.

[73] Assignee: The Rockfeller University, New York, N.Y.

[21] Appl. No.: 08/465,966

[22] Filed: Jun. 6, 1995

Related U.S. Application Data

[60] Division of application No. 08/348,353, Nov. 30, 1994, which is a continuation-in-part of application No. 08/247,572, May 23, 1994, abandoned, which is a continuation of application No. PCT/US92/03725, May 4, 1992, which is a continuation-in-part of application No. 07/695,613, May 3, 1991, abandoned.

[51] Int. Cl.[7] .................................................... A61K 39/40
[52] U.S. Cl. ..................................... 424/150.1; 424/130.1; 424/136.1; 424/141.1; 424/143.1; 424/234.1; 424/240.1
[58] Field of Search ............................ 424/130.1, 136.1, 424/141.1, 143.1, 234.1, 240.1

[56] References Cited

PUBLICATIONS

Fox et al *J Gen. Virol* Mar. 1989 70(Pt 3) pp. 625–637 (Abstract Only).
Smith et al *JBC* Jul. 25, 1990 265(21) pp. 12267–12271 (Abstract Only).
Appel et al *J of Immunology* 144(3) pp. 976–983.
Sato et al. Infection and Immunity Oct. 1990 pp. 3369–3374 vol. 58 No. 10.
Graf et al. Biochemistry 1987, 26, 6896–6900.
Muller et al. (1992) J. Exp. Med. 176:819–28.
Miletich et al. (1978) J. Biol. Chem. 253:6908–16.
Fung et al. (1985) Proc. Natl. Acad. Sci. USA 82:3591–5.
Quagliarello et al. (1992) N. Engl. J. Med. 327:864–72.
Tuomanen et al. (1985) J. Infec. Dis 151:859–68.
Tuomanen et al. (1989) J. Exp. Med. 170:959–68.
Wright et al. (1992) J. Exp. Med. 156:1149–64.
Tuomanen et al. (1985) J. Infec. Dis. 152:118–25.
Relman et al. (1990) Cell 61:1375–82.
Tuomanen et al. (1988) J. Exp. Med. 168:267–77.
Relman et al. (1989) Proc. Natl. Acad. Sci. USA 86:2637–41.
Domenighini et al. (1990) Molec. Micro. 4:787–800.
Delisse–Gathotye et al. (1990) Infrect. Immun. 58:2895–905.
Altieri et al. (1992) Science 254:1200–2.
Tuomanen et al. (1985) J. Infect. Dis. 155:985–90.
Kadurugamuwa (1987) Program and Abstracts of the 27th ICAA Meeting, p. 205.
McAllister et al. (1975) J. Infec. Dis. 132:355–60.
Tam et al. (1988) J. Am. Chem Soc. 105:6455–61.
Saukkonen et al. (1991) J. Exp. Med. 173:1143–9.
Rosenberg et al. (1987) Gene 56:125–35.
Tabor et al. (1985) Proc. Natl. Acad. Sci. USA 84:4767–71.
Muller et al. (1989) J. Exp. Med. 170:399–414.
Lo et al. (1991) J. Exp. Med. 173:1493–500.

*Primary Examiner*—Nita Minnifield
*Attorney, Agent, or Firm*—Klauber & Jackson

[57] ABSTRACT

Peptides which will inhibit the reaction between the RGD tripeptide of FHA and the integrin receptors of endothelial cells and their utility as therapeutic agents are described.

14 Claims, 42 Drawing Sheets

FIG. 1

**Regions of FNA which mimic human proteins that bind CR3;
mapping relative to the carbohydrate recognition domain**

```
             Region
RGD
1097-9    A      B    C D
   ↓    ┌────┬──────┬─┬──┐
*───────│....│//////│ │::│
        └────┴──────┴─┴──┘
Amino Acid
 Residue
        1141 1279  2012 2110
```

A= CRD
B= C3bi ligand
RGD= endothelial cell ligand
*= Factor Ten ligands
  *residues    32-36
               1979-1984
               2062-2068
               2523-2533

FIG. 3

Oligopeptides of the FHA carbohydrate Binding region (1141-1279)

LEHSTIESKISQSVLAAKGDKGKPAVSVKVAKKLFLNGTLRAVNDNNETMSGRQIDVVDGRPQITDAVTGEARKD...

I (1141-1185)

II (1171-1215)

III

...ESVVSDAALVADGGPIVVEAGELVSHAGGIGNGRNKENGASVTVRTTGNLVNKGYISAGKQGVLE

III (1200-1245)

IV (1231-1280)

```
GGA TCC ACG GTG GCG GCG AAC TCG CTG CAC GCC                          2869
Gly Ser Thr Val Ala Ala Asn Ser Leu His Ala
 1                   5                      10

AAT CGC GAC GTT CGG GTC AGC GGC AAG GAT GCG GTG CGC GTA ACG GCC      2917
Asn Arg Asp Val Arg Val Ser Gly Lys Asp Ala Val Arg Val Thr Ala
         15                      20                      25

GCC ACC AGC GGG GGT CTG CAT GTG TCG AGC GGC CGC CAG CTC GAT          2965
Ala Thr Ser Gly Gly Leu His Val Ser Ser Gly Arg Gln Leu Asp
         30                      35                  40

CTG GGC GCC GTG CAG GCG CGC GGC GCG CTG GCC CTG GAC GGA GGC GCC      3013
Leu Gly Ala Val Gln Ala Arg Gly Ala Leu Ala Leu Asp Gly Gly Ala
     45                      50                      55

GGC GTG GCG CTG CAA TCG GCC AAG GCT AGC GGC ACG CTG CAT GTG CAG      3061
Gly Val Ala Leu Gln Ser Ala Lys Ala Ser Gly Thr Leu His Val Gln
             60                      65                      70                  75

GGC GAG CAC CTG GAC CTG GGC ACG TTG GCC GCC GTA GGG GCG GTG          3109
Gly Glu His Leu Asp Leu Gly Thr Leu Ala Ala Val Gly Ala Val
             80                      85                  90

GAC GTC AAT GGC ACG GGA GAC GTG CGC GTT GCG AAG CTG GTG AGC GAT      3157
Asp Val Asn Gly Thr Gly Asp Val Arg Val Ala Lys Leu Val Ser Asp
     95                      100                     105
```

Figure 10A

```
GCA GGC GCC GAT CTG CAA GCG GGG CGC TCC ATG ACG CTG GGT ATC GTC    3205
Ala Gly Ala Asp Leu Gln Ala Gly Arg Ser Met Thr Leu Gly Ile Val
            110                     115                     120

GAC ACG GGC ACC GAT CTG CAG GCG CGC GCG CAG CAG AAG CTG GAG CTC    3253
Asp Thr Gly Thr Asp Leu Gln Ala Arg Ala Gln Gln Lys Leu Glu Leu
            125                     130                     135

GGG TCG GTT AAG AGC GAT GGC GGC CTT CAG GCG CTG GCA GCC GGG GCC    3301
Gly Ser Val Lys Ser Asp Gly Gly Leu Gln Ala Leu Ala Ala Gly Ala
            140                     145                     150                 155

CTC AGC CTG GCG GCG GCA GAA GTC GCA GGG GCG CTG GAG CTC TCG GGC    3349
Leu Ser Leu Ala Ala Ala Glu Val Ala Gly Ala Leu Glu Leu Ser Gly
            160                     165                                 170

CAG GGC GTC ACC GTG GAC AGA GCC AGC GCT AGC CGG GCA CGC ATC GAC    3397
Gln Gly Val Thr Val Asp Arg Ala Ser Ala Ser Arg Ala Arg Ile Asp
            175                     180                     185

AGC ACC GGT TCG GTC GGC ATC GGC GCG CTG AAG GCA GGC GCT GTC GAG    3445
Ser Thr Gly Ser Val Gly Ile Gly Ala Leu Lys Ala Gly Ala Val Glu
            190                     195                     200

GCC GCC TCG CCA CGG CGG CGG GCG CGC CGC GCG CTG CGG CAG GAT TTC TTC    3493
Ala Ala Ser Pro Arg Arg Arg Ala Arg Arg Ala Leu Arg Gln Asp Phe Phe
            205                     210                     215
```

Figure 10B

```
ACG CCC GGC AGC GTG GTC CGC GCC CAG GGC AAT GTC ACG GTC GGG    3541
Thr Pro Gly Ser Val Val Val Arg Ala Gln Gly Asn Val Thr Val Gly
220                 225                 230                 235

CGC GGC GAT CCG CAT CAG GGC GTG CTG GCC CAG GGC GAC ATC ATC ATG    3589
Arg Gly Asp Pro His Gln Gly Val Leu Ala Gln Gly Asp Ile Ile Met
        240                 245                 250

GAT GCG AAG GGC ACC TTG CGC AAC GAT GCC TTG ACC GAG    3637
Asp Ala Lys Gly Thr Leu Arg Asn Asp Ala Leu Thr Glu
    255                 260                 265

AAC GGG ACG GTC ACC ATA TCG GCC GAT TCG GCC GTG CTG CTC GAG CAT TCC    3685
Asn Gly Thr Val Thr Ile Ser Ala Asp Ser Ala Val Leu Glu His Ser
270                 275                 280

ACC ATC GAG AGC AAG ATC AGC CAG AGC GTG CTG GCT GCC AAA GGG GAC    3733
Thr Ile Glu Ser Lys Ile Ser Gln Ser Val Leu Ala Ala Lys Gly Asp
    285                 290                 295

AAG GGC AAG CCG GCG GTG TCG GTG AAG GTC GCG AAG AAG CTG TTT CTC    3781
Lys Gly Lys Pro Ala Val Ser Val Lys Val Ala Lys Lys Leu Phe Leu
300                 305                 310                 315

AAT GGT ACG TTG CGG GCC GTC AAC GAC AAC GAA ACC ATG TCC GGG    3829
Asn Gly Thr Leu Arg Ala Val Asn Asp Asn Glu Thr Met Ser Gly
        320                 325                 330
```

Figure 10C

CGC CAG ATC GAC GTC GTG GAC GGA CGT CCG CAG ATC ACC GAC GCG GTC   3877
Arg Gln Ile Asp Val Val Asp Gly Arg Pro Gln Ile Thr Asp Ala Val
                335                     340                 345

ACG GGC GAA GCG CGT AAG GAC GAA TCG GTT GTG TCC GAC GCC GCG CTC   3925
Thr Gly Glu Ala Arg Lys Asp Glu Ser Val Val Ser Asp Ala Ala Leu
                350                     355                 360

GTG GCC GAT GGC GGT CCG ATC GTG GTC GAG GCC GGC CTG GTC AGC       3973
Val Ala Asp Gly Gly Pro Ile Val Val Glu Ala Gly Glu Leu Val Ser
                365                     370             375

CAT GCC GGC GGT ATC GGC AAC GGC CGC AAC AAG GAG AAT GGC GCC AGC   4021
His Ala Gly Gly Ile Gly Asn Gly Arg Asn Lys Glu Asn Gly Ala Ser
        380                     385                     390     395

GTC ACC GTG CGC ACG ACT GGC ACC AAC CTG GTC AAC AAG GGC TAC ATC TCG   4069
Val Thr Val Arg Thr Thr Gly Thr Asn Leu Val Asn Lys Gly Tyr Ile Ser
                    400                         405                 410

GCC GGC AAG CAG GGC GTG CTC GAG GTG GGC GCC TTG ACG AAC GAG       4117
Ala Gly Lys Gln Gly Val Leu Glu Val Gly Gly Ala Leu Thr Asn Glu
            415                     420                 425

TTC CTG GTC GGC TCG GAC GGC ACC CAG GCG CAG CGC ATC GAG GCG CAG CGC ATC   4165
Phe Leu Val Gly Ser Asp Gly Thr Gln Ala Gln Arg Ile Glu Ala Gln Arg Ile
                430                     435                 440

Figure 10D

```
GAG AAC AGG GGC ACC TTC CAG AGC CAG GCT CCG GCG GGC ACG GCC GGC         4213
Glu Asn Arg Gly Thr Phe Gln Ser Gln Ala Pro Ala Gly Thr Ala Gly
445                 450                 455

GCC CTG GTC AAG GCT GCC GAG GCC ATC GTG CAC GAC GGC GTC ATG             4261
Ala Leu Val Lys Ala Ala Glu Ala Ile Val His Asp Gly Val Met
460                 465                 470                 475

GCC ACC AAA GGC GAG ATG CAG ATC GCC GGC AAG GGC GGG TCT CCG             4309
Ala Thr Lys Gly Glu Met Gln Ile Ala Gly Lys Gly Gly Ser Pro
        480                 485                 490

ACC GTC ACC GCC GGC GCA AAG GCG ACG ACC AGC GCG AAC AAG CTG AGC         4357
Thr Val Thr Ala Gly Ala Lys Ala Thr Thr Ser Ala Asn Lys Leu Ser
        495                 500                 505

GTC GAC GTG GCA AGC TGG GAC AAC GCG GGA AGC CTG GAT ATC AAG AAG         4405
Val Asp Val Ala Ser Trp Asp Asn Ala Gly Ser Leu Asp Ile Lys Lys
510                 515                 520

GGC GGC GCG CAG GTC ACG GTC GCC GGG CGC TAT GCC GAG CAC GGC GAG         4453
Gly Gly Ala Gln Val Thr Val Ala Gly Arg Tyr Ala Glu His Gly Glu
525                 530                 535

GTT TCG ATA CAG GGC GAT TAC ACC GTC TCG GCC GAC GCC ATC GCG CTG         4501
Val Ser Ile Gln Gly Asp Tyr Thr Val Ser Ala Asp Ala Ile Ala Leu
540                 545                 550                 555
```

Figure 10E

```
GCG GCG CAG GTC ACC CAG CGC GGA GGC GCC GCG AAC CTG ACC TCG CGG    4549
Ala Ala Gln Val Thr Gln Arg Gly Gly Ala Ala Asn Leu Thr Ser Arg
            560                 565                 570

CAC GAC ACC CGT TTC TCC AAC AAG ATT CGC CTG ATG GGG CCG TTG CAG    4597
His Asp Thr Arg Phe Ser Asn Lys Ile Arg Leu Met Gly Pro Leu Gln
            575                 580                 585

GTC AAC GCC GGG GGC GGG CCG GTG TCC AAT ACC GGC AAT CTG AAA GTG CGC    4645
Val Asn Ala Gly Gly Gly Pro Val Ser Asn Thr Gly Asn Leu Lys Val Arg
            590                 595                 600

GAG GGC GTG ACC GTA ACG GCG TCG TTC GAC AAC GAG ACC GGG GCC    4693
Glu Gly Val Thr Val Thr Ala Ala Ser Phe Asp Asn Glu Thr Gly Ala
            605                 610                 615

GAG GTC ATG GCC AAG AGC GCC ACG CTG ACG ACT TCC GGG GCC CGC    4741
Glu Val Met Ala Lys Ser Ala Thr Leu Thr Thr Ser Gly Ala Ala Arg
            620                 625                 630                 635

AAC GCG GGC AAG ATG CAG GTC AAG GAG GCC ACG ATC GTT GCC GCC    4789
Asn Ala Gly Lys Met Gln Val Lys Glu Ala Thr Ile Val Ala Ala
            640                 645                 650

AGC GTT TCC AAT CCC GGC ACG TTC ACG GCC AAG GAT ATC ACT GTT    4837
Ser Val Ser Asn Pro Gly Thr Phe Thr Ala Gly Lys Asp Ile Thr Val
            655                 660                 665
```

Figure 10F

```
ACC TCG CGC GGA GGA TTC GAT AAC GAA GGC AAG ATG GAG TCC AAC AAG        4885
Thr Ser Arg Gly Gly Phe Asp Asn Glu Gly Lys Met Glu Ser Asn Lys
        670                 675                 680

GAC ATC GTC ATC AAG ACG GAA CAG TTC AGC AAT GGC AGG GTT CTC GAC        4933
Asp Ile Val Ile Lys Thr Glu Gln Phe Ser Asn Gly Arg Val Leu Asp
        685                 690                 695

GCC AAG CAT GAT CTG ACG GTC ACG GCG AGC GGG CAG GCG GAC AAC CGG        4981
Ala Lys His Asp Leu Thr Val Thr Ala Ser Gly Gln Ala Asp Asn Arg
        700                 705                 710                 715

GGC AGC CTG AAG GCA GGC CAC GAT TTC ACG GTG CAG GCC CAG CGT ATC        5029
Gly Ser Leu Lys Ala Gly His Asp Phe Thr Val Gln Ala Gln Arg Ile
        720                 725                 730

GAC AAT AGC GGA ACC ATG GCC GCC GGC CAC GAC GCC ACG CTG AAG GCG        5077
Asp Asn Ser Gly Thr Met Ala Ala Gly His Asp Ala Thr Leu Lys Ala
        735                 740                 745

CCG CAC CTG CGC AAT ACG GGC CAG GTC GTA GCC GGG CAC GAC ATC CAT        5125
Pro His Leu Arg Asn Thr Gly Gln Val Val Ala Gly His Asp Ile His
        750                 755                 760

ATC ATC AAC AGC GCC AAG CTG GAG AAC ACC GGG CGC GTG GAT GCG CGC        5173
Ile Ile Asn Ser Ala Lys Leu Glu Asn Thr Gly Arg Val Asp Ala Arg
        765                 770                 775
```

Figure 10G

```
AAC GAC ATC GCT CTG GAT GTG GCG GAT TTC ACC AAC ACG GGA TCC CTC    5221
Asn Asp Ile Ala Leu Asp Val Ala Asp Phe Thr Asn Thr Gly Ser Leu
780                 785                 790                 795

TAC GCC GAG CAT GAC GCG ACG CTG ACG CTT GCG CAA GGC ACG CAG CGC    5269
Tyr Ala Glu His Asp Ala Thr Leu Thr Leu Ala Gln Gly Thr Gln Arg
        800                 805                 810

GAT CTG GTG GAC CAG GAT CAT ATC CTG CCG GTG GCA GAG GGG ACG        5317
Asp Leu Val Val Asp Gln Asp His Ile Leu Pro Val Ala Glu Gly Thr
    815                 820                 825

TTA CGC GTC AAG GCC AAG TCG CTG ACC ACC GAA ATC CTG ACC GGC AAT    5365
Leu Arg Val Lys Ala Lys Ser Leu Thr Thr Glu Ile Leu Thr Gly Asn
830                 835                 840

CCC GGC AGC CTG ATC GCC GAG GTG CAG GAA AAT ATC GAC AAC AAG CAG    5413
Pro Gly Ser Leu Ile Ala Glu Val Gln Glu Asn Ile Asp Asn Lys Gln
845                 850                 855

GCC ATC GTC GGC AAG GAC CTG ACG AGT TCG GCG CAC GGC AAC            5461
Ala Ile Val Val Gly Lys Asp Leu Thr Ser Ser Ala His Gly Asn
860                 865                 870                 875

GTG GCC AAC GAA GCG AAC GCG CTG CTG TGG GCC GCC GGG GAG CTG ACC    5509
Val Ala Asn Glu Ala Asn Ala Leu Leu Trp Ala Ala Gly Glu Leu Thr
        880                 885                 890
```

Figure 10H

```
GTC AAG GCG CAG AAC ATC ACC AAT AAA CGG GCC GCG CTG ATC GAG GCG        5557
Val Lys Ala Gln Asn Ile Thr Asn Lys Arg Ala Ala Leu Ile Glu Ala
            895                 900                 905

GGC AAC GCC CGG CTG ACG GCG GCC GTT GCC TTG CTC AAC AAG CTG            5605
Gly Asn Ala Arg Leu Thr Ala Ala Val Ala Leu Leu Asn Lys Leu
        910                 915                 920
```

Figure 10D

```
GGC CGC ATT CGC GCG GGC GAG GAC ATG CAC CTG GAT GCG CCG CGC ATC        5653
Gly Arg Ile Arg Ala Gly Glu Asp Met His Leu Asp Ala Pro Arg Ile
            925                 930                 935

GAG AAC ACC GCG AAA CTG AGC GGC GAG GTG CAA CGC AAA GGC GTG CAG        5701
Glu Asn Thr Ala Lys Leu Ser Gly Glu Val Gln Arg Lys Gly Val Gln
            940                 945                 950                 955

GAC GTC GGG GGA GGC GAG CAC GGC CGC TGG AGC GGT ATC GGC TAT GTC        5749
Asp Val Gly Gly Gly Glu His Gly Arg Trp Ser Gly Ile Gly Tyr Val
            960                 965                 970

AAC TAC TGG TTG CGC GCC GGC AAT GGG AAG AAG GCG GGA ACC ATC GCC        5797
Asn Tyr Trp Leu Arg Ala Gly Asn Gly Lys Lys Ala Gly Thr Ile Ala
        975                 980                 985

GCG CCG TGG TAT GGC GGT GAT CTG ACG GCG GAG CAG TCG CTC ATC GAG        5845
Ala Pro Trp Tyr Gly Gly Asp Leu Thr Ala Glu Gln Ser Leu Ile Glu
        990                 995                 1000
```

Figure 10 I

```
GTC GGC AAG GAT CTC TAT CTG AAT GCC GGA GCG CGC AAG GAC GAA CAT    5893
Val Gly Lys Asp Leu Tyr Leu Asn Ala Gly Ala Arg Lys Asp Glu His
1005                          1010                    1015

CGC CAT CTG CTC AAT GAA GGC GTG ATC CAG GCG GGC GGC CAT GGC CAC    5941
Arg His Leu Leu Asn Glu Gly Val Ile Gln Ala Gly Gly His Gly His
1020                          1025                    1030     1035

ATC GGC GGC GAC GTG GAC AAC CGG TCG GTG GTG CGC ACC GTG TCC GCC    5989
Ile Gly Gly Asp Val Asp Asn Arg Ser Val Val Arg Thr Val Ser Ala
1040                          1045                    1050

ATG GAG TAT TTC AAG ACG CCT CTT CCG GTG AGC CTG ACT GCC CTG GAC    6037
Met Glu Tyr Phe Lys Thr Pro Leu Pro Val Ser Leu Thr Ala Leu Asp
1055                          1060                    1065

AAT CGT GCC GGC TTG TCT CCG GCG ACC TGG AAC TTC CAG TCC ACG TAT    6085
Asn Arg Ala Gly Leu Ser Pro Ala Thr Trp Asn Phe Gln Ser Thr Tyr
1070                          1075                    1080

GAA CTC CTG GAT TAT CTG CTG GAC CAG AAT CGC TAC GAG TAC ATT TGG    6133
Glu Leu Leu Asp Tyr Leu Leu Asp Gln Asn Arg Tyr Glu Tyr Ile Trp
1085                          1090                    1095

GGG CTG TAT CCG ACC TAC ACC GAA TGG TCG GTG AAT ACG CTG AAG AAC    6181
Gly Leu Tyr Pro Thr Tyr Thr Glu Trp Ser Val Asn Thr Leu Lys Asn
1100                          1105                    1110     1115
```

Figure 10J

```
CTC GAC CTG GGC TAC CAG GCC AAG CCG GCT CCC ACT GCG CCG CCG ATG      6229
Leu Asp Leu Gly Tyr Gln Ala Lys Pro Ala Pro Thr Ala Pro Pro Met
                1120                    1125                1130

CCC AAG GCT CCC GAA CTC GAC CTG CGT GGC CAT ACG CTG GAG TCG GCC      6277
Pro Lys Ala Pro Glu Leu Asp Leu Arg Gly His Thr Leu Glu Ser Ala
                1135                    1140                1145

GAA GGC CGG AAG ATC TTT GGC GAG TAC AAG AAG CTG CAA GGC GAG TAC      6325
Glu Gly Arg Lys Ile Phe Gly Glu Tyr Lys Lys Leu Gln Gly Glu Tyr
        1150                    1155                    1160

GAG AAG GCG AAG ATG GCC GTC CAG GCC GTG GAG GCT TAC GGC GAG GCT      6373
Glu Lys Ala Lys Met Ala Val Gln Ala Val Glu Ala Tyr Gly Glu Ala
        1165                    1170                    1175

ACT CGG CGC GTC CAT GAT CAG CTG GGC CAA CGT TAT GGT AAG GCC CTG      6421
Thr Arg Arg Val His Asp Gln Leu Gly Gln Arg Tyr Gly Lys Ala Leu
        1180                    1185                    1190       1195

GGC GGC ATG GAT GCC GAG ACC AAG GAG GTC GAC GGC ATC ATC CAG GAG      6469
Gly Gly Met Asp Ala Glu Thr Lys Glu Val Asp Gly Ile Ile Gln Glu
                1200                    1205                1210

TTC GCC GCG GAT CTG CGA ACG GTC TAT GCC AAG CAG GAC GCC GAC GCG      6517
Phe Ala Ala Asp Leu Arg Thr Val Tyr Ala Lys Gln Ala Asp Gln Ala
                1215                    1220                1225
```

Figure 10K

```
ACC ATC GAC GCA GAG ACG GAC AAG GTC GCC CAG CGC TAC AAG TCG CAG    6565
Thr Ile Asp Ala Glu Thr Asp Lys Val Ala Gln Arg Tyr Lys Ser Gln
        1230                    1235                    1240

ATC GAC GCG GTG CGG                                                6580
Ile Asp Ala Val Arg
        1245
```

Figure 10L

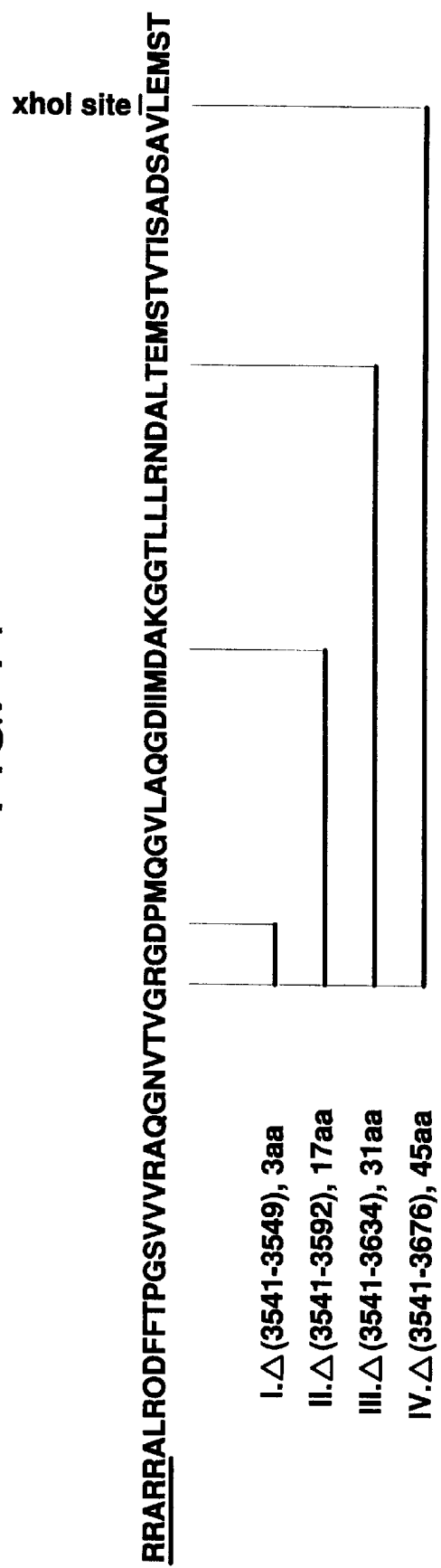

FIG. 24

FHA A  1055 IGALKAGAVEAASPRRAARRALRQDFFTPGSVVVRAQGNYTVGRGD 1099

FHA B  1076 RQDFFTPGS VVVRAQGNVTVG RGDPHQGVLAQGDIIMDAKGGTLL 1120

FHA C  1097 RGDPHQGVLAQGDIIMDAKGGTLLLRNDALTENGTVTTISADSAVL 1141

FHA C a  1097 RGDPHQGVLAQGDIIMDAKG 1116

FHA C b  RADPHQGVLAQGDIIMDAKG

FHA C c  AADPHQGVLAQGDIIMDAKG

FHA Cd  1117 GTLLLRNDALTENGTVTISA 1136

SEQUENCE LISTING (1) GENERAL INFORMATION:

(iii) NUMBER OF SEQUENCES: 38

(2) INFORMATION FOR SEQ ID NO:1:

(i) SEQUENCE CHARACTERISTICS:
    (A) LENGTH: 9 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:1:

Gly Tyr Asp Thr Lys Gln Glu Asp Gly
 1               5

(2) INFORMATION FOR SEQ ID NO:2:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Ile Asp Arg Ser Met Lys Thr Arg Gly
 1               5

(2) INFORMATION FOR SEQ ID NO:3:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Gly Leu Tyr Gln Ala Lys Arg Phe Lys Val Gly
 1               5                  10

(2) INFORMATION FOR SEQ ID NO:4:

(i) SEQUENCE CHARACTERISTICS:
        (A) LENGTH: 45 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Ile Gly Ala Leu Lys Ala Gly Ala Val Glu Ala Ala Ser Pro Arg Arg
 1               5                  10                  15

Ala Arg Arg Ala Leu Arg Gln Asp Phe Phe Thr Pro Gly Ser Val Val
                20                  25                  30

Val Arg Ala Gln Gly Asn Val Thr Val Gly Arg Gly Asp
                35                  40                  45

(2) INFORMATION FOR SEQ ID NO:5:

(i) SEQUENCE CHARACTERISTICS:
        (A) LENGTH: 45 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Arg Gln Asp Phe Phe Thr Pro Gly Ser Val Val Arg Ala Gln Gly
 1               5                  10                  15

Asn Val Thr Val Gly Arg Gly Asp Pro Met Gln Gly Val Leu Ala Gln
                20                  25                  30

Gly Asp Ile Ile Met Asp Ala Lys Gly Gly Thr Leu Leu
                35                  40                  45
```

(2) INFORMATION FOR SEQ ID NO:6:

(i) SEQUENCE CHARACTERISTICS:
        (A) LENGTH: 45 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Arg Gly Asp Pro Met Gln Gly Val Leu Ala Gln Gly Asp Ile Ile Met
 1               5                  10                  15

Asp Ala Lys Gly Gly Thr Leu Leu Leu Arg Asn Asp Ala Leu Thr Glu
                20                  25                  30

Met Gly Thr Val Thr Ile Ser Ala Asp Ser Ala Val Leu
                35                  40                  45
```

(2) INFORMATION FOR SEQ ID NO:7:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Glu Thr Lys Glu Val Asp Gly
 1               5
```

(2) INFORMATION FOR SEQ ID NO:8:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
Gly Arg Thr Arg Gly
 1               5
```

(2) INFORMATION FOR SEQ ID NO:9:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

```
Gly Leu Ile Gln Gly Arg Ser Val Lys Val Asp
 1               5                  10
```

(2) INFORMATION FOR SEQ ID NO:10:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

```
Leu Gly Tyr Gln Ala Lys
 1               5
```

(2) INFORMATION FOR SEQ ID NO:11:

(i) SEQUENCE CHARACTERISTICS:
        (A) LENGTH: 45 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

```
Leu Glu His Ser Thr Ile Glu Ser Lys Ile Ser Gln Ser Val Leu Ala
 1               5                  10                  15

Ala Lys Gly Asp Lys Gly Lys Pro Ala Val Ser Val Lys Val Ala Lys
                20                  25                  30

Lys Leu Phe Leu Asn Gly Thr Leu Arg Ala Val Asn Asp
                35                  40                  45
```

(2) INFORMATION FOR SEQ ID NO:12:

(i) SEQUENCE CHARACTERISTICS:
        (A) LENGTH: 45 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

```
Ala Lys Lys Leu Phe Leu Asn Gly Thr Leu Arg Ala Val Asn Asp Asn
 1               5                  10                  15

Asn Glu Thr Met Ser Gly Arg Gln Ile Asp Val Val Asp Gly Arg Pro
                20                  25                  30

Gln Ile Thr Asp Ala Val Thr Gly Glu Ala Arg Lys Asp
                35                  40                  45
```

(2) INFORMATION FOR SEQ ID NO:13:

(i) SEQUENCE CHARACTERISTICS:
        (A) LENGTH: 46 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

```
Gly Arg Pro Gln Ile Thr Asp Ala Val Thr Gly Glu Ala Arg Lys Asp
 1               5                  10                  15

Glu Ser Val Val Ser Asp Ala Ala Leu Val Ala Asp Gly Gly Pro Ile
                20                  25                  30

Val Val Glu Ala Gly Glu Leu Val Ser His Ala Gly Gly Ile
```

(2) INFORMATION FOR SEQ ID NO:14:

(i) SEQUENCE CHARACTERISTICS:
        (A) LENGTH: 50 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

```
Ile Val Val Glu Ala Gly Glu Leu Val Ser His Ala Gly Gly Ile Gly
 1               5                  10                  15

Asn Gly Arg Asn Lys Glu Asn Gly Ala Ser Val Thr Val Arg Thr Thr
            20                  25                  30

Gly Asn Leu Val Asn Lys Gly Tyr Ile Ser Ala Gly Lys Gln Gly Val
        35                  40                  45

Leu Glu
    50
```

(2) INFORMATION FOR SEQ ID NO:15:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

```
Thr Val Gly Arg Gly Asp Pro His Gln
 1               5
```

(2) INFORMATION FOR SEQ ID NO:16:

(i) SEQUENCE CHARACTERISTICS:
        (A) LENGTH: 3744 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..3744

(x) PUBLICATION INFORMATION:
        (A) AUTHORS: Delisse-Gathoye, et al.
        (B) TITLE: Cloning, Partial Sequence, Expressions, and
            Antigenic Analysis of the Filamentous
            Hemagglutinin Gene of Bordatella Pertussis
        (C) JOURNAL: Infection and Immunity
        (D) VOLUME: 58
        (E) ISSUE: 9
        (F) PAGES: 2895-2905
        (G) DATE: September-1990

(xi) SEQUENCE DESCRIPTION: SEQ ID NO:16:

```
GGA TCC ACG GTG GCG GCG AAC TCG CTG CAC GCC AAT CGC GAC GTT CGG    48
Gly Ser Thr Val Ala Ala Asn Ser Leu His Ala Asn Arg Asp Val Arg
 1               5                  10                  15

GTC AGC GGC AAG GAT GCG GTG CGC GTA ACG GCC GCC ACC AGC GGG GGC    96
Val Ser Gly Lys Asp Ala Val Arg Val Thr Ala Ala Thr Ser Gly Gly
            20                  25                  30

GGT CTG CAT GTG TCG AGC GGC CGC CAG CTC GAT CTG GGC GCC GTG CAG   144
Gly Leu His Val Ser Ser Gly Arg Gln Leu Asp Leu Gly Ala Val Gln
        35                  40                  45
```

-continued

| | |
|---|---|
| GCG CGC GGC GCG CTG GCC CTG GAC GGA GGC GCC GGC GTG GCG CTG CAA<br>Ala Arg Gly Ala Leu Ala Leu Asp Gly Gly Ala Gly Val Ala Leu Gln<br>50                        55                      60 | 192 |
| TCG GCC AAG GCT AGC GGC ACG CTG CAT GTG CAG GGC GGC GAG CAC CTG<br>Ser Ala Lys Ala Ser Gly Thr Leu His Val Gln Gly Gly Glu His Leu<br>65                        70                      75                      80 | 240 |
| GAC CTG GGC ACG TTG GCC GCC GTA GGG GCG GTG GAC GTC AAT GGC ACG<br>Asp Leu Gly Thr Leu Ala Ala Val Gly Ala Val Asp Val Asn Gly Thr<br>                      85                      90                      95 | 288 |
| GGA GAC GTG CGC GTT GCG AAG CTG GTG AGC GAT GCA GGC GCC GAT CTG<br>Gly Asp Val Arg Val Ala Lys Leu Val Ser Asp Ala Gly Ala Asp Leu<br>                100                    105                    110 | 336 |
| CAA GCG GGG CGC TCC ATG ACG CTG GGT ATC GTC GAC ACG ACC GGC GAT<br>Gln Ala Gly Arg Ser Met Thr Leu Gly Ile Val Asp Thr Thr Gly Asp<br>              115                    120                    125 | 384 |
| CTG CAG GCG CGC GCG CAG CAG AAG CTG GAG CTC GGG TCG GTT AAG AGC<br>Leu Gln Ala Arg Ala Gln Gln Lys Leu Glu Leu Gly Ser Val Lys Ser<br>130                        135                      140 | 432 |
| GAT GGC GGC CTT CAG GCG GCC GCC GGC GGG GCC CTC AGC CTG GCG GCG<br>Asp Gly Gly Leu Gln Ala Ala Ala Gly Gly Ala Leu Ser Leu Ala Ala<br>145                        150                    155                    160 | 480 |
| GCG GAA GTC GCA GGG GCG CTG GAG CTC TCG GGC CAG GGC GTC ACC GTG<br>Ala Glu Val Ala Gly Ala Leu Glu Leu Ser Gly Gln Gly Val Thr Val<br>              165                    170                    175 | 528 |
| GAC AGA GCC AGC GCT AGC CGG GCA CGC ATC GAC AGC ACC GGT TCG GTC<br>Asp Arg Ala Ser Ala Ser Arg Ala Arg Ile Asp Ser Thr Gly Ser Val<br>              180                    185                    190 | 576 |
| GGC ATC GGC GCG CTG AAG GCA GGC GCT GTC GAG GCC GCC TCG CCA CGG<br>Gly Ile Gly Ala Leu Lys Ala Gly Ala Val Glu Ala Ala Ser Pro Arg<br>              195                    200                    205 | 624 |
| CGG GCG CGC CGC GCG CTG CGG CAG GAT TTC TTC ACG CCC GGC AGC GTG<br>Arg Ala Arg Arg Ala Leu Arg Gln Asp Phe Phe Thr Pro Gly Ser Val<br>210                        215                      220 | 672 |
| GTG GTC CGC GCC CAG GGC AAT GTC ACG GTC GGG CGC GGC GAT CCG CAT<br>Val Val Arg Ala Gln Gly Asn Val Thr Val Gly Arg Gly Asp Pro His<br>225                        230                    235                    240 | 720 |
| CAG GGC GTG CTG GCC CAG GGC GAC ATC ATC ATG GAT GCG AAG GGC GGC<br>Gln Gly Val Leu Ala Gln Gly Asp Ile Ile Met Asp Ala Lys Gly Gly<br>              245                    250                    255 | 768 |
| ACC TTG CTG TTG CGC AAC GAT GCC TTG ACC GAG AAC GGG ACG GTC ACC<br>Thr Leu Leu Leu Arg Asn Asp Ala Leu Thr Glu Asn Gly Thr Val Thr<br>              260                    265                    270 | 816 |
| ATA TCG GCC GAT TCG GCC GTG CTC GAG CAT TCC ACC ATC GAG AGC AAG<br>Ile Ser Ala Asp Ser Ala Val Leu Glu His Ser Thr Ile Glu Ser Lys<br>              275                    280                    285 | 864 |
| ATC AGC CAG AGC GTG CTG GCT GCC AAA GGG GAC AAG GGC AAG CCG GCG<br>Ile Ser Gln Ser Val Leu Ala Ala Lys Gly Asp Lys Gly Lys Pro Ala<br>290                        295                    300 | 912 |
| GTG TCG GTG AAG GTC GCG AAG AAG CTG TTT CTC AAT GGT ACG TTG CGG<br>Val Ser Val Lys Val Ala Lys Lys Leu Phe Leu Asn Gly Thr Leu Arg<br>305                        310                    315                    320 | 960 |
| GCC GTC AAC GAC AAC AAC GAA ACC ATG TCC GGG CGC CAG ATC GAC GTC<br>Ala Val Asn Asp Asn Asn Glu Thr Met Ser Gly Arg Gln Ile Asp Val<br>              325                    330                    335 | 1008 |
| GTG GAC GGA CGT CCG CAG ATC ACC GAC GCG GTC ACG GGC GAA GCG CGT<br>Val Asp Gly Arg Pro Gln Ile Thr Asp Ala Val Thr Gly Glu Ala Arg<br>              340                    345                    350 | 1056 |
| AAG GAC GAA TCG GTT GTG TCC GAC GCC GCG CTC GTG GCC GAT GGC GGT<br>Lys Asp Glu Ser Val Val Ser Asp Ala Ala Leu Val Ala Asp Gly Gly<br>355                        360                    365 | 1104 |

```
CCG ATC GTG GTC GAG GCC GGC GAG CTG GTC AGC CAT GCC GGC GGT ATC      1152
Pro Ile Val Val Glu Ala Gly Glu Leu Val Ser His Ala Gly Gly Ile
    370                 375                 380

GGC AAC GGC CGC AAC AAG GAG AAT GGC GCC AGC GTC ACC GTG CGC ACG      1200
Gly Asn Gly Arg Asn Lys Glu Asn Gly Ala Ser Val Thr Val Arg Thr
385                 390                 395                 400

ACT GGC AAC CTG GTC AAC AAG GGC TAC ATC TCG GCC GGC AAG CAG GGC      1248
Thr Gly Asn Leu Val Asn Lys Gly Tyr Ile Ser Ala Gly Lys Gln Gly
                405                 410                 415

GTG CTC GAG GTG GGC GGC GCC TTG ACG AAC GAG TTC CTG GTC GGC TCG      1296
Val Leu Glu Val Gly Gly Ala Leu Thr Asn Glu Phe Leu Val Gly Ser
            420                 425                 430

GAC GGC ACC CAG CGC ATC GAG GCG CAG CGC ATC GAG AAC AGG GGC ACC      1344
Asp Gly Thr Gln Arg Ile Glu Ala Gln Arg Ile Glu Asn Arg Gly Thr
        435                 440                 445

TTC CAG AGC CAG GCT CCG GCG GGC ACG GCC GGC GCC CTG GTG GTC AAG      1392
Phe Gln Ser Gln Ala Pro Ala Gly Thr Ala Gly Ala Leu Val Val Lys
    450                 455                 460

GCT GCC GAG GCC ATC GTG CAC GAC GGC GTC ATG GCC ACC AAA GGC GAG      1440
Ala Ala Glu Ala Ile Val His Asp Gly Val Met Ala Thr Lys Gly Glu
465                 470                 475                 480

ATG CAG ATC GCC GGC AAG GGC GGC GGG TCT CCG ACC GTC ACC GCC GGC      1488
Met Gln Ile Ala Gly Lys Gly Gly Gly Ser Pro Thr Val Thr Ala Gly
                485                 490                 495

GCA AAG GCG ACG ACC AGC GCG AAC AAG CTG AGC GTC GAC GTG GCA AGC      1536
Ala Lys Ala Thr Thr Ser Ala Asn Lys Leu Ser Val Asp Val Ala Ser
            500                 505                 510

TGG GAC AAC GCG GGA AGC CTG GAT ATC AAG AAG GGC GGC GCG CAG GTC      1584
Trp Asp Asn Ala Gly Ser Leu Asp Ile Lys Lys Gly Gly Ala Gln Val
        515                 520                 525

ACG GTG GCC GGG CGC TAT GCC GAG CAC GGC GAG GTT TCG ATA CAG GGC      1632
Thr Val Ala Gly Arg Tyr Ala Glu His Gly Glu Val Ser Ile Gln Gly
    530                 535                 540

GAT TAC ACC GTC TCG GCC GAC GCC ATC GCG CTG GCG GCG CAG GTC ACC      1680
Asp Tyr Thr Val Ser Ala Asp Ala Ile Ala Leu Ala Ala Gln Val Thr
545                 550                 555                 560

CAG CGC GGA GGC GCC GCG AAC CTG ACC TCG CGG CAC GAC ACC CGT TTC      1728
Gln Arg Gly Gly Ala Ala Asn Leu Thr Ser Arg His Asp Thr Arg Phe
                565                 570                 575

TCC AAC AAG ATT CGC CTG ATG GGG CCG TTG CAG GTC AAC GCC GGC GGG      1776
Ser Asn Lys Ile Arg Leu Met Gly Pro Leu Gln Val Asn Ala Gly Gly
            580                 585                 590

CCG GTG TCC AAT ACC GGC AAT CTG AAA GTG CGC GAG GGC GTG ACC GTA      1824
Pro Val Ser Asn Thr Gly Asn Leu Lys Val Arg Glu Gly Val Thr Val
        595                 600                 605

ACG GCG GCG TCG TTC GAC AAC GAG ACC GGG GCC GAG GTC ATG GCC AAG      1872
Thr Ala Ala Ser Phe Asp Asn Glu Thr Gly Ala Glu Val Met Ala Lys
    610                 615                 620

AGC GCC ACG CTG ACG ACT TCC GGG GCC GCG CGC AAC GCG GGC AAG ATG      1920
Ser Ala Thr Leu Thr Thr Ser Gly Ala Ala Arg Asn Ala Gly Lys Met
625                 630                 635                 640

CAG GTC AAG GAG GCC GCC ACG ATC GTT GCC GCC AGC GTT TCC AAT CCC      1968
Gln Val Lys Glu Ala Ala Thr Ile Val Ala Ala Ser Val Ser Asn Pro
                645                 650                 655

GGC ACG TTC ACG GCC GGC AAG GAT ATC ACT GTT ACC TCG CGC GGA GGA      2016
Gly Thr Phe Thr Ala Gly Lys Asp Ile Thr Val Thr Ser Arg Gly Gly
            660                 665                 670

TTC GAT AAC GAA GGC AAG ATG GAG TCC AAC AAG GAC ATC GTC ATC AAG      2064
Phe Asp Asn Glu Gly Lys Met Glu Ser Asn Lys Asp Ile Val Ile Lys
        675                 680                 685
```

```
ACG GAA CAG TTC AGC AAT GGC AGG GTT CTC GAC GCC AAG CAT GAT CTG    2112
Thr Glu Gln Phe Ser Asn Gly Arg Val Leu Asp Ala Lys His Asp Leu
    690                 695                 700

ACG GTC ACG GCG AGC GGG CAG GCG GAC AAC CGG GGC AGC CTG AAG GCA    2160
Thr Val Thr Ala Ser Gly Gln Ala Asp Asn Arg Gly Ser Leu Lys Ala
705                 710                 715                 720

GGC CAC GAT TTC ACG GTG CAG GCC CAG CGT ATC GAC AAT AGC GGA ACC    2208
Gly His Asp Phe Thr Val Gln Ala Gln Arg Ile Asp Asn Ser Gly Thr
                725                 730                 735

ATG GCC GCC GGC CAC GAC GCC ACG CTG AAG GCG CCG CAC CTG CGC AAT    2256
Met Ala Ala Gly His Asp Ala Thr Leu Lys Ala Pro His Leu Arg Asn
            740                 745                 750

ACG GGC CAG GTC GTA GCC GGG CAC GAC ATC CAT ATC ATC AAC AGC GCC    2304
Thr Gly Gln Val Val Ala Gly His Asp Ile His Ile Ile Asn Ser Ala
        755                 760                 765

AAG CTG GAG AAC ACC GGG CGC GTG GAT GCG CGC AAC GAC ATC GCT CTG    2352
Lys Leu Glu Asn Thr Gly Arg Val Asp Ala Arg Asn Asp Ile Ala Leu
    770                 775                 780

GAT GTG GCG GAT TTC ACC AAC ACG GGA TCC CTC TAC GCC GAG CAT GAC    2400
Asp Val Ala Asp Phe Thr Asn Thr Gly Ser Leu Tyr Ala Glu His Asp
785                 790                 795                 800

GCG ACG CTG ACG CTT GCG CAA GGC ACG CAG CGC GAT CTG GTG GTG GAC    2448
Ala Thr Leu Thr Leu Ala Gln Gly Thr Gln Arg Asp Leu Val Val Asp
                805                 810                 815

CAG GAT CAT ATC CTG CCG GTG GCG GAG GGG ACG TTA CGC GTC AAG GCC    2496
Gln Asp His Ile Leu Pro Val Ala Glu Gly Thr Leu Arg Val Lys Ala
            820                 825                 830

AAG TCG CTG ACC ACC GAA ATC GAG ACC GGC AAT CCC GGC AGC CTG ATC    2544
Lys Ser Leu Thr Thr Glu Ile Glu Thr Gly Asn Pro Gly Ser Leu Ile
        835                 840                 845

GCC GAG GTG CAG GAA AAT ATC GAC AAC AAG CAG GCC ATC GTC GTC GGC    2592
Ala Glu Val Gln Glu Asn Ile Asp Asn Lys Gln Ala Ile Val Val Gly
    850                 855                 860

AAG GAC CTG ACG CTG AGT TCG GCG CAC GGC AAC GTG GCC AAC GAA GCG    2640
Lys Asp Leu Thr Leu Ser Ser Ala His Gly Asn Val Ala Asn Glu Ala
865                 870                 875                 880

AAC GCG CTG CTG TGG GCC GCC GGG GAG CTG ACC GTC AAG GCG CAG AAC    2688
Asn Ala Leu Leu Trp Ala Ala Gly Glu Leu Thr Val Lys Ala Gln Asn
                885                 890                 895

ATC ACC AAT AAA CGG GCC GCG CTG ATC GAG GCG GGC GGC AAC GCC CGG    2736
Ile Thr Asn Lys Arg Ala Ala Leu Ile Glu Ala Gly Gly Asn Ala Arg
            900                 905                 910

CTG ACG GCG GCC GTT GCC TTG CTC AAC AAG CTG GGC CGC ATT CGC GCG    2784
Leu Thr Ala Ala Val Ala Leu Leu Asn Lys Leu Gly Arg Ile Arg Ala
        915                 920                 925

GGC GAG GAC ATG CAC CTG GAT GCG CCG CGC ATC GAG AAC ACC GCG AAA    2832
Gly Glu Asp Met His Leu Asp Ala Pro Arg Ile Glu Asn Thr Ala Lys
    930                 935                 940

CTG AGC GGC GAG GTG CAA CGC AAA GGC GTG CAG GAC GTC GGG GGA GGC    2880
Leu Ser Gly Glu Val Gln Arg Lys Gly Val Gln Asp Val Gly Gly Gly
945                 950                 955                 960

GAG CAC GGC CGC TGG AGC GGT ATC GGC TAT GTC AAC TAC TGG TTG CGC    2928
Glu His Gly Arg Trp Ser Gly Ile Gly Tyr Val Asn Tyr Trp Leu Arg
                965                 970                 975

GCC GGC AAT GGG AAG AAG GCG GGA ACC ATC GCC GCG CCG TGG TAT GGC    2976
Ala Gly Asn Gly Lys Lys Ala Gly Thr Ile Ala Ala Pro Trp Tyr Gly
            980                 985                 990

GGT GAT CTG ACG GCG GAG CAG TCG CTC ATC GAG GTC GGC AAG GAT CTC    3024
Gly Asp Leu Thr Ala Glu Gln Ser Leu Ile Glu Val Gly Lys Asp Leu
        995                 1000                1005
```

```
TAT CTG AAT GCC GGA GCG CGC AAG GAC GAA CAT CGC CAT CTG CTC AAT        3072
Tyr Leu Asn Ala Gly Ala Arg Lys Asp Glu His Arg His Leu Leu Asn
        1010                1015                1020

GAA GGC GTG ATC CAG GCG GGC GGC CAT GGC CAC ATC GGC GGC GAC GTG        3120
Glu Gly Val Ile Gln Ala Gly Gly His Gly His Ile Gly Gly Asp Val
1025                1030                1035                1040

GAC AAC CGG TCG GTG GTG CGC ACC GTG TCC GCC ATG GAG TAT TTC AAG        3168
Asp Asn Arg Ser Val Val Arg Thr Val Ser Ala Met Glu Tyr Phe Lys
                1045                1050                1055

ACG CCT CTT CCG GTG AGC CTG ACT GCC CTG GAC AAT CGT GCC GGC TTG        3216
Thr Pro Leu Pro Val Ser Leu Thr Ala Leu Asp Asn Arg Ala Gly Leu
            1060                1065                1070

TCT CCG GCG ACC TGG AAC TTC CAG TCC ACG TAT GAA CTC CTG GAT TAT        3264
Ser Pro Ala Thr Trp Asn Phe Gln Ser Thr Tyr Glu Leu Leu Asp Tyr
        1075                1080                1085

CTG CTG GAC CAG AAT CGC TAC GAG TAC ATT TGG GGG CTG TAT CCG ACC        3312
Leu Leu Asp Gln Asn Arg Tyr Glu Tyr Ile Trp Gly Leu Tyr Pro Thr
    1090                1095                1100

TAC ACC GAA TGG TCG GTG AAT ACG CTG AAG AAC CTC GAC CTG GGC TAC        3360
Tyr Thr Glu Trp Ser Val Asn Thr Leu Lys Asn Leu Asp Leu Gly Tyr
1105                1110                1115                1120

CAG GCC AAG CCG GCT CCC ACT GCG CCG CCG ATG CCC AAG GCT CCC GAA        3408
Gln Ala Lys Pro Ala Pro Thr Ala Pro Pro Met Pro Lys Ala Pro Glu
                1125                1130                1135

CTC GAC CTG CGT GGC CAT ACG CTG GAG TCG GCC GAA GGC CGG AAG ATC        3456
Leu Asp Leu Arg Gly His Thr Leu Glu Ser Ala Glu Gly Arg Lys Ile
            1140                1145                1150

TTT GGC GAG TAC AAG AAG CTG CAA GGC GAG TAC GAG AAG GCG AAG ATG        3504
Phe Gly Glu Tyr Lys Lys Leu Gln Gly Glu Tyr Glu Lys Ala Lys Met
        1155                1160                1165

GCC GTC CAG GCC GTG GAG GCT TAC GGC GAG GCT ACT CGG CGC GTC CAT        3552
Ala Val Gln Ala Val Glu Ala Tyr Gly Glu Ala Thr Arg Arg Val His
    1170                1175                1180

GAT CAG CTG GGC CAA CGT TAT GGT AAG GCC CTG GGC GGC ATG GAT GCC        3600
Asp Gln Leu Gly Gln Arg Tyr Gly Lys Ala Leu Gly Gly Met Asp Ala
1185                1190                1195                1200

GAG ACC AAG GAG GTC GAC GGC ATC ATC CAG GAG TTC GCC GCG GAT CTG        3648
Glu Thr Lys Glu Val Asp Gly Ile Ile Gln Glu Phe Ala Ala Asp Leu
                1205                1210                1215

CGA ACG GTC TAT GCG AAG CAG GCC GAC CAG GCG ACC ATC GAC GCA GAG        3696
Arg Thr Val Tyr Ala Lys Gln Ala Asp Gln Ala Thr Ile Asp Ala Glu
            1220                1225                1230

ACG GAC AAG GTC GCC CAG CGC TAC AAG TCG CAG ATC GAC GCG GTG CGG        3744
Thr Asp Lys Val Ala Gln Arg Tyr Lys Ser Gln Ile Asp Ala Val Arg
        1235                1240                1245
```

(2) INFORMATION FOR SEQ ID NO:17:

(i) SEQUENCE CHARACTERISTICS:
        (A) LENGTH: 1248 amino acids
        (B) TYPE: amino acid
        (D) TOPOLOGY: linear (ii) MOLECULE TYPE: protein (xi) SEQUENCE DESCRIPTION: SEQ ID NO:17:

```
Gly Ser Thr Val Ala Ala Asn Ser Leu His Ala Asn Arg Asp Val Arg
 1               5                  10                  15

Val Ser Gly Lys Asp Ala Val Arg Val Thr Ala Ala Thr Ser Gly Gly
                20                  25                  30

Gly Leu His Val Ser Ser Gly Arg Gln Leu Asp Leu Gly Ala Val Gln
```

-continued

```
                35                  40                  45
Ala Arg Gly Ala Leu Ala Leu Asp Gly Gly Ala Gly Val Ala Leu Gln
    50                  55                  60
Ser Ala Lys Ala Ser Gly Thr Leu His Val Gln Gly Gly Glu His Leu
65                  70                  75                  80
Asp Leu Gly Thr Leu Ala Ala Val Gly Ala Val Asp Val Asn Gly Thr
                85                  90                  95
Gly Asp Val Arg Val Ala Lys Leu Val Ser Asp Ala Gly Ala Asp Leu
            100                 105                 110
Gln Ala Gly Arg Ser Met Thr Leu Gly Ile Val Asp Thr Thr Gly Asp
            115                 120                 125
Leu Gln Ala Arg Ala Gln Gln Lys Leu Glu Leu Gly Ser Val Lys Ser
130                 135                 140
Asp Gly Gly Leu Gln Ala Ala Gly Gly Ala Leu Ser Leu Ala Ala
145                 150                 155                 160
Ala Glu Val Ala Gly Ala Leu Glu Leu Ser Gly Gln Gly Val Thr Val
                165                 170                 175
Asp Arg Ala Ser Ala Ser Arg Ala Arg Ile Asp Ser Thr Gly Ser Val
            180                 185                 190
Gly Ile Gly Ala Leu Lys Ala Gly Ala Val Glu Ala Ala Ser Pro Arg
        195                 200                 205
Arg Ala Arg Ala Leu Arg Gln Asp Phe Phe Thr Pro Gly Ser Val
210                 215                 220
Val Val Arg Ala Gln Gly Asn Val Thr Val Gly Arg Gly Asp Pro His
225                 230                 235                 240
Gln Gly Val Leu Ala Gln Gly Asp Ile Ile Met Asp Ala Lys Gly Gly
                245                 250                 255
Thr Leu Leu Leu Arg Asn Asp Ala Leu Thr Glu Asn Gly Thr Val Thr
                260                 265                 270
Ile Ser Ala Asp Ser Ala Val Leu Glu His Ser Thr Ile Glu Ser Lys
        275                 280                 285
Ile Ser Gln Ser Val Leu Ala Ala Lys Gly Asp Lys Gly Lys Pro Ala
    290                 295                 300
Val Ser Val Lys Val Ala Lys Lys Leu Phe Leu Asn Gly Thr Leu Arg
305                 310                 315                 320
Ala Val Asn Asp Asn Asn Glu Thr Met Ser Gly Arg Gln Ile Asp Val
                325                 330                 335
Val Asp Gly Arg Pro Gln Ile Thr Asp Ala Val Thr Gly Glu Ala Arg
            340                 345                 350
Lys Asp Glu Ser Val Val Ser Asp Ala Ala Leu Val Ala Asp Gly Gly
            355                 360                 365
Pro Ile Val Val Glu Ala Gly Glu Leu Val Ser His Ala Gly Gly Ile
        370                 375                 380
Gly Asn Gly Arg Asn Lys Glu Asn Gly Ala Ser Val Thr Val Arg Thr
385                 390                 395                 400
Thr Gly Asn Leu Val Asn Lys Gly Tyr Ile Ser Ala Gly Lys Gln Gly
                405                 410                 415
Val Leu Glu Val Gly Gly Ala Leu Thr Asn Glu Phe Leu Val Gly Ser
            420                 425                 430
Asp Gly Thr Gln Arg Ile Glu Ala Gln Arg Ile Glu Asn Arg Gly Thr
        435                 440                 445
Phe Gln Ser Gln Ala Pro Ala Gly Thr Ala Gly Ala Leu Val Val Lys
    450                 455                 460
```

-continued

```
Ala Ala Glu Ala Ile Val His Asp Gly Val Met Ala Thr Lys Gly Glu
465                 470                 475                 480

Met Gln Ile Ala Gly Lys Gly Gly Ser Pro Thr Val Thr Ala Gly
            485                 490                 495

Ala Lys Ala Thr Thr Ser Ala Asn Lys Leu Ser Val Asp Val Ala Ser
                500                 505                 510

Trp Asp Asn Ala Gly Ser Leu Asp Ile Lys Lys Gly Gly Ala Gln Val
            515                 520                 525

Thr Val Ala Gly Arg Tyr Ala Glu His Gly Glu Val Ser Ile Gln Gly
530                 535                 540

Asp Tyr Thr Val Ser Ala Asp Ala Ile Ala Leu Ala Ala Gln Val Thr
545                 550                 555                 560

Gln Arg Gly Gly Ala Ala Asn Leu Thr Ser Arg His Asp Thr Arg Phe
                565                 570                 575

Ser Asn Lys Ile Arg Leu Met Gly Pro Leu Gln Val Asn Ala Gly Gly
            580                 585                 590

Pro Val Ser Asn Thr Gly Asn Leu Lys Val Arg Glu Gly Val Thr Val
                595                 600                 605

Thr Ala Ala Ser Phe Asp Asn Glu Thr Gly Ala Glu Val Met Ala Lys
610                 615                 620

Ser Ala Thr Leu Thr Thr Ser Gly Ala Ala Arg Asn Ala Gly Lys Met
625                 630                 635                 640

Gln Val Lys Glu Ala Ala Thr Ile Val Ala Ser Val Ser Asn Pro
            645                 650                 655

Gly Thr Phe Thr Ala Gly Lys Asp Ile Thr Val Thr Ser Arg Gly Gly
                660                 665                 670

Phe Asp Asn Glu Gly Lys Met Glu Ser Asn Lys Asp Ile Val Ile Lys
            675                 680                 685

Thr Glu Gln Phe Ser Asn Gly Arg Val Leu Asp Ala Lys His Asp Leu
            690                 695                 700

Thr Val Thr Ala Ser Gly Gln Ala Asp Asn Arg Gly Ser Leu Lys Ala
705                 710                 715                 720

Gly His Asp Phe Thr Val Gln Ala Gln Arg Ile Asp Asn Ser Gly Thr
                725                 730                 735

Met Ala Ala Gly His Asp Ala Thr Leu Lys Ala Pro His Leu Arg Asn
            740                 745                 750

Thr Gly Gln Val Val Ala Gly His Asp Ile His Ile Ile Asn Ser Ala
            755                 760                 765

Lys Leu Glu Asn Thr Gly Arg Val Asp Ala Arg Asn Asp Ile Ala Leu
770                 775                 780

Asp Val Ala Asp Phe Thr Asn Thr Gly Ser Leu Tyr Ala Glu His Asp
785                 790                 795                 800

Ala Thr Leu Thr Leu Ala Gln Gly Thr Gln Arg Asp Leu Val Val Asp
                805                 810                 815

Gln Asp His Ile Leu Pro Val Ala Glu Gly Thr Leu Arg Val Lys Ala
            820                 825                 830

Lys Ser Leu Thr Thr Glu Ile Glu Thr Gly Asn Pro Gly Ser Leu Ile
            835                 840                 845

Ala Glu Val Gln Glu Asn Ile Asp Asn Lys Gln Ala Ile Val Val Gly
850                 855                 860

Lys Asp Leu Thr Leu Ser Ser Ala His Gly Asn Val Ala Asn Glu Ala
865                 870                 875                 880

Asn Ala Leu Leu Trp Ala Ala Gly Glu Leu Thr Val Lys Ala Gln Asn
                885                 890                 895
```

Ile Thr Asn Lys Arg Ala Ala Leu Ile Glu Ala Gly Gly Asn Ala Arg
         900                 905                 910

Leu Thr Ala Ala Val Ala Leu Leu Asn Lys Leu Gly Arg Ile Arg Ala
         915                 920                 925

Gly Glu Asp Met His Leu Asp Ala Pro Arg Ile Glu Asn Thr Ala Lys
         930                 935                 940

Leu Ser Gly Glu Val Gln Arg Lys Gly Val Gln Asp Val Gly Gly Gly
945                 950                 955                 960

Glu His Gly Arg Trp Ser Gly Ile Gly Tyr Val Asn Tyr Trp Leu Arg
         965                 970                 975

Ala Gly Asn Gly Lys Lys Ala Gly Thr Ile Ala Ala Pro Trp Tyr Gly
         980                 985                 990

Gly Asp Leu Thr Ala Glu Gln Ser Leu Ile Glu Val Gly Lys Asp Leu
         995                 1000                1005

Tyr Leu Asn Ala Gly Ala Arg Lys Asp Glu His Arg His Leu Leu Asn
         1010                1015                1020

Glu Gly Val Ile Gln Ala Gly Gly His Gly His Ile Gly Gly Asp Val
1025                1030                1035                1040

Asp Asn Arg Ser Val Val Arg Thr Val Ser Ala Met Glu Tyr Phe Lys
         1045                1050                1055

Thr Pro Leu Pro Val Ser Leu Thr Ala Leu Asp Asn Arg Ala Gly Leu
         1060                1065                1070

Ser Pro Ala Thr Trp Asn Phe Gln Ser Thr Tyr Glu Leu Leu Asp Tyr
         1075                1080                1085

Leu Leu Asp Gln Asn Arg Tyr Glu Tyr Ile Trp Gly Leu Tyr Pro Thr
         1090                1095                1100

Tyr Thr Glu Trp Ser Val Asn Thr Leu Lys Asn Leu Asp Leu Gly Tyr
1105                1110                1115                1120

Gln Ala Lys Pro Ala Pro Thr Ala Pro Met Pro Lys Ala Pro Glu
              1125                1130                1135

Leu Asp Leu Arg Gly His Thr Leu Glu Ser Ala Glu Gly Arg Lys Ile
         1140                1145                1150

Phe Gly Glu Tyr Lys Lys Leu Gln Gly Glu Tyr Glu Lys Ala Lys Met
         1155                1160                1165

Ala Val Gln Ala Val Glu Ala Tyr Gly Glu Ala Thr Arg Arg Val His
         1170                1175                1180

Asp Gln Leu Gly Gln Arg Tyr Gly Lys Ala Leu Gly Gly Met Asp Ala
1185                1190                1195                1200

Glu Thr Lys Glu Val Asp Gly Ile Ile Gln Glu Phe Ala Ala Asp Leu
         1205                1210                1215

Arg Thr Val Tyr Ala Lys Gln Ala Asp Gln Ala Thr Ile Asp Ala Glu
         1220                1225                1230

Thr Asp Lys Val Ala Gln Arg Tyr Lys Ser Gln Ile Asp Ala Val Arg
         1235                1240                1245

(2) INFORMATION FOR SEQ ID NO:18:

(i) SEQUENCE CHARACTERISTICS:
        (A) LENGTH: 77 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

```
Arg Arg Ala Arg Arg Ala Leu Arg Gln Asp Phe Phe Thr Pro Gly Ser
1               5                   10                  15

Val Val Val Arg Ala Gln Gly Asn Val Thr Val Gly Arg Gly Asp Pro
                20                  25                  30

Met Gln Gly Val Leu Ala Gln Gly Asp Ile Ile Met Asp Ala Lys Gly
            35                  40                  45

Gly Thr Leu Leu Leu Arg Asn Asp Ala Leu Thr Glu Met Ser Thr Val
        50                  55                  60

Thr Ile Ser Ala Asp Ser Ala Val Leu Glu Met Ser Thr
65                  70                  75
```

(2) INFORMATION FOR SEQ ID NO:19:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

```
Asp Glu Glu Thr Val Lys
1               5
```

(2) INFORMATION FOR SEQ ID NO:20:

(i) SEQUENCE CHARACTERISTICS:
        (A) LENGTH: 46 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

```
Ile Gly Ala Leu Lys Ala Gly Ala Val Glu Ala Ala Ser Pro Arg Arg
1               5                   10                  15

Ala Ala Arg Arg Ala Leu Arg Gln Asp Phe Phe Thr Pro Gly Ser Val
                20                  25                  30

Val Val Arg Ala Gln Gly Asn Tyr Thr Val Gly Arg Gly Asp
            35                  40                  45
```

(2) INFORMATION FOR SEQ ID NO:21:

(i) SEQUENCE CHARACTERISTICS:
        (A) LENGTH: 45 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

```
Arg Gln Asp Phe Phe Thr Pro Gly Ser Val Val Val Arg Ala Gln Gly
1               5                   10                  15

Asn Val Thr Val Gly Arg Gly Asp Pro His Gln Gly Val Leu Ala Gln
                20                  25                  30

Gly Asp Ile Ile Met Asp Ala Lys Gly Gly Thr Leu Leu
            35                  40                  45
```

(2) INFORMATION FOR SEQ ID NO:22:

(i) SEQUENCE CHARACTERISTICS:
        (A) LENGTH: 45 amino acids (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:22:

Arg Gly Asp Pro His Gln Gly Val Leu Ala Gln Gly Asp Ile Ile Met
1               5                   10                  15

Asp Ala Lys Gly Gly Thr Leu Leu Leu Arg Asn Asp Ala Leu Thr Glu
            20                  25                  30

Asn Gly Thr Val Thr Ile Ser Ala Asp Ser Ala Val Leu
        35                  40                  45

(2) INFORMATION FOR SEQ ID NO:23:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:23:

Arg Gly Asp Pro His Gln Gly Val Leu Ala Gln Gly Asp Ile Ile Met
1               5                   10                  15

Asp Ala Lys Gly
            20

(2) INFORMATION FOR SEQ ID NO:24:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:24:

Arg Ala Asp Pro His Gln Gly Val Leu Ala Gln Gly Asp Ile Ile Met
1               5                   10                  15

Asp Ala Lys Gly
            20

(2) INFORMATION FOR SEQ ID NO:25:

(i) SEQUENCE CHARACTERISTICS:
            (A) LENGTH: 20 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:25:

Ala Ala Asp Pro His Gln Gly Val Leu Ala Gln Gly Asp Ile Ile Met
1               5                   10                  15

Asp Ala Lys Gly
            20

(2) INFORMATION FOR SEQ ID NO:26:

(i) SEQUENCE CHARACTERISTICS:
            (A) LENGTH: 20 amino acids
            (B) TYPE: amino acid (C) STRANDEDNESS: single
            (D) TOPOLOGY: linear (ii) MOLECULE TYPE: peptide (xi) SEQUENCE DESCRIPTION: SEQ ID NO:26:

Gly Thr Leu Leu Leu Arg Asn Asp Ala Leu Thr Glu Asn Gly Thr Val
1               5                   10                  15

Thr Ile Ser Ala
            20

(2) INFORMATION FOR SEQ ID NO:27:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:27:

Val Thr Val Gly Arg Gly Asp Pro His Gln Gly
1               5                   10

(2) INFORMATION FOR SEQ ID NO:28:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:28:

Thr Arg Tyr Arg Gly Asp Gln Asp Ala Thr Met Ser
1               5                   10

(2) INFORMATION FOR SEQ ID NO:29:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:29:

Tyr Thr Val Ala Ile Ala Gly Tyr Ala Leu Ala
1               5                   10

(2) INFORMATION FOR SEQ ID NO:30:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:30:

Tyr Thr Val Ala Ile Ala Gly Tyr Ala Leu Ala
1               5                   10

(2) INFORMATION FOR SEQ ID NO:31:

(i) SEQUENCE CHARACTERISTICS:
        (A) LENGTH: 46 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:31:

Ile Gly Ala Leu Lys Ala Gly Ala Val Glu Ala Ala Ser Pro Arg Arg
1               5                   10                  15

Ala Arg Arg Ala Leu Arg Gln Asp Phe Phe Thr Pro Gly Ser Val Val
                20                  25                  30

Val Arg Ala Gln Gly Asn Val Thr Val Gly Arg Gly Asp Pro
                35                  40                  45

(2) INFORMATION FOR SEQ ID NO:32:

(i) SEQUENCE CHARACTERISTICS:
        (A) LENGTH: 47 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:32:

Gly Arg Pro Gln Ile Thr Asp Ala Val Thr Gly Glu Ala Arg Lys Asp
1               5                   10                  15

Glu Ser Val Val Ser Asp Ala Ala Leu Val Ala Asp Gly Gly Pro Ile
                20                  25                  30

Val Val Glu Ala Gly Glu Leu Val Ser His Ala Gly Gly Ile Gly
                35                  40                  45

(2) INFORMATION FOR SEQ ID NO:33:

(i) SEQUENCE CHARACTERISTICS:
        (A) LENGTH: 44 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:33:

Ile Val Val Glu Ala Gly Glu Leu Val Ser His Ala Gly Gly Ile Gly
1               5                   10                  15

Asn Gly Arg Asn Lys Glu Asn Gly Ala Ser Val Thr Val Arg Thr Thr
                20                  25                  30

Gly Asn Leu Val Asn Lys Gly Tyr Ile Ser His Gly
                35                  40

(2) INFORMATION FOR SEQ ID NO:34:

(i) SEQUENCE CHARACTERISTICS:
        (A) LENGTH: 28 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:34:

Pro Met Gln Gly Val Leu Ala Gln Gly Asp Ile Ile Met Asp Ala Lys
1               5                   10                  15

Gly Gly Thr Leu Leu Leu Arg Asn Asp Ala Leu Thr

```
                        20                  25

(2) INFORMATION FOR SEQ ID NO:35:

(i) SEQUENCE CHARACTERISTICS:
        (A) LENGTH: 42 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:35:

Pro Met Gln Gly Val Leu Ala Gln Gly Asp Ile Ile Met Asp Ala Lys
1               5                  10                  15

Gly Gly Thr Leu Leu Leu Arg Asn Asp Ala Leu Thr Glu Met Ser Thr
            20                  25                  30

Val Thr Ile Ser Ala Asp Ser Ala Val Leu
        35                  40

(2) INFORMATION FOR SEQ ID NO:36:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:36:

Pro Met Gln Gly Val Leu Ala Gln Gly Asp Ile Ile Met Asp
1               5                  10

(2) INFORMATION FOR SEQ ID NO:37:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:37:

Ile Asp Val Pro Gln His Gly Gly Ala Met Arg Asp Leu Gly Ile Ala
1               5                  10                  15

Gln Gly Lys Asp
            20

(2) INFORMATION FOR SEQ ID NO:38:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:38:

Val Glu Glu Asp Thr Lys Gly
1               5
```

ANTIBODY RECOGNIZING ENDOTHELIAL CELL LIGAND FOR LEUKOCYTE CR3

RELATED APPLICATIONS

This application is a divisional of application Ser. No. 08/348,353, filed Nov. 30, 1994, which is a continuation-in-part of application Ser. No. 08/247,572, filed May 23, 1994, now abandoned, which is a continuation of PCT/US92/03725, filed May 4, 1992 (U.S. National Stage Application No. 08/140,136), which is a continuation-in-part of application Ser. No. 07/695,613, filed May 3, 1991, now abandoned.

GOVERNMENT SUPPORT

This invention was made with government support under Grant Number A123459 awarded by the National Institutes of Health. The Government has certain rights in the invention.

BACKGROUND OF THE INVENTION

Filamentous hemagglutinin (FHA) is a 220 kD, non-fimbrial surface associated protein produced and secreted by *Bordetella pertussis* (BP). It is a necessary factor for BP to adhere to ciliated respiratory epithelial cells during whooping cough, Tuomanen et al., *J. Infec. Dis.* 152:118–125 (1985). FHA has also been shown to interact with the integrin complement receptor 3 (CR3) on macrophages and other leukocytes, Relman et al., *Cell* 61:1375–1382 (1990). CR3 is also known as Mac-1, $\alpha_M\beta_2$ and CD 11b/CD18. Distinct portions of FHA are responsible for its binding to ciliated respiratory epithelial cells and to leukocytes.

BP binds to two cell types during infection: leukocytes and ciliated cells. Adherence to cilia of the ciliated cells depends on recognition by BP of carbohydrates such as galactose containing glycolipids, Tuomanen et al., *J. Exp. Med.* 168:267–277 (1988).

The BP organism binds to leukocytes by two means. For the first, it binds to the integrin CR3, a step which precedes entry of the bacteria into the leukocyte, as discussed in more detail below. For the second, BP binds to leukocyte carbohydrates. This carbohydrate binding is analogous to that when BP adhere to cilia. Galactose is the minimum requirement for a carbohydrate receptor. It is found, for example, in such blood group determinants as Lewis a.

There are two aspects of a BP infection. One is the invasion of the leukocytes which takes place when BP binds to the integrin of leukocytes. It is a protein/protein interaction. The other aspect is adhesion of BP to the leukocyte or the cilia through a protein/carbohydrate interaction.

The FHA gene of BP has been sequenced, Relman et al., *Proc. Natl. Acad. Sci. USA* 86:2637–2641 (1989) and Domenighini et al., *Molec. Micro.* 4:487–800 (1990), and a number of expression products have been produced, Delisse-Gathoye et al., *Infect. Immun.* 58:2895–2905 (1990).

FHA and the integrin on leukocytes interact in a protein-protein recognition event. The interaction between FHA and leukocyte integrin involves recognition of the arginyl-glycyl-aspartyl sequence at amino acid positions 1097 to 1099 in FHA. This sequence will hereinafter be identified as the RGD sequence or simply, RGD, and the region of FHA or FHA segment on which it occurs as the RGD region. R, G and D are the standard one letter abbreviations for arginine, glycine and aspartic acid.

It has long been known that leukocytes can invade or pass through vascular endothelial tissue by a process in which integrins, such as CR3, bind to receptors for integrins on the surface of endothelial cells as a step in a sequence of reactions which results in a widening of the junctions between such cells to permit passage by the leukocytes. The receptors for CR3 on endothelia are referred to herein as integrin receptors. There may be one or more than one such integrin receptor.

Another molecule which binds to the integrin CR3 is the serum complement component C3bi, an opsonin. Bacteria which have the C3bi component fixed to their surface by any means, such as a binding event during a host recognition process, are bound to the leukocyte integrin in such a way that the bacteria are taken up and killed by the leukocyte.

In addition to the ability to recognize C3bi, FHA and integrin receptors on endothelial cells, CR3 also binds to Factor Ten of the coagulation cascade (Altieri et al., *Science* 254:1200–1202, 1992). The coagulation cascade is involved in inflammation since procoagulant activity arises on endothelial cells during infection or other noxious stimuli. Three regions of Factor Ten participate in recognition of CR3.

To summarize, FHA, C3bi, Factor X and endothelial cell integrin receptors are molecules with binding regions for CR3.

A particular infection in which leukocyte mediated damage contributes to morbidity and mortality of disease is bacterial meningitis. Depending upon the infecting organism, thirty percent of the cases of meningitis per year die despite sterilization of the infection by antibiotics. Over fifty percent of the survivors have permanent and severe sequelae such as paralysis, deafness, and learning disabilities. Obviously, the prevention and/or diminishment of such damage would greatly enhance the quality of life for the survivors of this disease.

Activated leukocytes also contribute to cerebral edema and blood-brain barrier injury. Neutropenic animals (animals in which the leukocytes have been artificially diminished) have been found to have improved survival rates in experimentally induced disease. A high amount of inflammation in the subarachnoid space correlates directly with a poor outcome of disease. Inhibition of the accumulation of leukocytes in cerebrospinal fluid directly correlates with improved morbidity and mortality of experimental pneumococcal meningitis and of *Haemophilus influenzae* meningitis and bacteremia in children.

Clearly, an agent which would inhibit the influx of leukocytes into infected sites would be a therapeutic tool of immense value particularly if non-leukocyte mediated defense systems are left functionally intact. It would further be beneficial to block leukocyte diapedesis only at inflamed sites and not at other sites throughout the body. Thus, treatment directed at inflamed endothelia would be advantageous over that directed to leukocytes.

The use of antibiotics magnifies the deleterious effects of inflammation during infectious diseases. This is due to the mechanism by which such agents exert their antiinfective effects. For example, following the administration of a beta-lactam antibiotic (or another cell-wall directed antibiotic), the bacteria disintegrate due to lysis by the antiinfective agents. The resulting fragments of bacteria initiate a dramatically enhanced inflammatory response. Earlier research has indicated that inhibition of this enhanced level of inflammation correlates with improved morbidity and mortality, Tuomanen et al., *J. Infect. Dis.* 155:985–990 (1985) and Kadurugamuwa, Program and Abstracts of the 27th ICAA Meeting, p. 205 (1987). In penumococcal meningitis, for instance, mortality can be directly correlated with the amount of meningeal inflammation, McAllister et al., *J. Infect. Dis.* 132: 355–360 (1975). Thus, a method of dampening inflammation during the course of therapy with an antibiotic would be advantageous in treating infections, particularly meningitis, septic arthritis, and endophathalmitis.

SUMMARY OF THE INVENTION

It has been discovered that FHA has polypeptide regions with binding properties homologous to those of C3bi, Factor X and an integrin receptor on endothelial cells. Thus, FHA and these molecules are functionally related by their binding homologies. They are also antigenically related and therefore may be structurally related. As a result of these binding homologies, some antibodies to FHA cross react with endothelial cells. There may be one or several distinct molecules on endothelial cells which function as integrin receptors by interacting with leukocyte integrins and by binding some cross-reactive anti-FHA antibodies. In addition, since FHA contains four regions with sequence similarity to three regions in Factor X, some antibodies to any of these four FHA regions cross react with the three regions in Factor X. Similarly, some antibodies to FHA cross react with C3bi. Moreover, there is species cross reactivity of antibody recognition of antigen. Thus, antibodies to FHA raised in a goat, mouse, guinea pig or human can react with and bind to C3bi, Factor X or endothelial cells of rats, rabbits and humans.

It has also been discovered, in this regard, that polypeptide regions of FHA can bind to leukocytes and competitively inhibit the binding of Factor X or C3bi to leukocytes or leukocytes to endothelial cells.

In addition, it has been discovered that polypeptide segments of C3bi also competitively inhibit binding of C3bi to leukocytes. It has also been discovered that polypeptide segments of Factor X competitively inhibit binding of leukocytes to endothelial cells.

There are a number of significant consequences of these important discoveries. They are:

1. Peptides which contain or are analogs of the RGD region or one of the Factor X regions of FHA will bind to the CR3 integrin of leukocytes, thereby preventing adherence of the leukocyte to endothelial cells. Such an adherence inhibition can be used in a procedure for lessening the deleterious inflammatory process, particularly when the inflammatory process involves leukocyte adhesion to endothelial cells which are part of the blood-brain barrier.

2. Peptides or analogs thereof which interact with leukocytes in competition with Factor X or C3bi can be used to inhibit blood coagulation or opsonization and phagocytosis, respectively. These peptides or analogs prevent the binding of Factor X or C3bi to the CR3 integrin of leukocytes. Such competitive binding can be used to inhibit the inflammatory process where this process involves Factor X or C3bi.

3. Antibodies to FHA will bind to homologous regions of normal proteins in animals and disturb the function of these proteins. In the case of the C3bi-like region, the appropriate antibodies will bind C3bi or other related complement components and render them less effective for opsonization. In the case of the Factor X-like regions, the appropriate antibodies will disturb coagulation and prevent amplification of inflammation by the coagulation cascade. Appropriate antibodies to the Factor X-like regions of FHA will also prevent leukocyte recruitment during an inflammatory response. In the case of the region containing RGD, the appropriate antibodies to FHA will bind to endothelial cells of, for example, the blood brain barrier and selectively open the junction between the cells in a manner analogous to the opening of the endothelia during leukocyte diapedesis thereby making possible the entry of desirable therapeutic agents into the cerebrospinal fluid (CSF) of the subarachnoid space and into the brain parenchyma without simultaneously admitting leukocyte entrance. These antibodies will also serve an anti-inflammatory function by binding to such endothelial cells and prevent leukocyte attachment to these cells as well as the subsequent transmission or migration of leukocytes into the CSF.

4. Peptides containing the carbohydrate recognition domain (CRD) of region 1141–1279, or analogs thereof, are optimal vaccines for whooping cough because they generate antibodies which block adherence of bacteria to the respiratory tract and thereby prevent disease. Elimination or modification of the other regions of FHA is important in optimizing the vaccine in order to prevent generation of antibodies which cross react with natural CR3 ligands such as Factor X, C3bi, or integrin receptors on endothelial cells.

5. Peptides of each of the endothelial cell integrin receptor, Factor X or C3bi domains of FHA are useful in vaccine quality control. They can be used to detect the ability of a vaccine candidate to generate antibodies in serum which is reactive with the endothelial cell integrin receptors, Factor X-like domains or the C3bi domain. Such antibodies would be deemed toxic.

Those skilled in the art will recognize that there are four fundamental procedures for taking advantage of the discoveries upon which this invention is based. One involves the utilization of FHA or regions of FHA or antibodies thereto to prevent functions involving CR3 in inflammation. These are exemplified by consequences 1, 2 and 3. Consequence 3 also exemplifies that appropriate antibodies to FHA selectively permeabilize the blood-brain barrier to therapeutic or diagnostic agents. In consequence 4, antibodies to particular regions of FHA prevent adhesion of BP to the respiratory tract. Consequence 5 may be employed to detect toxic vaccines.

This invention also is directed to peptides derived from FHA, analogs of such peptides and antibodies to such peptides, all of which are capable of inhibiting binding between CR3 and its natural ligands. It is also directed to pharmaceutical compositions containing these products and to therapeutic use of such products to inhibit or prevent such binding and to other uses which flow from these basic properties. The invention relates also to genes which may be used in accordance with known techniques to produce the products employed in the invention.

The process of this invention will be useful in treating inflammation caused by any of a variety of infective agents, including gram-positive and gram-negative bacteria as well as viruses and fungi. Particularly targeted infections are those which are susceptible to treatment with beta-lactam antibiotics, or antiviral agents such as *Haemophilus influenzae* B; *N. meningitidis* b; pneumococci, e.g., *Streptococcus pneumoniae; Escherichia coli; Staphylococcus epidermidus; Staphylococcus aureus*; group B Streptococci; Salmonella; *Bacillus subtillis; Pseudomonas aeruginosa*; and Herpes virus.

BRIEF DESCRIPTION OF THE FIGURES

FIG. 1 shows regions of FHA which mimic human proteins that bind to CR3 with the mapping relative to the CRD.

FIG. 3 is a representation of peptides suitable for vaccines.

FIGS. 10A–10L show the sequence for the gene encoding Fragment 7 and for Fragment 7 itself.

FIG. 11 shows deletions of the FHA gene which will result in truncated FHA molecules useful for vaccines.

FIG. 20 is a graphical representation of the anti-inflammatory activity of FHA, and FHA- and factor X-derived peptides in experimental bacterial meningitis.

*statistically significant difference from control at p<0.01 (Mann-Whitney test).

Figure 21:
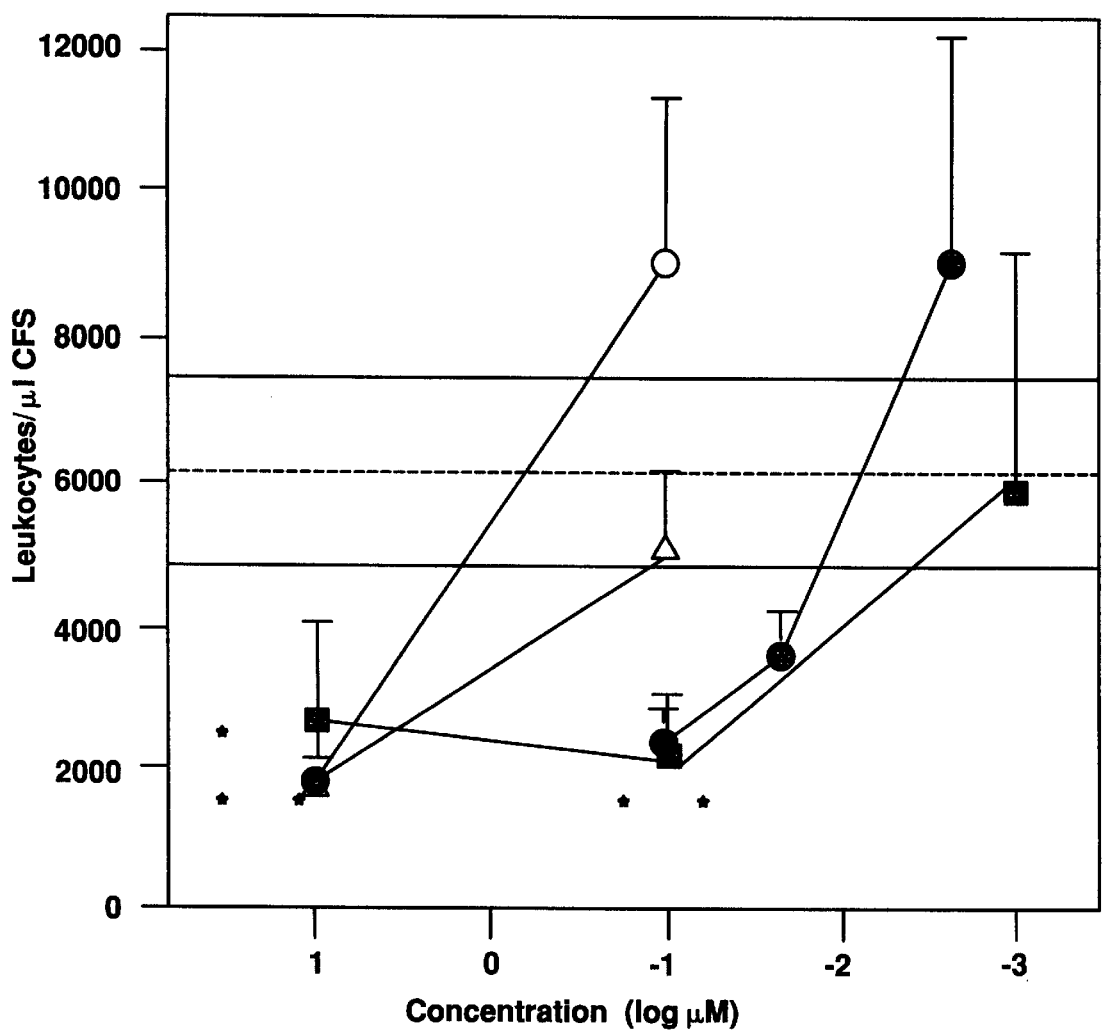

FIG. 21 is a graphical representation of the effect of concentration of peptide on inhibition of leukocyte migration into the CSF. FHA peptide Ia O, FHA peptide II ■; Factor X peptide II ▲ (n≧4 per group). Two animals received intravenous injections of $10^{-1}$ $\mu$M, $2\times10^{-2}$ $\mu$M or $2\times10^{-3}$ $\mu$M FHA (●). Values are means±standard deviations of leukocyte densities at 7 hours after bacterial challenge. The horizontal lines indicate the mean and standard deviation of CSF leukocyte density in 10 control animals which received phosphate buffered saline.

*Values for animals treated with 10 $\mu$M of all 3 peptides and $10^{-1}$ $\mu$M FHA peptide II are statistically significantly different from control at p<0.02. Value for animals treated with $10^{-1}$ $\mu$M FHA is statistically significantly different from control at p<0.05 (Mann-Whitney test).

Figure 22:
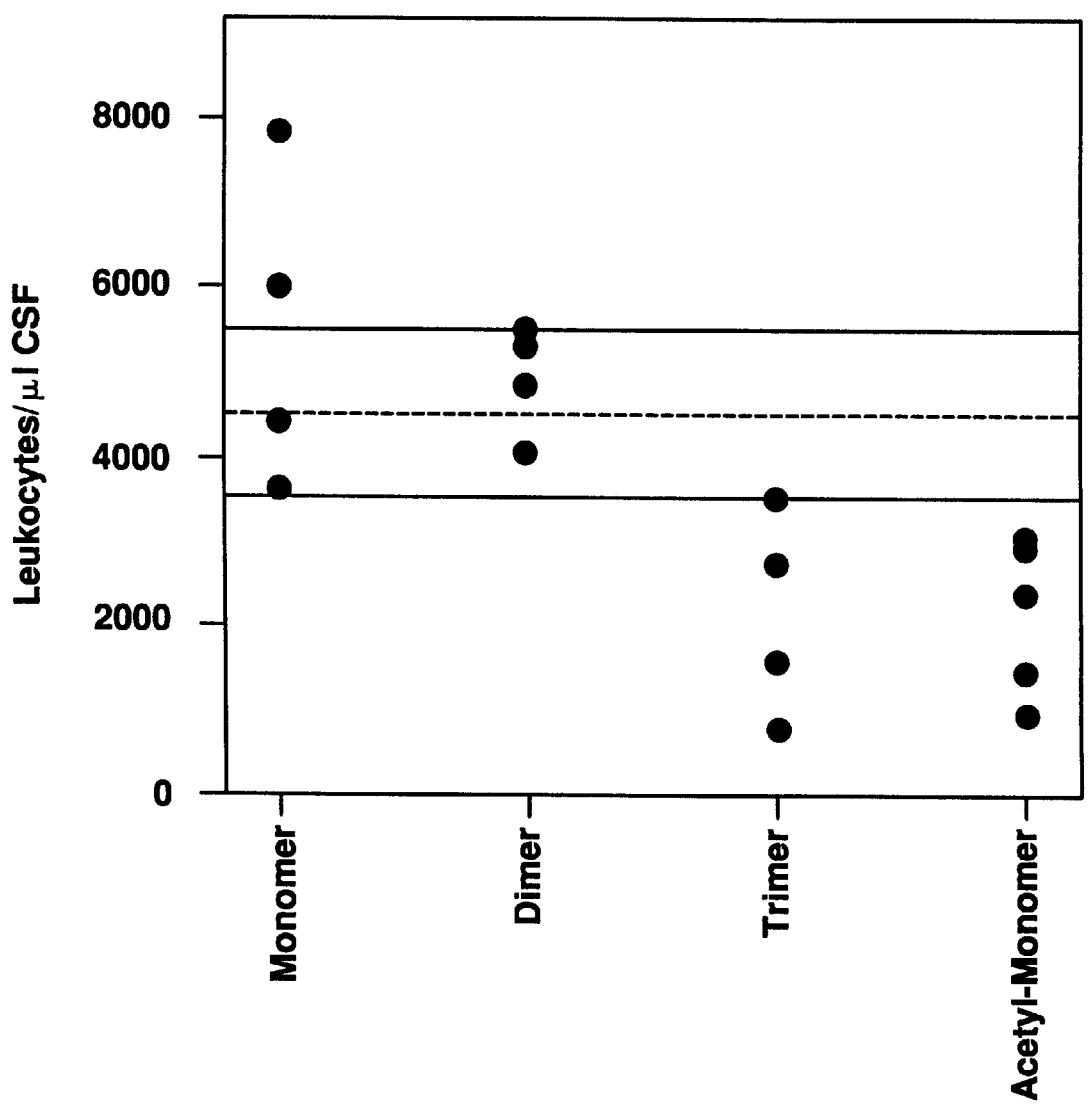

FIG. 22 is a scattergram representation of the effect of variation of the FHA peptide II structure on efficacy of inhibition of meningeal inflammation. Values are leukocyte densities at 7 hours for individual rabbits. The horizontal lines indicate the mean and standard deviation of CSF leukocyte density in 10 control animals which received phosphate buffered saline.

Figure 23:
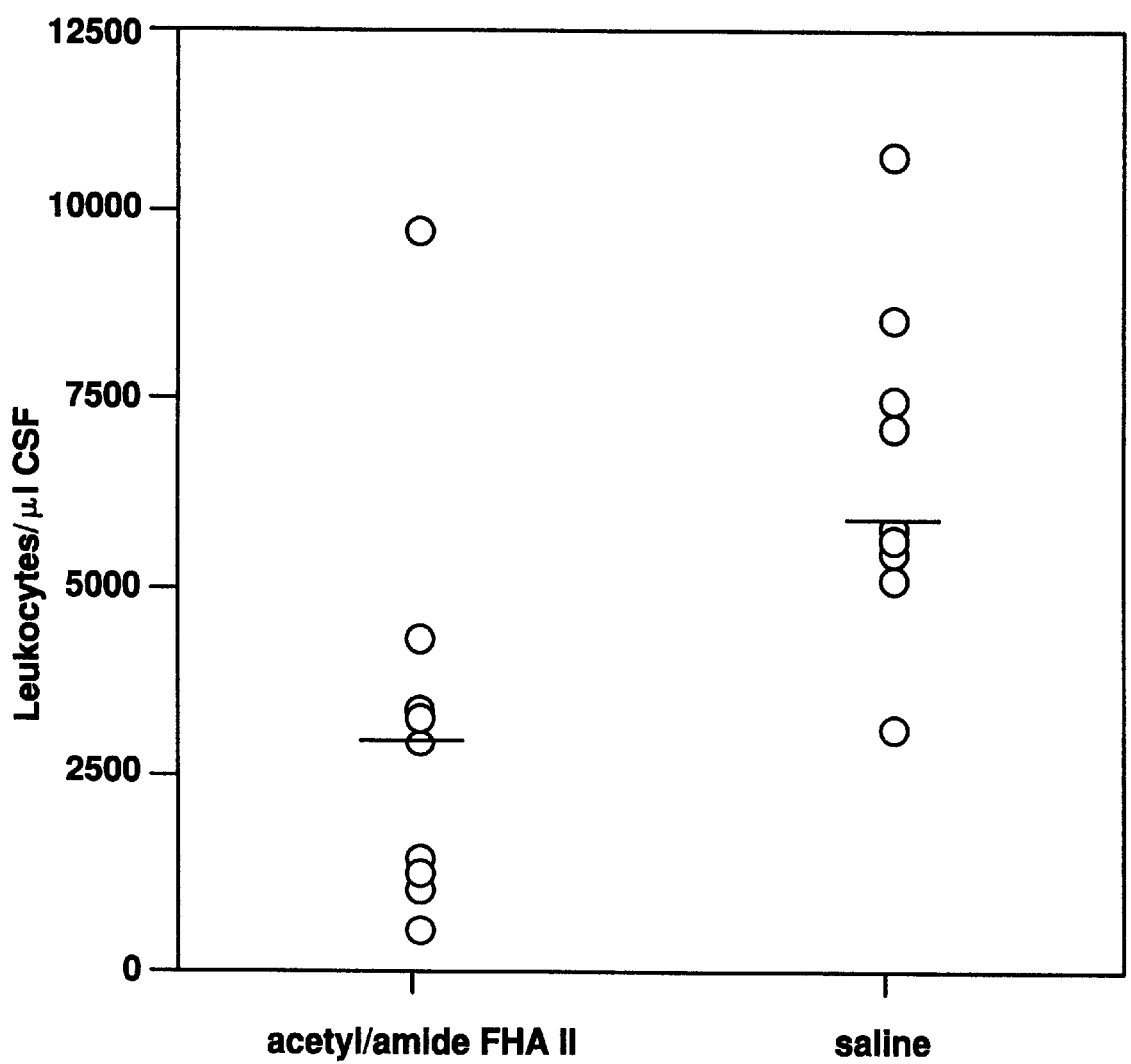

FIG. 23 is a scattergram representation of the ability of acetyl/amide FHA peptide II to inhibit accumulation of leukocytes in the CSF. Two groups of 10 animals were challenged with pneumococci. One hour later, the animals received an intravenous injection of 10 nmoles of the acetyl/amide peptide (8.2 $\mu$g) or phosphate buffered saline. Leukocyte density in CSF was determined 6 hours after pneumococcal challenge. The mean values as indicated by the bars are statistically significantly different at p=0.0015 by ANOVA.

FIG. 24 is a listing of the sequences of FHA-derived synthetic peptides investigated for inhibitory properties toward neutrophil adherence to endothelial cells and transendothelial migration of neutrophils through endothelia.

Figure 25A:
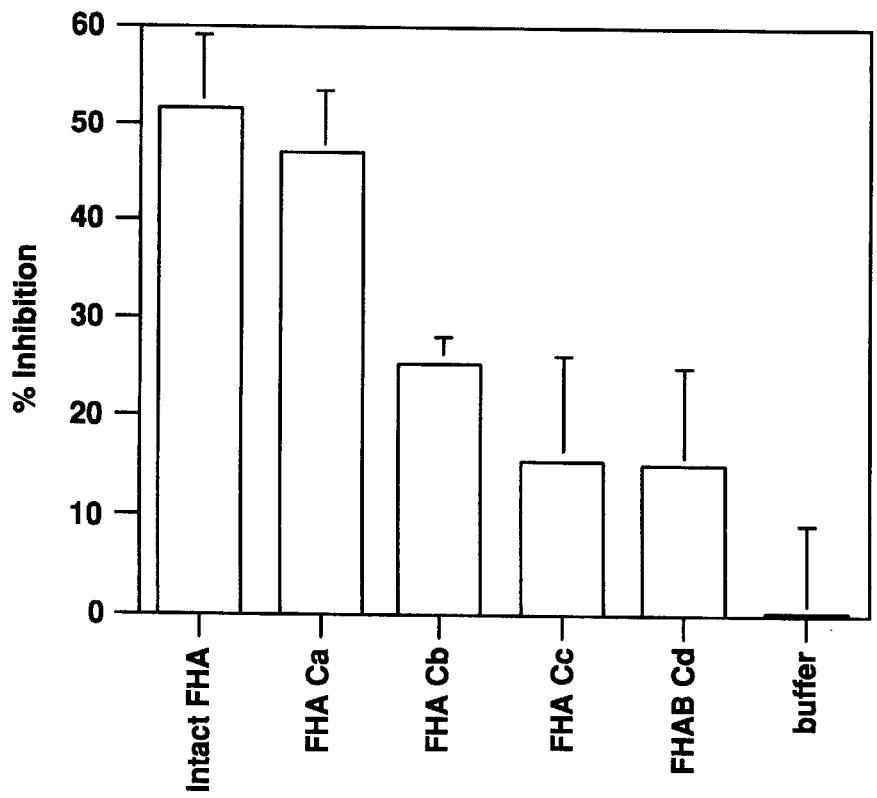
Figure 25B:
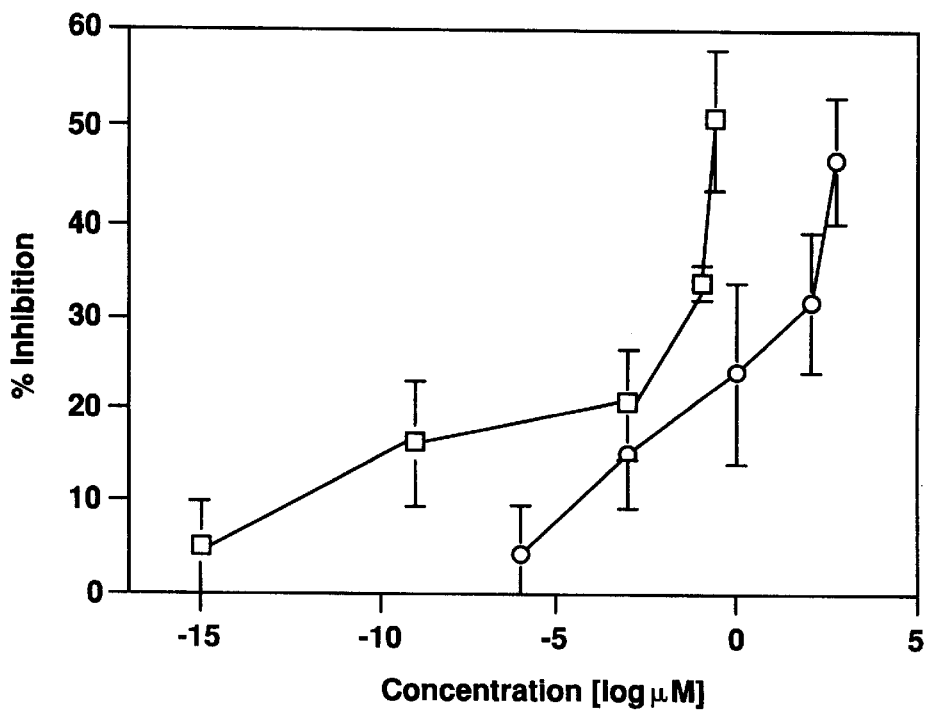

FIG. 25 is a graphical representation of the inhibition of neutrophil adherence to activated endothelial cells by FHA and FHA peptides. FIG. 25A: Peptide concentrations were 0.5 mM (FHA 0.2 $\mu$M). Values represent mean±standard deviation of four experiments with 5 wells/peptide; FIG. 25B represents the mean±standard deviation of triplicate experiments with 5 wells/peptide. Native FHA (□); FHA peptide Ca (O).

Figure 26:
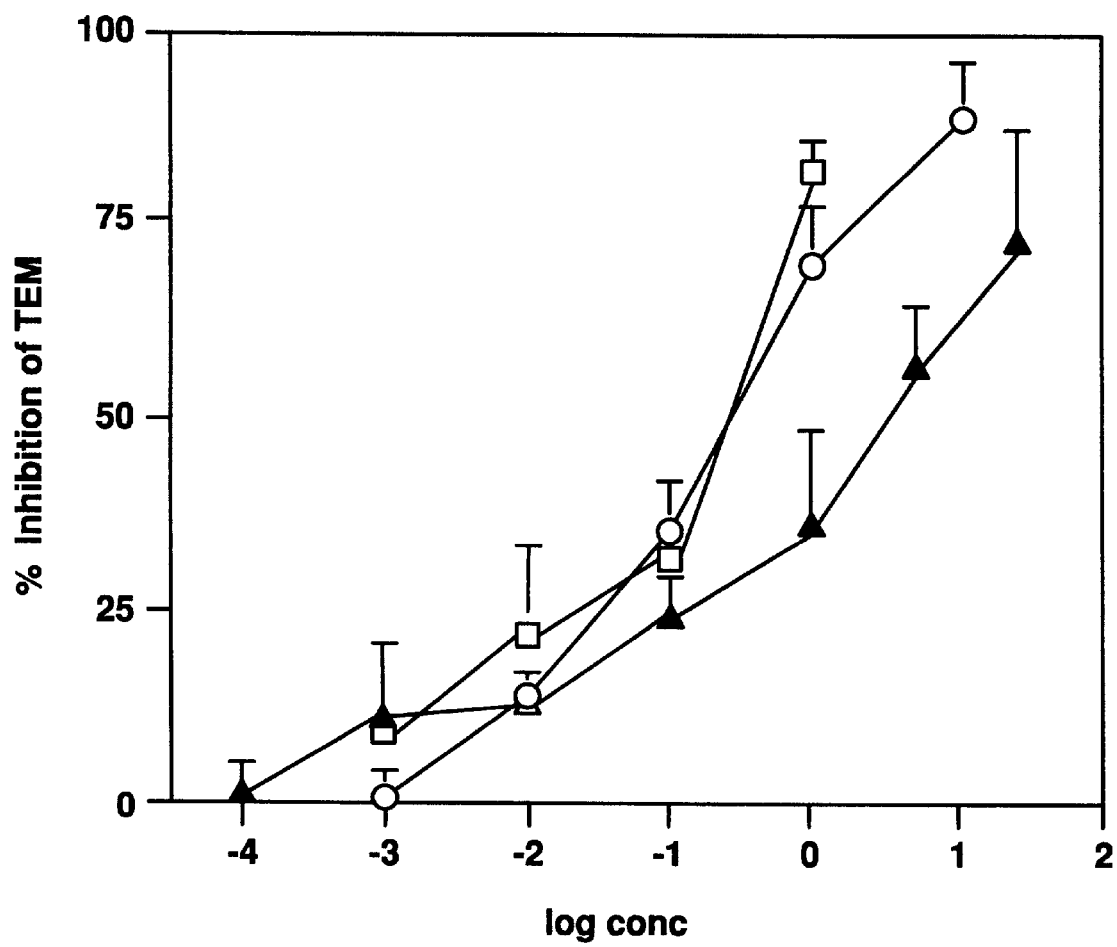

FIG. 26 is a graphical representation of the inhibition of transendothelial migration of neutrophils by FHA peptide Ca, native FHA and mAb IB4 in a concentration dependent fashion. FHA peptide Ca (O); intact FHA (□); and mAb IB4 (▲). Values represent mean±standard deviation of at least 3 experiments with 6 wells/peptide.

Figure 27:
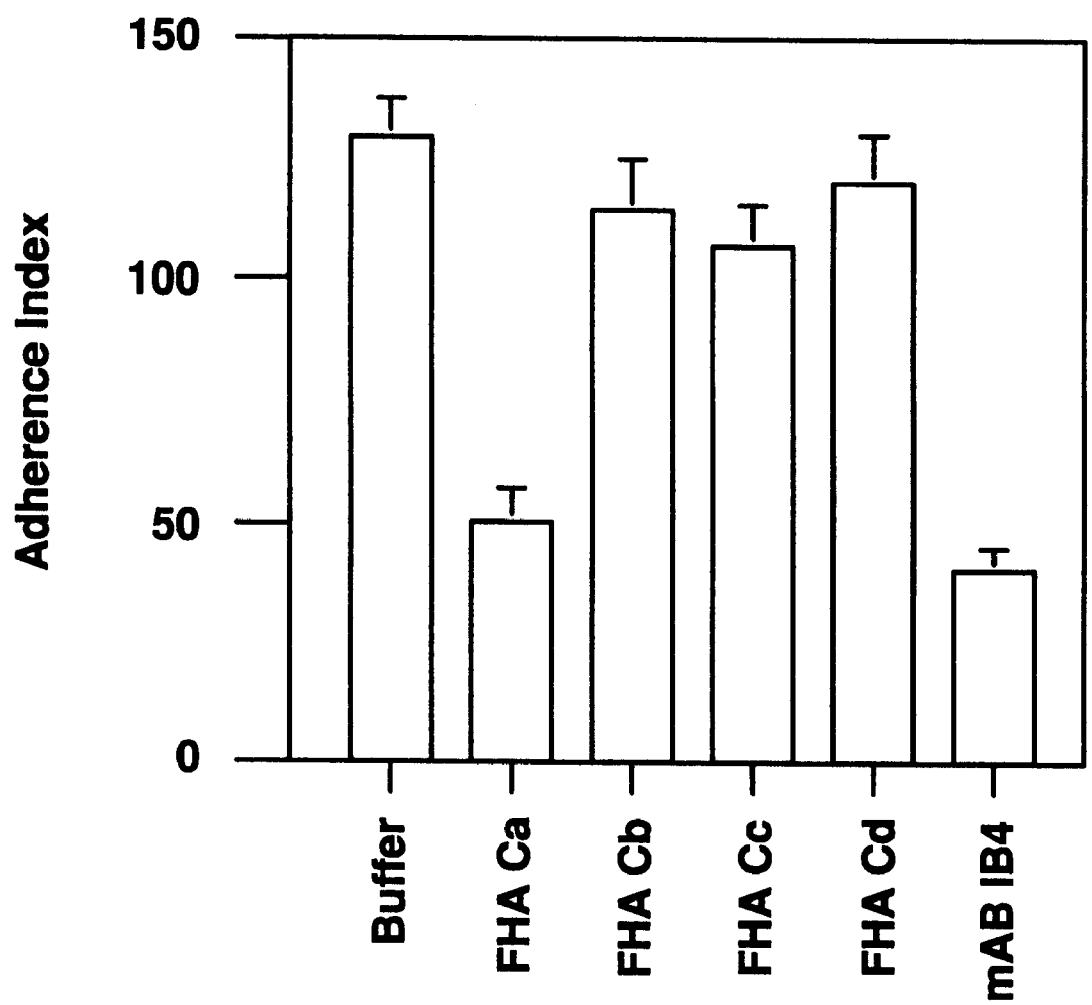

FIG. 27 is a bar graph representation of the downmodulation of CD11b/CD18 by FHA-peptides. mAb IB4 (50 $\mu$g/ml) served as a positive control. Data represent means±standard deviations of triplicate experiments with 6 wells/peptide.

Figure 28:
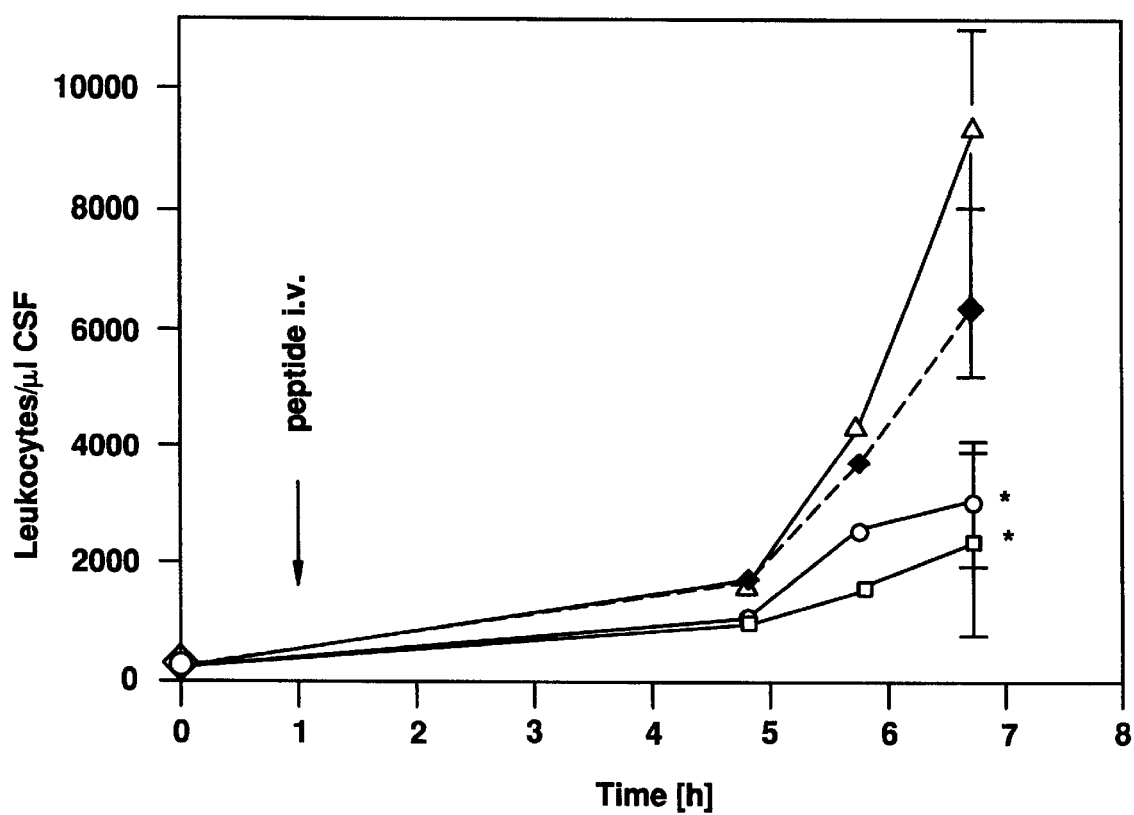

FIG. 28 is a graphical representation of the effect of FHA peptides on pneumococci induced leukocyte migration into the CSF during pneumococcal meningitis. Data represent mean±standard deviation of leukocyte concentration/$\mu$l CSF of at least 4 animals per group. Time is hours after pneumococcal challenge. FHA peptide Ca (□); FHA peptide Cb (O); FHA peptide Cd (▲); Control (♦);
*statistically significant different from control at p<0.02 (Mann-Whitney test).

Figure 29:
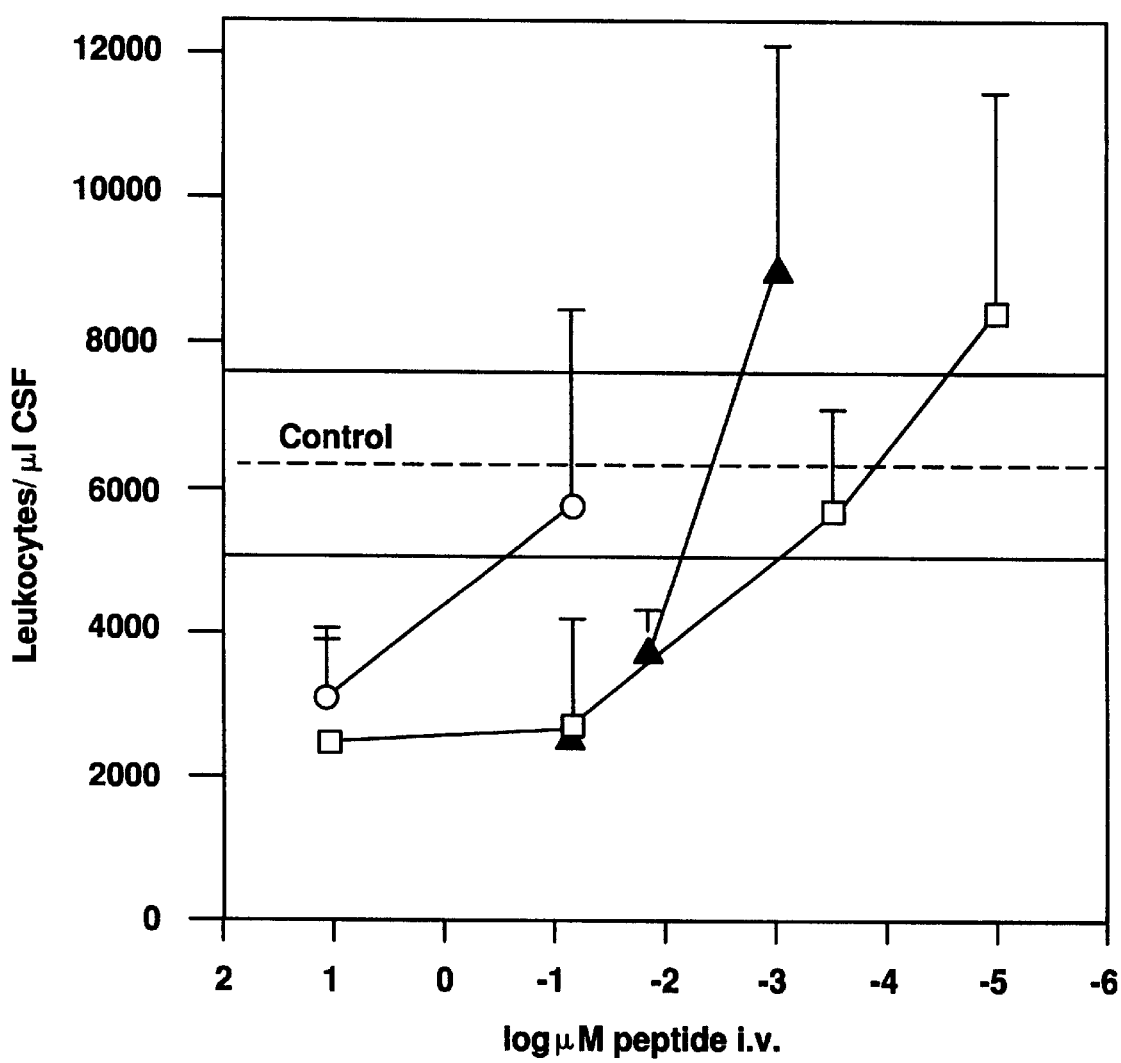

FIG. 29 is a graphical representation of a comparison of anti-inflammatory activity of FHA and FHA peptides in experimental meningitis. FHA peptide Ca (□); FHA peptide Cb (O), ≧four animals/group; FHA (▲), two animals/group. Values are means±standard deviations of leukocyte concentrations/μl CSF at 7 hours after bacterial challenge. The horizontal lines indicate the mean±standard deviation of leukocyte concentrations in 10 control animals which received phosphate buffered saline.

Figure 30:
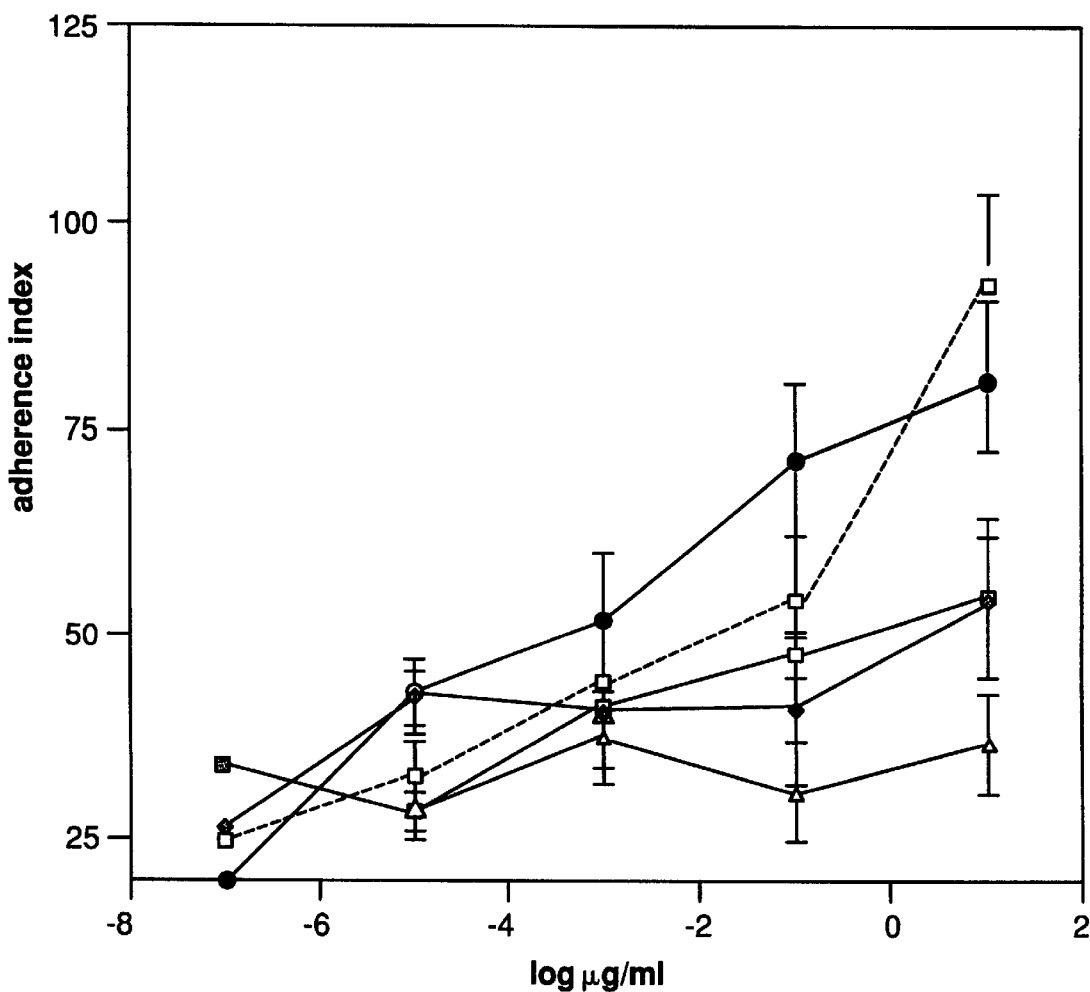

FIG. 30 is a graphical representation of the ability of particular anti-FHA monoclonal antibodies to bind C3bi coated erythrocytes. anti-C3bi (□); 12.5A9 (♦); 12.1F9 (●); 12.2B11 (■); 12.6F8 (Δ). Values are representative of 5 experiments with duplicate wells. In wells coated with control IgG1 (anti-von Willebrand factor antibody), the adherence index was consistently <30. Using a one way analysis of variance, significant differences between antibody and control were not found for 12.5A9, 12.6F8 and 12.2B11 (p>0.5); significant differences were found for 12.1F9 (p=0.009) and anti-C3bi (p=0.002).

Figure 31:
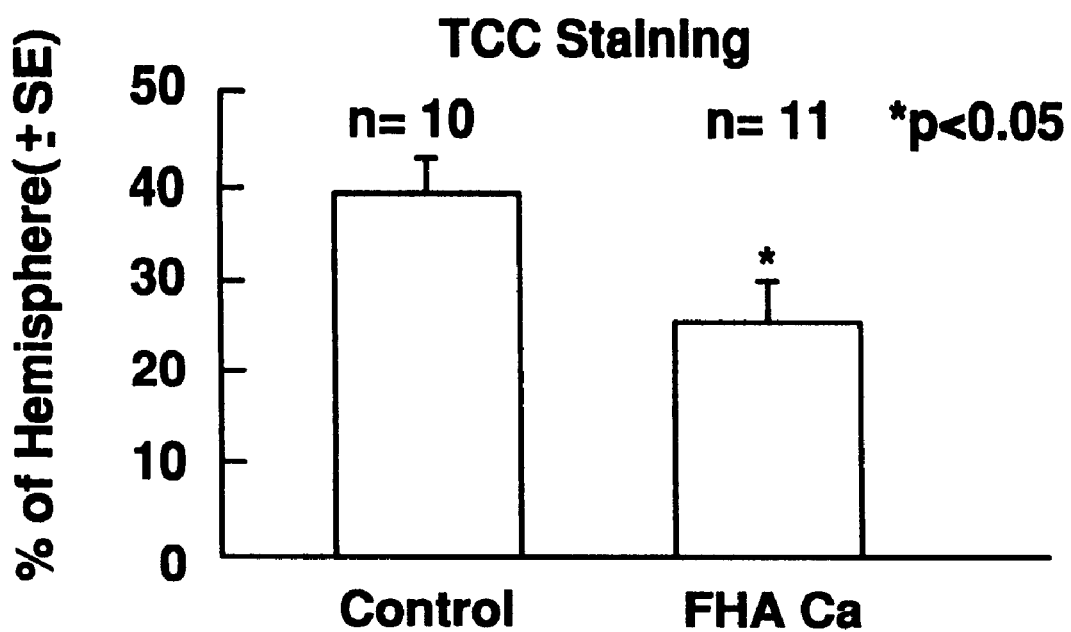

FIG. 31 is a bar graph representation of the reduction in infarct volume in rat brain sections following treatment of FHA peptide Ca 2 hour MCAo; 2 day survival.

DETAILED DESCRIPTION OF THE INVENTION

FHA or particular polypeptide regions of it can serve an antiinflammatory function by acting as competitive inhibitors of CR3 recognition of endothelial cells (at least one region), C3bi (at least one region), or Factor Ten (at least three of four regions). Another separate and distinct region of FHA is the carbohydrate recognition domain (CRD) which allows the bacteria to adhere to cilia. The CRD and segments and analogs thereof can serve as a vaccine against whooping cough, particularly if they are dissociated from the other domains of FHA which can generate toxic cross reactive antibodies if included in vaccines because these domains are binding homologs of human proteins.

For convenience in discussing these various properties of FHA, each region is defined according to the scheme in FIG. 1. Regions A, B, C and D are defined by the binding of particular monoclonal antibodies as in Delisse-Gathoye et al., *Infect Immun* 58:2895–2905 (1990) and are bounded by the amino acid residues as shown. Region A contains the CRD. Region B contains the domain which mimics binding properties of C3bi. Regions consistent with Factor Ten-like domains are represented by *. The region including the RGD (residues 1097–9) mimics the endothelial cell ligand for CR3 which participates in leukocyte transmigration.

The understanding of this invention will be facilitated if certain of the terms used in the description thereof are defined.

The terms "peptide" and "polypeptide" are often used interchangeably to denote unbranched chains of amino acids linked together by peptide bonds. The term "peptide" conventionally refers to two or more amino acids joined together by peptide bonds and the term "polypeptide" conventionally refers to longer peptide chains. These conventional definitions will be adhered to herein; "peptide" will refer to shorter chains of amino acids (e.g. 5 or more amino acid residues) and "polypeptide" will refer to longer chains of amino acids (e.g. 20 or more amino acid residues). The term "protein" will be used herein in the conventional sense as a naturally occurring chain of amino acids (most often a polypeptide) which usually has a biological function. The peptides and polypeptides of the present invention encompass amino acid and peptide analogs, as described infra, as well as amino acid additions, deletions or substitutions to previously described or known peptides or polypeptides. The peptides and polypeptides of the present invention can be understood as having functions as discussed herein. These functions include inhibition of binding between the CR3 integrin and its natural ligands which include Factor X, C3bi and an integrin receptor on endothelial cells. They may do so because they contain an RGD triplet, or a peptide moiety which functions as if it contained an RGD triplet, or by mimicking C3bi or Factor X peptides. These peptides are useful in the control of inflammation. Peptides of the CRD region are useful as nontoxic vaccines.

The term "antibodies" encompasses both polyclonal and monoclonal antibodies which bind to C3bi (or related complement components), Factor X or integrin receptors on brain endothelium. The preferred antibody is a monoclonal antibody. The term antibody is also intended to encompass mixtures of more than one antibody (e.g., a cocktail of different types of monoclonal antibodies). The term antibody is further intended to encompass whole antibodies, single chain antibodies, chimeric antibodies comprising portions from more than one species, chimeric proteins comprising a functional portion of antibody coupled by covalent or recombinant techniques to an intact protein or functional portion thereof that is not of antibody origin (i.e. a chimeric antibody-protein), bifunctional antibodies, biologically functional fragments of the aforementioned, etc. Biologically functional antibody fragments which can be used are those fragments sufficient for binding of the antibody fragment to FHA or the integrin receptor as well as Factor X and C3bi.

The chimeric antibodies can comprise portions derived from two different species (e.g., human constant region and murine binding region). The portions derived from two different species can be joined together chemically by conventional techniques or can be prepared as a single fusion protein using genetic engineering techniques. DNA encoding the proteins of both portions of the chimeric antibody can be expressed as a single fusion protein.

The term "RGD region" includes any RGD containing segment of a molecule that interacts with a complementary molecule through the involvement of the RGD triplet. There are molecules which bind to their complementary molecules as if they possess the RGD region and these molecules can be used in the practice of this invention. Native molecules containing RGD as well as chemically treated native molecules or derivatives of these molecules are included in this definition.

The term "block the RGD region" will be used to describe peptides or polypeptides which inhibit adhesion between leukocytes and endothelial cells for any of a number of reasons. They may do so because the cells bind to all three of the amino acid residues of RGD or to only one or two of them. They may also do so because the cells bind to molecular segment(s) neighboring the RGD region in such a manner that the exposed RGD triplet of the molecule blocks leukocyte-endothelial cell adhesion.

The term "Factor X-like region" refers to any segment of a molecule containing amino acid sequences GYDTKQEDG (SEQ ID NO: 1), IDRSMKTRG (SEQ ID NO: 2) or GLYQAKRFKVG (SEQ ID NO: 3) or highly similar sequences that inhibit Factor X binding to the CR3 integrin.

The antibodies useful in the practice of this invention can be raised against whole bacteria containing FHA or FHA derivatives or against native FHA itself or chemically treated FHA or FHA derivatives. This procedure will usually be employed to produce polyclonal antibodies. They can also be raised to analogs of FHA or fragments or segments of analogs of FHA thereof produced either by genetic manipulation of the FHA gene or by chemical modification or enzymatic cleavage of the whole protein or a fragment of the protein. The antibodies can be produced, and this is the preferred method, by raising monoclonal antibodies to the expression products from the FHA gene, segments thereof, or mutants of such segments according to the method of Delisse-Gathoye et al., supra. The expression products are proteins or peptides containing a sufficient number of amino acid residues to elicit an antibody response alone or when attached to other antigenic determinants or in the presence of adjuvants. The antibodies can be produced in accordance with well known procedures for the production of monoclonal antibodies. These monoclonal antibodies are preferred therapeutic agents for the practice of this invention.

The presently preferred monoclonal antibodies are 12.5D1, 12.1F9, 13.6E2, 12.6F8, 12.2 B11 and 12.5A9 produced by the methods described by Delisse-Gathoye et al., supra or monoclonal antibodies with binding characteristics substantially similar to these specified monoclonal antibodies. A preferred polyclonal antibody is goat antiserum to FHA produced by the Cowell procedure as described in Tuomanen et al. cited above.

Presently preferred antiinflammatory products of this invention are peptides and polypeptides containing from about five to about forty-five amino acid residues, preferably about twelve to thirty five amino acids, and their analogs, especially those peptides and polypeptides shown in FIGS. 2A (SEQ ID NO: 4 to SEQ ID NO: 6) and 2B (SEQ ID NO: 7 to SEQ ID NO: 10). The most preferred peptides and polypeptides are polypeptide III (amino acid residues 1097–1141) of FIG. 2A and the ETKEVDG peptide (SEQ ID NO: 7) of FIG. 2B. These are preferred because they are relatively small molecules which can be readily prepared in pure form by chemical synthesis. It will be apparent from the description of the invention that the invention is not limited to these peptides.

Presently preferred vaccine products of this invention are the polypeptides shown in FIG. 3 (SEQ ID NO: 11 to SEQ ID NO: 14) and their analogs.

A peptide of this invention will be useful in any one of four cases: 1) if it is capable of reducing or inhibiting adhesion between leukocytes and endothelia or of raising antibodies having these properties; 2) if it is capable of generating an antibody that binds to endothelial cells, including those of the blood brain barrier, thereby increasing the permeability of the endothelial barrier to passage of molecules from the bloodstream to the interstitial spaces of the target organ (whether or not leukocyte transmigration is affected); 3) if it is capable of reducing or inhibiting Factor X or C3bi binding to leukocytes or of raising antibodies having these properties; or 4) if it is capable of inhibiting adhesion between BP and cilia or of raising antibodies having these properties.

It will be clear from these utilities that peptides of this invention may contain amino acid derivatives comprising single or multiple amino acid additions, deletions and/or substitutions compared to the amino acid sequence of FHA. The peptides contemplated herein may be chemically synthesized such as by solid phase peptide synthesis or may be prepared by subjecting a designated polypeptide to hydrolysis or other chemically or enzymatically disruptive processes whereby fragments of the molecule are produced. Alternatively, the peptides can be made in vitro or in vivo using recombinant DNA technology. In this case, the peptides may need to be expressed in combination with other proteins and then subsequently isolated by chemical cleavage or the peptides may be expressed in multiple repeat units. Furthermore, multiple antigen peptides can also be prepared according to the method of Tam et al., *J. Am. Chem. Soc.* 105:6442–6445 (1988). The selection of a method of producing the subject peptides will depend on factors such as the required type, quantity and purity of the peptides as well as ease of production and convenience.

The use of these peptides in vivo may first require their chemical modification since the peptides themselves may not have a sufficiently long serum and/or tissue half-life. Such chemically modified peptides are referred to herein as "analogs". The term "analog" extends to any functional chemical equivalent of a peptide characterized by its increased stability and/or efficacy in vivo or in vitro in respect of the practice of the invention.

Analogs of the peptides contemplated herein include, but are not limited to, modifications to amino acid side chains, incorporation of unnatural amino acids and/or their derivatives during peptide synthesis and the use of crosslinkers and other methods which impose conformational constraints on the peptides or their analogs. Analogs of the peptides also include modifications of the end groups of the peptide, such as chemical additions or substitutions. For example, acetylation of the free amine group of the amino terminal amino acid or amidation of the carboxyl group of the carboxy terminal amino acid are contemplated herein as functional peptide end group modifications. A particularly preferred composition of the present invention is the FHA peptide II (SEQ ID NO: 7) where an acetyl group is attached to the N-terminus and an amide group is attached to the C-terminus, thereby forming an acetyl/amide derivative of FHA II.

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2, 4, 6, trinitrobenzene sulfonic acid (TNBS); acylation of amino groups with succinic anhydride and tetrahydrophthalic anhydride; and pyridoxylation of lysine with pyridoxal-5'-phosphate followed by reduction with $NaBH_4$.

The guanidino group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivatisation, for example, to a corresponding amide.

Sulfhydryl groups may be modified by methods such as carboxymethylation with iodoacetic acid or iodoacetamide; performic acid oxidation to cysteic acid; formation of a mixed disulfides with other thiol compounds; reaction with maleimide, maleic anhydride or other substituted maleimide; formation of mercurial derivatives using 4-chloromercuribenzoate, 4-chloromercuriphenylsulfonic acid, phenylmercury chloride, 2-chloromercuric-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids.

Crosslinkers can be used, for example, to stabilize 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides could be conformationally constrained by, for example, incorporation of C and N α-methylamino acids, introduction of double bonds between C and C atoms of amino acids and the formation of cyclic peptides or analogs by introducing covalent bonds such as forming an amide bond between the N and C termini, between two side chains or between a side chain and the N or C terminus.

The peptides of the invention or their analogs may be of single length or in tandem or multiple repeats. A single type of peptide or analog may form the repeats or the repeats may be composed of different peptides including suitable carrier molecules.

The present invention, therefore, extends to peptides or polypeptides and amino acid and/or chemical analogs thereof corresponding to regions of the RGD domain, Factor X domains, C3bi domain, or the CRD of FHA.

The utilities, as well as the means to achieve these utilities, which may be realized from the recognition that FHA, C3bi, Factor X and the integrin receptors on endothelial cells are structurally and functionally related will now be described in greater detail.

1. FHA and peptides which contain or mimic the RGD region of FHA or the Factor X or C3bi regions of FHA will bind to integrins of leukocytes to inhibit the inflammatory process.

Leukocytes, such as monocytes, and polymorphonuclear leukocytes (PMN), circulate in the blood and normally do not adhere to the endothelium. Upon the introduction into the tissue of (1) an infectious agent, (2) fragments that result from the death of an infectious agent, or (3) another inflammatory substance, leukocytes, such as PMN, are induced to bind to the endothelium and then migrate into the tissues. This is a two step process in which the leukocyte initially binds to receptors on the endothelium, such as integrin receptors. One effect of the binding is that the cell junctions between endothelial cells in the endothelium open. This permits the leukocyte, in the second step, to move from the integrin receptor through the junction and into the tissue. Since PMN can recognize and kill many infectious agents, the passage of leukocytes through the endothelium and into the tissue is a protective mechanism. However, in many disease circumstances, leukocytes react in an exaggerated and deleterious fashion. They may bind so avidly to endothelium as to occlude blood flow. Once in the tissues, they secrete proteases, reactive oxygen intermediates, and other toxic molecules which not only kill infectious agents, but also can result in extensive tissue damage. In addition, they trigger release of inflammatory mediators that alter vascular tone and permeability, and that recruit additional leukocytes to the site, thus perpetuating the inflammatory response.

As stated above, FHA binds to CR3 leukocytes through three domains, namely, the RGD region, Factor X-like regions and the C3bi-like region, for which the integrin on the leukocyte surface acts as a receptor. When it does so, it prevents the leukocytes from using the integrins to adhere to the endothelium or to provoke an inflammatory process involving such adherence, Factor X binding to leukocytes, or C3bi binding to leukocytes.

The adherence inflammatory process is schematically illustrated for the integrin receptors on endothelial cells in FIG. 4. The Figure shows a portion of the endothelium constructed from adjacent endothelial cells with apposed cell junctions. The sketch shows leukocytes in the blood stream together with FHA or segments thereof.

The left side of the Figure illustrates the normal adhesive reaction between an integrin such as CR3 on a leukocyte and integrin receptors such as a RGD or RGD mimicking region of the endothelial cells that form the endothelium. The result of the reaction, as shown by the arrow, is that a cell junction opens and the leukocyte moves from the RGD region into the tissue.

The right side of the sketch shows that the presence of FHA or peptides acting like FHA in the blood stream prevents this reaction because they react with the integrin and prevent it from binding to the integrin receptors. This has the effect of preventing the interaction of the integrin receptors and the leukocyte integrin so that the leukocyte cannot pass through the endothelium into the tissue.

The agent which will achieve this desirable result can be native FHA or a segment thereof. Typically, it will be a relatively low molecular weight peptide containing one of two motifs; 1) an RGD region or an RGD mimicking region or 2) a Factor X-like region. It may contain, for example from about 5 to 20 amino acid residues or even more. One example of such a peptide is described by Relman et al in the Cell article cited above. It is Thr-Val-Gly-Arg-Gly-Asp-Pro-His-Gln (SEQ ID NO: 15). Other examples are shown in FIG. 2 and Examples 9–11. FIG. 5 illustrates that such an intravenous administration of FHA in an experimental model of meningitis decreases inflammation as evidenced by lower numbers of leukocytes in the cerebrospinal fluid.

The infected tissue which is the target of the present invention can likewise be tissue in any body site susceptible to inflammation caused by the above-described infective agents. The method of the present invention is, however, particularly adaptable to the treatment of infected tissue of the central nervous system, lung, kidney, joints, endocardium, eyes and ears, with the treatment of the cerebrospinal fluid and articular fluid being highly preferred embodiments.

One particularly susceptible tissue for which the present invention is uniquely suited is the tissue of the central nervous system. The vascular endothelium in the brain is morphologically different from that in other tissues in that the endothelial cells there are joined by tight junctions thereby creating a blood-brain barrier which normally prevents molecules the size of proteins from passing from blood into the cerebrospinal fluid.

Additionally, the ingress of leukocytes into articular fluid can be prevented by administration of a therapeutic amount of a selected peptide of the present invention. In cases where the inflammatory reaction of an infection occurs at the joints, e.g. arthritis, this method can be utilized to alleviate the inflammation by preventing the ingress of leukocytes into the articular fluid.

The process of this invention is useful in the control of inflammation arising from substantially any source including, for example, autoimmune disease.

A further method of the present invention is that of reducing or eliminating inflammation in an infectious disease caused by the administration of an anti-infective agent for that disease. This method comprises the simultaneous administration of an effective amount of an anti-infective agent, such as an antibiotic, and an effective amount of a peptide or an active fragment thereof of the present invention to a patient in need of such therapy.

The term "simultaneous administration" as used herein means that therapeutic amounts of the anti-infective agent and the peptide are administered within a time period where their respective effects overlap. Thus, the anti-infective agent may be administered at the same time or before or after the antibody.

Reduction or elimination of inflammation in infectious diseases results in a diminution of the neurological damage that usually accompanies such infections. Since the peptides of this invention possess the unique ability to block movement of leukocytes across the blood-brain barrier, they are uniquely suited to treat infections where the causative infective agent is *Haemophilus influenza* B, *N. meningitidis* b, or a pneumococci such as *Streptococcus pneumoniae*. Such infections are generally treated with an aminoglycoside such as gentamicin or a beta-lactam antibiotic such as a penicillin or cephalosporin. The simultaneous administration of such an anti-infective agent and a peptide or active fragment thereof of the present invention will prevent the deterious neurological effects that can accompany the use of these anti-infective agents.

Figure 5:
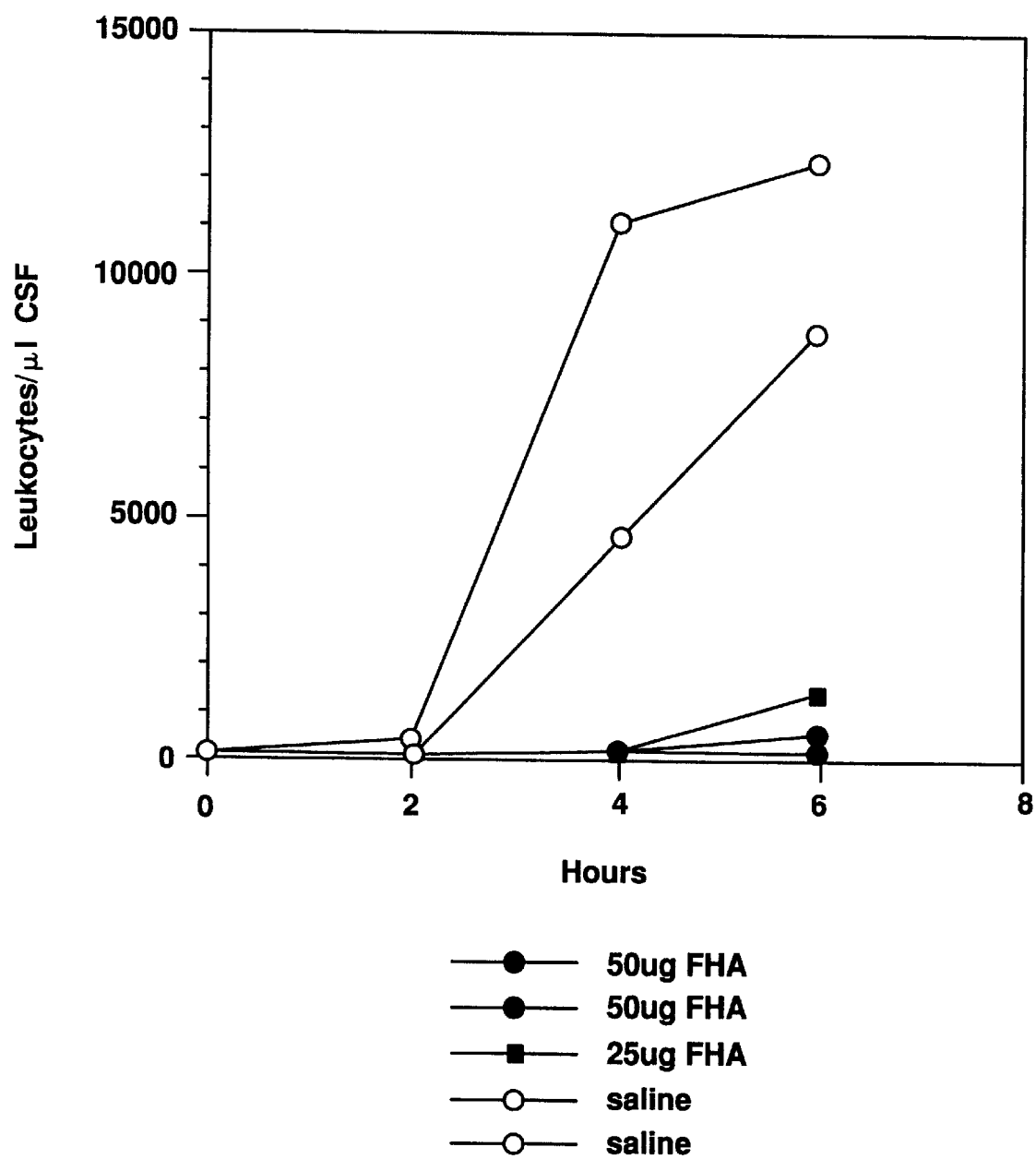
Figure 6:
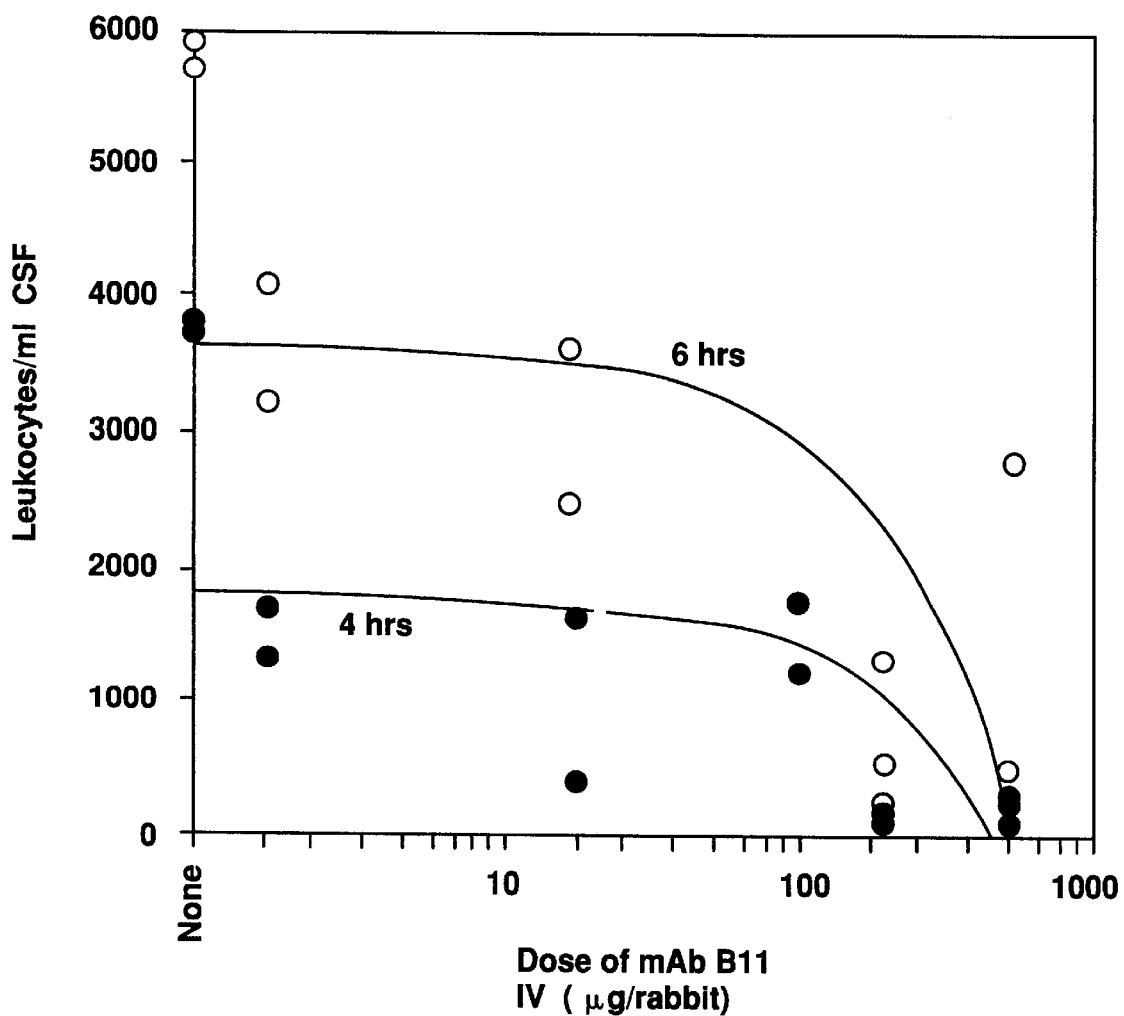

Due to the ability of FHA or active fragment thereof to reduce or eliminate an inflammatory response ancillary to an infectious disease caused by the administration of an anti-infective agent, FHA or active fragment thereof can be combined in a single unit dosage form with the anti-infective agent for convenience of administration. Such dosage form is most preferably an intravenous dosage form since most anti-infective agents, particularly the beta-lactam antibiotics, are available in a suitable chemical form for administration via the intravenous route. This is also the preferred route of administration for FHA or its peptides of the invention. Typically, the anti-infective agent and one or more FHA peptides can be combined in a single ampoule solution. Where this is not possible, the anti-infective agent and the peptide can be packaged separately and mixed just prior to injection. Administration can likewise be via a mixture with any standard intravenous solution, i.e., normal saline.

The amount of anti-infective agent in the dosage form is dependent upon the particular anti-infective agent being utilized and the particular infection being treated. The amount of the peptide utilized in dosage form can range from about 1 to about 1,000 mg, with 10–100 mg per dosage unit being highly preferred. Dosages can be administered one to four times daily, with continued therapy for as long as the infection persists.

This process is also applicable to targeting therapeutic agents to leukocytes. The desired therapeutic agent, for example an anti-leukemic agent, an immunomodulator or other known drug, may be bonded to a selected peptide of the present invention by any selected process, and it will be carried to the leukocyte by the peptide because the peptide binds to the CR3 integrin. The CR3 integrin is restricted to leukocytes and thus limits distribution of such peptide linked agents to leukocytes. Furthermore, ligands bound to the CR3 integrin initiate ingestion of the ligand so the peptide-linked agent can thereby be delivered to and then taken up by the leukocyte.

In another aspect of the present invention, FHA and peptides of FHA which mimic the Factor X or C3bi regions of FHA can be administered to individuals for the purpose of blocking or inhibiting the binding of Factor X or C3bi, respectively, to leukocytes, thereby diminishing the inflammatory response such binding invokes. Peptides from Factor X and C3bi can also be used for the same purpose. Examples of such peptides can be found in Examples 9, 10 and 12. The routes of administration and dosages for these peptides are the same as described supra. The administration of FHA, peptides of FHA which have binding characteristics similar to those of Factor X and C3bi for the CR3 integrin, peptides of Factor X and peptides of C3bi of the present invention will inhibit the coagulation cascade or opsonization from occurring. This will lessen the inflammatory response associated with such phenomena.

2. Antibodies to FHA may be employed to block inflammation or induce blood brain barrier permeability.

Since FHA contains domains that resemble integrin binding regions of C3bi, Factor X and an integrin receptor on endothelial cells, antibodies can be produced against FHA which bind to these natural molecules and thereby disturb their function. The description pertaining to antibodies binding to C3bi is reported in section 4. This section will describe two phenomena:

2a) Antibodies to Factor X-like domains block leukocyte recruitment, the preferred antibodies being 12.1B11 or monoclonal antibodies with binding characteristics substantially similar to that of 12.1B11.

2b) Antibodies to the RGD region bind to endothelial cells and enhance permeability of the blood brain barrier, the preferred antibodies being 13.6E2 or monoclonal antibodies with binding characteristics substantially similar to that of 13.6E2.

2a) Antibodies to FHA which block leukocyte recruitment, e.g.. 12.1B11 or monoclonal antibodies with substantially similar binding characteristics.

During an inflammatory process, the coagulation cascade is activated by the expression of coagulation factors on the surface of an endothelium. This leads to a net pro-coagulant state at the endothelial surface and promotes the deposition of fibrin and clotting. These processes result in the localized thrombotic events characteristic of advanced inflammation and contribute to tissue damage by occluding blood flow which leads to tissue anoxia. Factor X is a coagulation cascade component which interacts with CR3 on leukocytes to promote the association of leukocytes with cells which harbor procoagulant proteins on their surface, such as an endothelium. Factor X has three regions which bind to CR3 as shown by the ability of three peptides to competitively inhibit the binding of CR3 bearing tissue culture cells to purified Factor X. These three peptides are GYDTKQEDG (366–373) (SEQ ID NO: 11), IDRSMKTRG (422 to 430) (SEQ ID NO: 2) and GLYQAKRFKVG (238–246) (SEQ ID NO: 3) as described by Altieri et al., *Science*, supra. FHA contains four regions of significant sequence similarity to these regions of Factor X. They are shown in FIG. 2B (SEQ ID NO: 7 to SEQ ID NO: 10).

FHA has antiinflammatory activity in the sense of inhibiting leukocyte migration into the CSF as documented in FIG. 5. This inhibitory activity implies that antibodies to FHA which bind to any of the three Factor X regions would disturb leukocyte recruitment. This is to be distinguished from anti-FHA antibodies that bind to endothelia by recognizing an integrin receptor which is an endothelial cell component (see below). In the case of anti-FHA antibodies which bind to the Factor X-like regions, the antibodies do not bind directly to endothelial cell components but rather to the coagulation components such as Factor X which may be captured on the endothelial cells during inflammation. This is illustrated by the activity of anti-FHA antibody 12.1B11 which binds to capillaries sporadically (see Example 2) but is highly antiinflammatory when administered intravenously into rabbits with meningitis. This is shown in FIG. 6 where various doses of antibody were given to rabbits and the number of leukocytes recruited into the cerebrospinal fluid in response to pneumonoccal meningitis was determined. Those animals receiving even low doses of antibody 12.1B11 showed inhibition of leukocyte accumulation in cerebrospinal fluid.

2b) Antibodies to the RGD region bind to endothelial cells and enhance blood brain barrier permeability.

The antibodies of this aspect of the invention bind to FHA at the RGD region. These antibodies bind to endothelial cells including those of the blood brain barrier (BBB) and facilitate the passage of water soluble molecules including, for example, therapeutic agents through the BBB and into the cerebrospinal fluid (CSF).

The anti-FHA antibodies of this aspect of the invention apparently bind to molecules on capillary endothelial cells known as endothelial cell (EC) ligands (to distinguish them from the FHA receptors found on leukocytes). These EC ligands have determinants that are exposed on the vascular surface of the endothelial cells. This feature is inferred from the ability of intravenously administered anti-FHA antibodies to bind to vessels as measured immunohistochemically. These EC ligand determinants do not require stimulation by cytokines in order to be expressed or incorporated on the vascular surface of capillary endothelial cells. Antibodies to ICAM-1 do not appear to bind to these EC ligands. Immune blot analysis of the proteins from purified human cerebral microvessels with anti-FHA antibodies indicates that these antibodies bind to two novel polypeptides of apparent molecular size of 64 and 52 kilodaltons.

When the anti-FHA antibody binds to EC ligands, an apparently transient opening of the BBB to therapeutic agents results. That is, in response to intravenous administration of these anti-FHA antibodies, the penetration of therapeutic agents into the brain is enhanced in a time dependent and reversible manner. In addition, binding of intravenously administered anti-FHA antibodies to EC ligands results in an inhibition of leukocyte diapedesis into the brain even though the BBB permeability to therapeutic agents is increased as a result of such binding.

It is a particular advantage of the invention that certain antibodies within its scope permit such passage without concurrent penetration of leukocytes into brain or cerebrospinal fluid (CSF).

The BBB is a continuous boundary between the blood and both the interstitial fluid (IF) and the CSF of the brain. It is composed of a layer of endothelial cells, the cerebral capillary endothelium, that serves as an effective barrier against the entry into the brain's tissue of serum components of both high and low molecular sizes. The restriction against entry of such substances into the brain and the CSF is due to the structure of the cerebral capillary endothelium in which the anatomically tight junctions seal spaces between adjacent endothelial cells.

In a normal (healthy) state, the only substances capable of traversing the BBB to enter the CSF tend to be relatively hydrophobic (lipid-like) molecules or molecules that have specific complementary receptors and active transport systems on the BBB endothelial cells. Thus, substances which are hydrophilic (water-soluble) penetrate the BBB much less effectively or not at all. Such water-soluble and poorly penetrating substances encompass a whole range of molecules extending from molecules as large as albumin to ions as small as sodium. The poor permeability of BBB by many potentially useful hydrophilic substances which can act in a therapeutic or diagnostic manner poses a severe limitation on the treatment of diseases of the brain tissue and CSF. It is therefore of paramount clinical significance to develop products and methods which can "open" the BBB and allow access to the brain tissues and CSF by agents which are known to be effective in treating or diagnosing brain disorders but which, on their own, would not be able to traverse the BBB. Certain antibodies of this invention will achieve that end.

This invention provides a method for increasing the permeability of the blood-brain barrier of a host to a molecule present in the host's bloodstream. The host can be any animal which possesses a central nervous system (i.e., a brain). Examples of hosts include mammals, such as humans and domestic animals (e.g., dog, cat, cow or horse), as well as animals intended for experimental purposes (e.g., mice, rats, rabbits).

The molecule present in the host's bloodstream can be initially exogenous to the host. For example, it can be a neuropharmaceutical agent which has a therapeutic or prophylactic effect on a neurological disorder. Examples of such neurological disorders include cancer (e.g., brain tumors), Acquired Immune Deficiency Syndrome (AIDS), epilepsy, Parkinson's disease, multiple sclerosis, neurodegenerative disease, trauma, depression, Alzheimer's disease, migraine, pain, or a seizure disorder.

Classes of neuropharmaceutical agents which can be used in this invention include antibiotics, adrenergic agents, anticonvulsants, nucleotide analogs, chemotherapeutic agents, anti-trauma agents and other classes of agents used to treat or prevent a neurological disorder. Examples of antibiotics include amphotericin B, gentamycin sulfate, pyrimethamine and penicillin. Examples of adrenergic agents (including blockers) include dopamine and atenolol. Examples of chemotherapeutic agents include adriamycin, methotrexate, cyclophosphamide, etoposide, carboplatin and cisplatin. An example of an anticonvulsant which can be used is valproate and an anti-trauma agent which can be used is superoxide dismutase. Nucleotide analogs which can be used include azido thymidine (AZT), dideoxy inosine (ddI) and dideoxy cytodine (ddC).

The molecule in the host's bloodstream can also be diagnostic imaging or contrast agents. Examples of diagnostic agents include substances that are labelled with radioactivity, such as 99-Tc glucoheptonate.

The administration of the exogenous molecules and/or antibody to FHA to the host's bloodstream can be achieved parenterally by subcutaneous, intravenous or intramuscular injection or by absorption through a bodily tissue, such as the digestive tract, the respiratory system or the skin. The form in which the molecule is administered (e.g., capsule, tablet, solution, emulsion) will depend, at least in part, on the route by which it is administered.

The administration of the exogenous molecule to the host's bloodstream and the administration of antibody to FHA can occur simultaneously or sequentially in time. For example, a therapeutic drug can be administered orally in tablet form while the intravenous administration of the antibody is given 30 minutes later. This is to allow time for the drug to be absorbed in the gastrointestinal tract and taken up by the bloodstream before the antibody is given to increase the permeability of the blood-brain barrier to the drug. On the other hand, the antibody can be administered before or at the same time as an intravenous injection of the drug. Thus, the term "co-administration" is used herein to mean that the blood-brain barrier permeabilizing antibody and the exogenous molecule will be administered at times that will achieve significant concentrations of each substance in the blood for producing the simultaneous effects of increasing the permeability of the blood-brain barrier and allowing the maximum passage of the exogenous molecule from the blood to the cells of the central nervous system.

Figure 7:
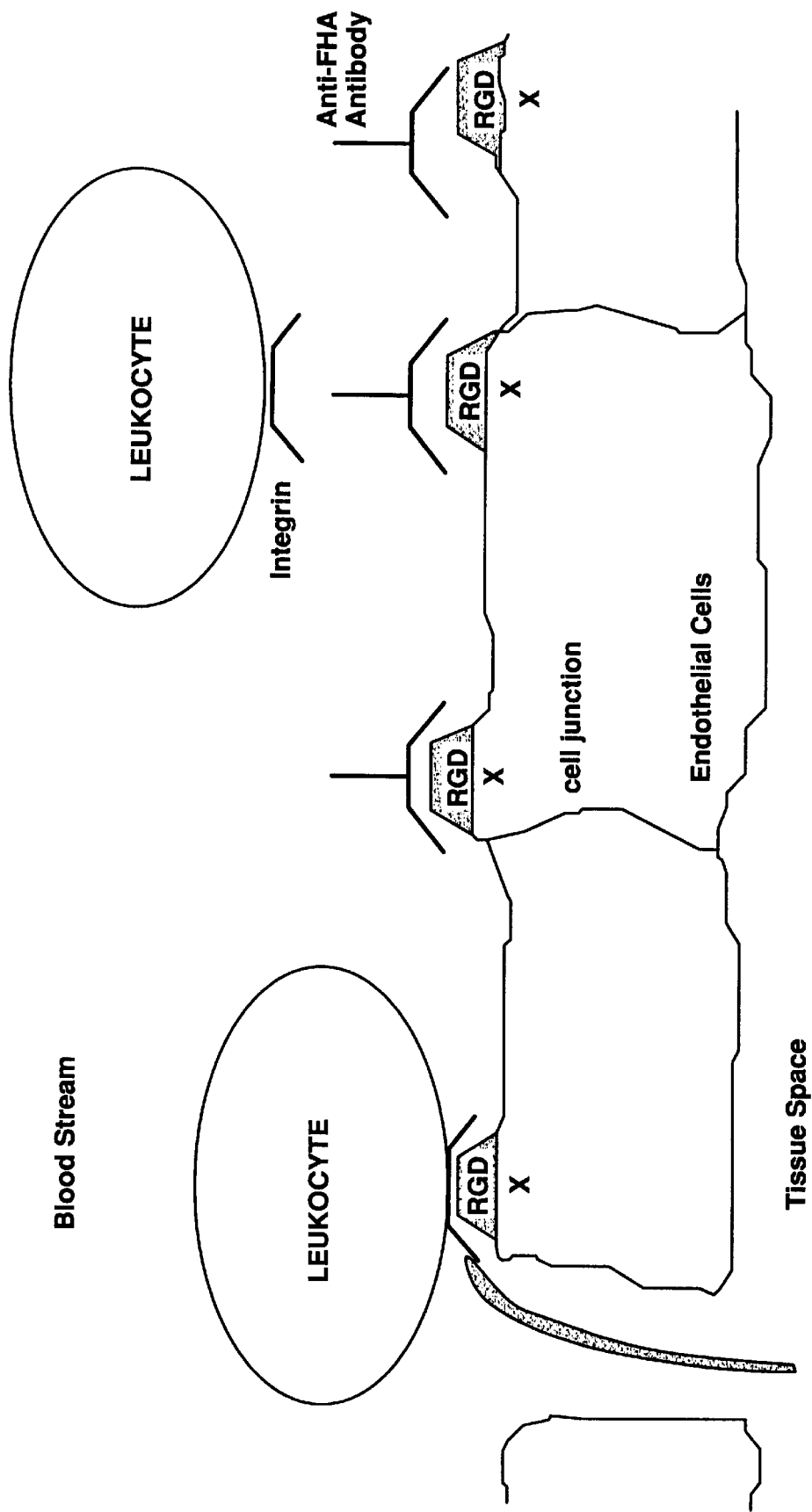
FIGS. 7 and 8 illustrate the use of antibodies to FHA to enhance vascular permeability.
Figure 8:
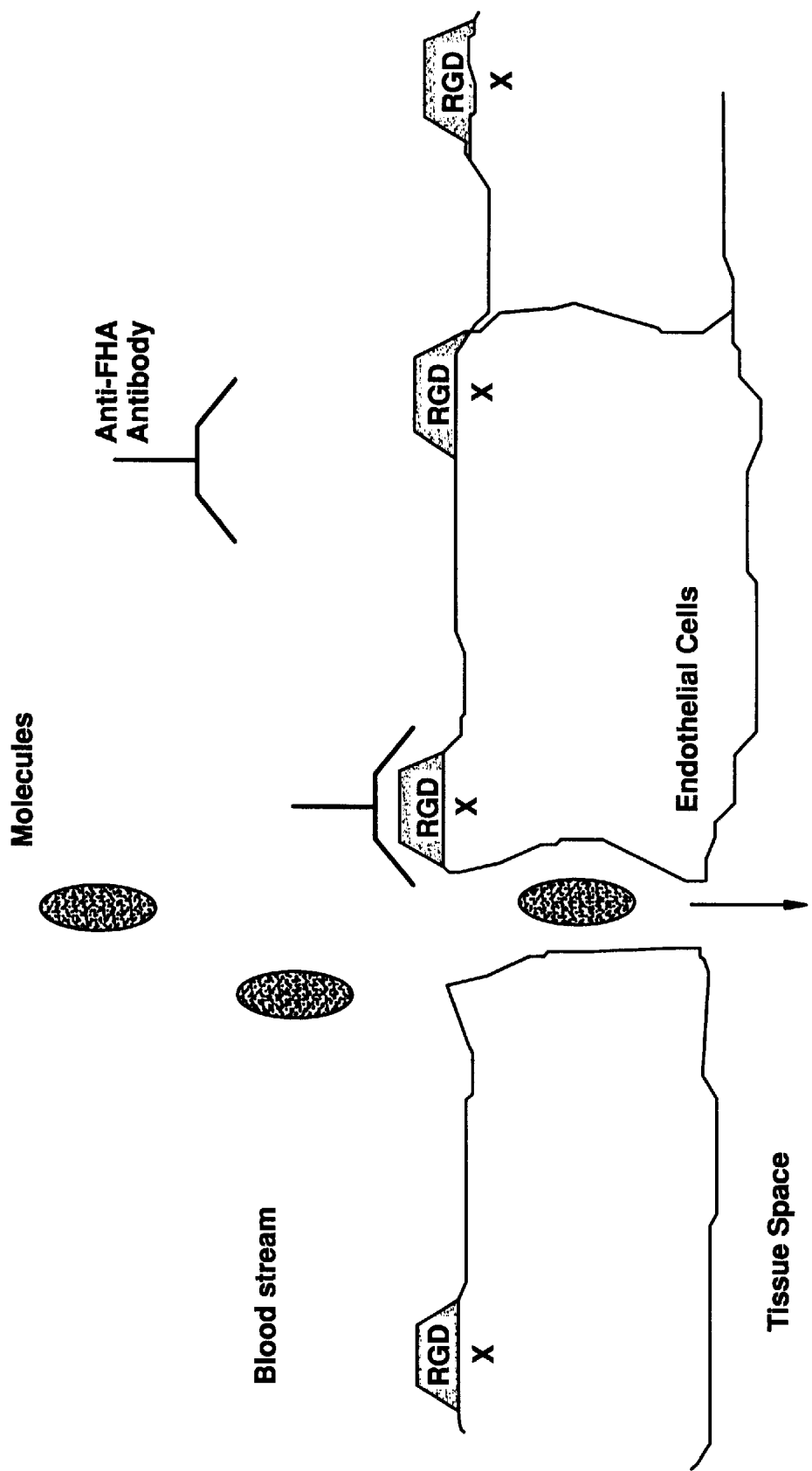

FIGS. 7 and 8 illustrate the process by which the antibodies of this invention will enhance permeability of the BBB to therapeutic agents, particularly to water soluble therapeutic agents. The term "therapeutic agents" is used herein as a convenient term to define all of the various materials which a physician or veterinarian will wish to pass through the BBB into the CSF or the brain. It includes, for example, anti-infective agents such as antibiotics, antineoplastic agents, diagnostic agents, imaging agents, and immuno-suppressive agents, nerve or glial growth factors and other such products.

FIG. 7 shows anti-FHA antibodies in the blood stream adhering to and blocking sites such as the RGD region in the integrin receptors of endothelial cells. By analogy to the first above step in passage of leukocytes through the endothelia described in Item 1, the blocking of the integrin receptors has the effect of opening the cell junctions as shown to the left of the Figure. The cell junctions, however, are not open to leukocytes because, as explained above, in order to pass through the opening in the cell wall, a leukocyte must first adhere to the cell by reaction with the integrin receptors. The leukocyte is prevented from so doing because the integrin receptors are blocked by the anti-FHA antibody. FIG. 8 shows that in the example of FIG. 7, other molecules, e.g., the water-soluble therapeutic agents described above, can pass through the open junctions.

The antibodies of this aspect of the invention can also be used in screening procedures to identify the EC ligands, themselves, that are involved in the transient opening of the BBB. The screening procedures are effective by virtue of the binding specificity of these antibodies. If the EC ligands and integrin receptors are identical, these antibodies are useful in identifying the integrin receptors on the endothelial cells. The identification and isolation of the EC ligands allows further antibodies to be produced, by appropriate immunization procedures known in the art, which are effective in selectively opening the BBB in a transient fashion. The antibodies of this aspect of the invention, in a similar fashion, can be used to identify the EC ligands, themselves, that are involved in the inhibition of leukocyte diapedesis when the antibodies bind to the endothelial cells. The two sets of EC ligands may be identical.

The antibodies of the invention can also serve as carriers for targeting therapeutic agents to endothelial cells in mammals. For this purpose, the therapeutic agent is chemically bonded to the antibody and the combined product administered to the patient in need of such treatment. These therapeutic agents include, for example, coagulation cascade modifiers or immunomodulators such as cytokines. They may also include immunotoxins such as Pseudomonas exotoxin A or ricin attached to an anti-FHA antibody of the invention to produce products capable of killing tumors supplied by or involving vascular endothelium. Procedures for combining such therapeutic agents with proteins such as antibodies are well known.

In certain patients, a potential problem with the use of a murine anti-FHA monoclonal antibody, such as those employed in this invention exists since the patient may generate an immune response against a murine monoclonal antibody. This effect can be ameliorated or obviated by using only active fragments of the monoclonal antibody so as to minimize the amount of foreign protein injected. Another alternative is to employ genetic engineering techniques to make a chimeric antibody in which the binding region of the murine anti-FHA antibody is combined with the constant regions of human immunoglobin.

3. Peptides consisting of the CRD region of FHA may function as nontoxic vaccines.

Several lines of evidence indicate that a carbohydrate recognition domain (CRD) exists in FHA and that interference with its function by inhibitors or antibodies decreases colonization of the lung by B. pertussis in an animal model. This evidence includes:

a) Inhibition of adherence of B. pertussis to human ciliated cells can be achieved by soluble receptor analogs (lactosamines) or anti-carbohydrate antibodies (anti-Lewis a) (Tuomanen et al., J. Exp. Med. supra).

b) FRA binds to lactosylceramide on thin layer chromatography plates containing ciliary extracts (Tuomanen et al., J. Exp. Med. supra).

c) Lactose and antibody to Lewis a decrease colonization of rabbit lung with virulent B. pertussis (Saukkonen et al., J. Exp. Med. 173:1143–1149).

This CRD has been found to lie between amino acids 1141 and 1279 in the FHA sequence by three kinds of experimental evidence:

1) One monoclonal antibody to FHA, 12.5A9, which binds to this region blocks bacterial adherence to ciliated cells. Monoclonal antibodies to other regions of FHA do not.

2) The DNA sequence from nucleotide position 3674 to 4088 (bounded by XhoI sites) which corresponds to the CRD was amplified by the polymerase chain reaction and ligated into one of the pET expression vectors (Rosenberg et al. (1987), Gene 56, 125–135). Expression of the polypeptide in E. coli utilized the T7 RNA polymerase promoter system (Tabor, S. & Richardson, C. C. (1985), Proc. Natl. Acad. Sci. U.S.A. 82). [$^{35}$S] Methionine labeled protein preparations from cell lysates showed a band at the expected size of 18 kD when run on SDS polyacrylamide gels. Cell lysates containing the expressed protein were overlaid on thin-layer chromatography plates containing glycolipid standards and the binding pattern was compared to that of FHA. The CRD protein bound to these carbohydrates in a pattern similar to FHA, especially in the ability to bind to lactosylceramides. Cell lysates not containing the expressed protein did not bind lactosylceramide.

3) B. Pertussis mutants lacking the CRD region did not bind to ciliated cells or macrophages. Several mutants of B. pertussis were created which produce a truncated form of FHA that lacks the CRD region. A 0.4 kb XhoI—XhoI fragment which encompasses the DNA sequence corresponding to the CRD region was deleted from the gene for FHA thus creating an inframe deletion. This was accomplished genetically with a plasmid vector designed for gene replacement of an unmarked allele. Mutants were created in either a wild type (BP536) or ptx-(BP Tox6) background. Colony immunoblots of bacteria containing the truncated FHA gene do not react with monoclonal antibody 12.5A9 which is specific for the CRD. Antibody binding was determined by standard procedures. The results of antibody 12.5A9 binding to various B pertussis strains are shown in Table 1.

TABLE 1

Reactivity of Anti-CRD Region Antibody with B. Pertussis Strains

| Strain | Description | Stain |
| --- | --- | --- |
| BPS36 | Parent | ++++ |
| BP537 | bvg-, does not produce FHA | |
| BP101 | contains an inframe deletion of the RGD well as the A region | +/-- |
| Mutants | XhoI-XhoI deletions | --or +/-- |

A truncated form of FHA was readily detected by Western blot analysis of culture supernatants from the mutant strains of B. pertussis. The FHA from these strains migrated with a slightly smaller apparent molecular weight than whole FHA. The truncated form of FHA did not cross react with monoclonal antibody 12.5A9 to the CRD but did cross react with monoclonal antibody 12.6F8 to another separate and distant region of FHA. These mutants also produced the same amount of FHA as the parental strain.

B. pertussis mutants producing the truncated form of FHA failed to bind to macrophages and ciliated cells. The FHA mutants were tested in a ciliated cell adherence assay as described in Tuomanen et al., J. Infec. Dis. supra. Binding for these mutants was not detectable; the parental strain BP536 bound >4 BP/cell.

A second adherence test involved the binding of FHA mutants to macrophages. Approximately $10^7$ fluorescein-labeled bacteria were incubated with $10^6$ macrophages and examined under the microscope for evidence of binding. The mutants bound in the range of 60–80 per 100 macrophages as opposed to the wild type's binding of 300 per 100 macrophages.

These studies indicate the CRD of FHA lies in the amino acid residue region of 1141 to 1279. Taken together with the efficacy of antibodies to the receptor for this region in blocking colonization of the lung in animal models and the efficacy of antibodies to this region in blocking adherence of bacteria to cilia, this region constitutes an immunogen which, in the present invention, can generate antibodies that are effective in protecting against whooping cough.

These immunogens of the present invention have several advantages over current whole cell or FHA-containing vaccines. It is well known that pertussis vaccines are toxic as indicated by reactions such as death and encephalopathy. Vaccines containing the entire FHA molecule engender antibodies which are cross reactive with endothelial cells, C3bi and Factor X. Such cross reactive antibodies will contribute to these toxic reactions. Presentation of a vaccine which contains no toxic epitopes is preferred. Furthermore, generation of antibodies that block adherence, such as the antibodies generated by the CRD as an immunogen, will block colonization of the respiratory tract, a desirable property not characteristic of present vaccines. This vaccine can be formulated by presenting the CRD alone or in combination with other proteins or other segments of FHA which have been chemically or genetically altered to eliminate generation of cross reactive antibodies. Testing for this property will be described below. The preferred peptides for vaccines are shown in FIG. 3 (SEQ ID NO: 11 to SEQ ID NO: 14).

Figure 9:
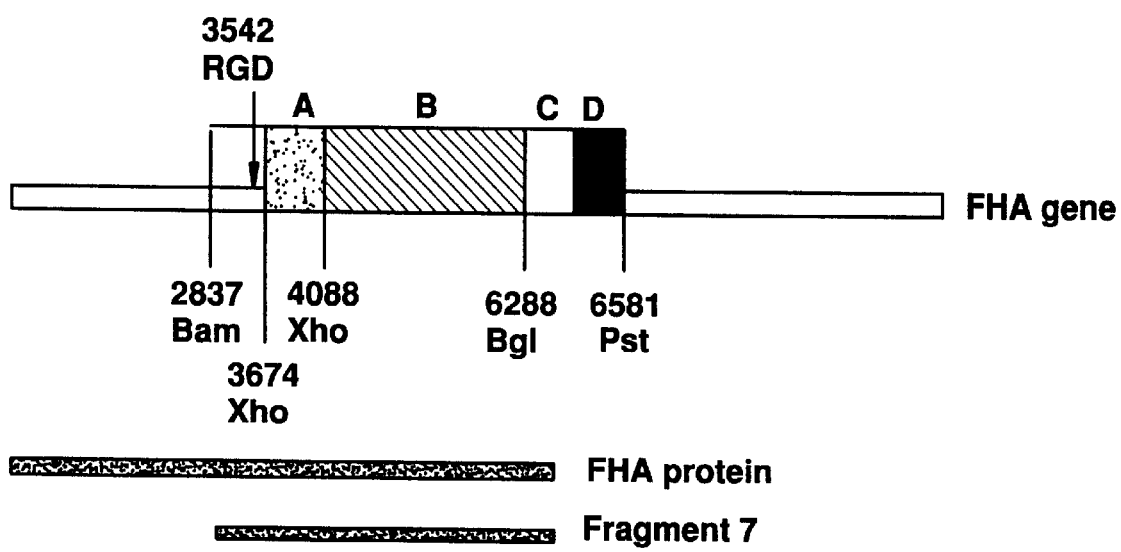
FIG. 9 is a representation of Fragment 7 of FHA as defined by Delisse-Gathoye et al, supra.
Figure 12:
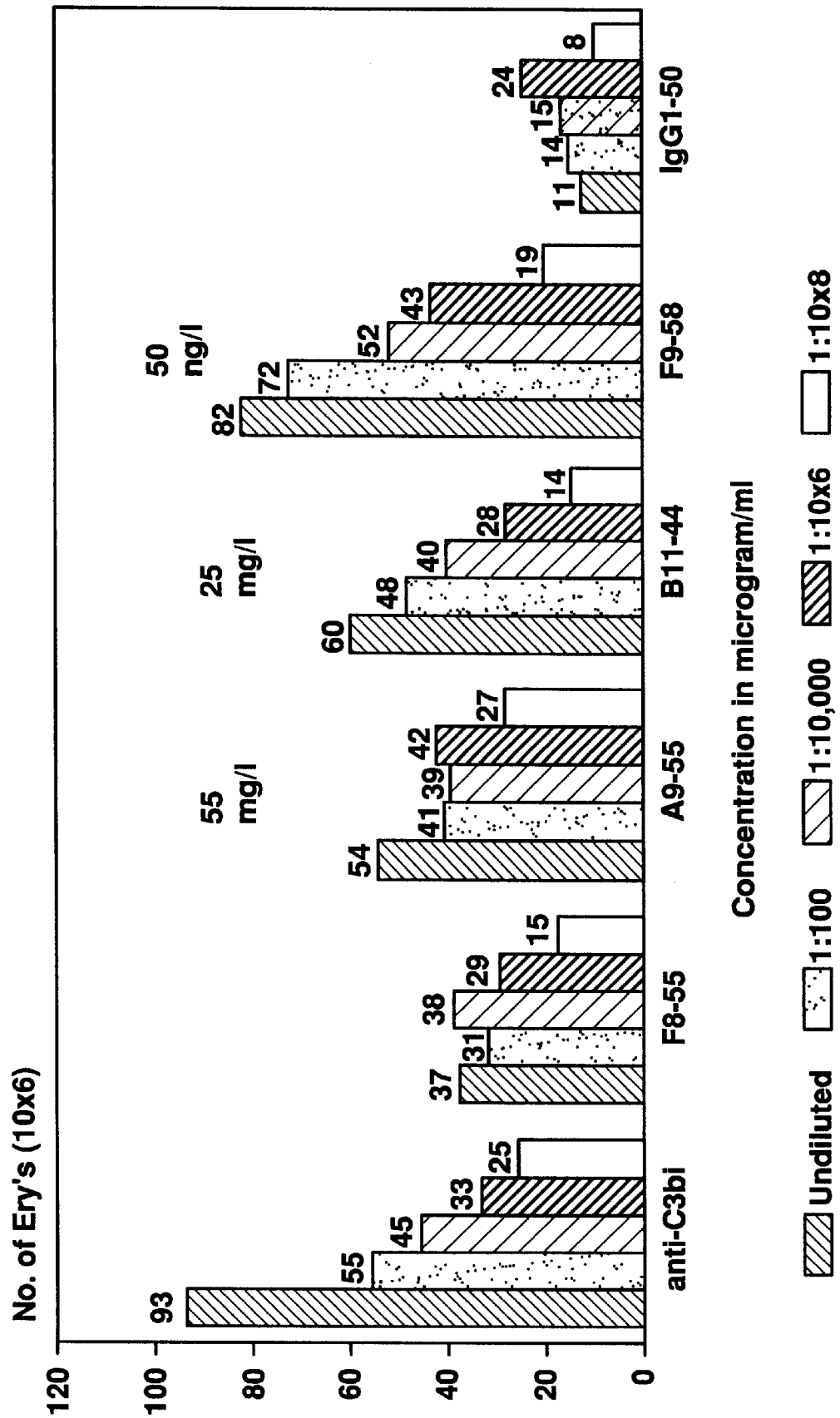
FIG. 12 shows the relative ability of anti-FHA antibodies to bind to C3bi.

Delisse-Gathoye et al., supra have described a number of expression products of the FHA gene. One of them, Fragment 7, is defined by the BamHI site at nucleotide position 2837 and the Pst 1 site at nucleotide position 6581 as shown in FIG. 9 which also shows other segments of the fraction defined by other restriction enzymes. This polynucleotide region (FIGS. 10A–10L) (SEQ ID NO: 16 AND SEQ ID NO: 17) expresses an FHA segment which contains the RGD region at the positions corresponding to amino acid residue positions 1097 to 1099 of FHA. Fragment 7 also contains at least one carbohydrate recognition site. This site lies between amino acid residues 1141 through 1279. The presence of such site is established by the fact that antibodies to Fragment 7 such as 12.5A9 will react with FHA and prevent adherence of FHA to cilia or purified glycoconjugates. The XhoI—XhoI segment of Fragment 7, therefore, will be a suitable peptide for producing a vaccine in accordance with this invention. Smaller segments of this fragment lacking the RGD region but containing carbohydrate recognition regions or amino acid sequences mimicking such regions will also be suitable for producing a vaccine in accordance with the invention. The truncated FHA's which delete the RGD region can be produced genetically as illustrated in FIG. 11 (SEQ ID NO: 18). These segments may be contained in FHA mutants.

Antibodies that block the function of the CRD, such as monoclonal antibody 12.5A9 or antisera generated with CRD vaccine candidates detailed above constitute prophylactic or therapeutic agents for whooping cough. These antibodies when delivered to the respiratory epithelium decrease colonization by interfering with adherence of the bacteria to cilia and by promoting clearance.

4. Detection of Toxic Antibodies elicited by Vaccines.

It will be apparent to the skilled artisan that some of the same antibodies to FHA elicited by conventional vaccines to protect against BP infections as explained in Item 2 above may also: (a) cross-react with the integrin receptors of endothelia thereby to open the endothelia to the passage of serum components, (b) bind complement components such as C3bi so that they are not available to participate in inflammation, or (c) immunoreact with Factor X. These activities might be regarded as toxic reactions for a product intended for use as a vaccine. Accordingly, it is preferred for the production of vaccines to select peptides generating antibodies which will block the carbohydrate dependent interactions of BP with mammalian cells but will not react with integrin receptors and open cell junctions, bind complement components or immunoreact with Factor X. Such peptides will be selected from amongst the peptides of the invention so as to eliminate regions of FHA with binding properties of normal molecules in animals but preserving the carbohydrate recognition site. Examples are shown in FIG. 3 (SEQ ID NO: 11 TO SEQ ID NO: 14).

Figure 2:
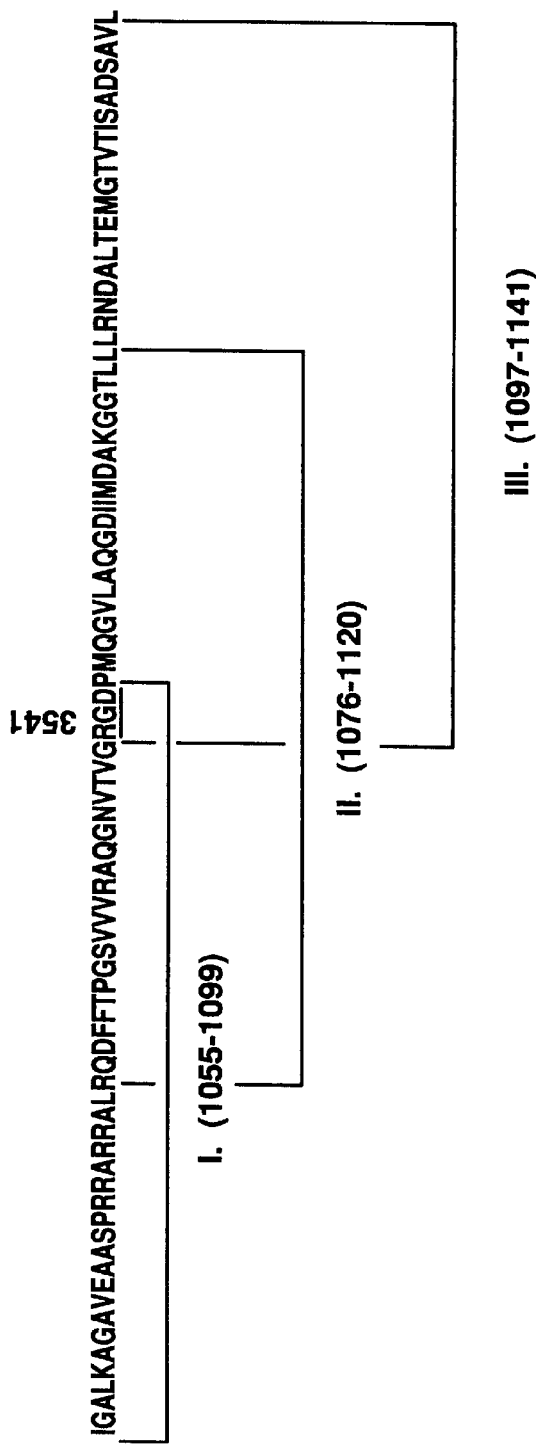
FIGS. 2A and 2B are representative of peptides which will block leukocyte adherence to endothelia or interfere with coagulation.
Figure 4:
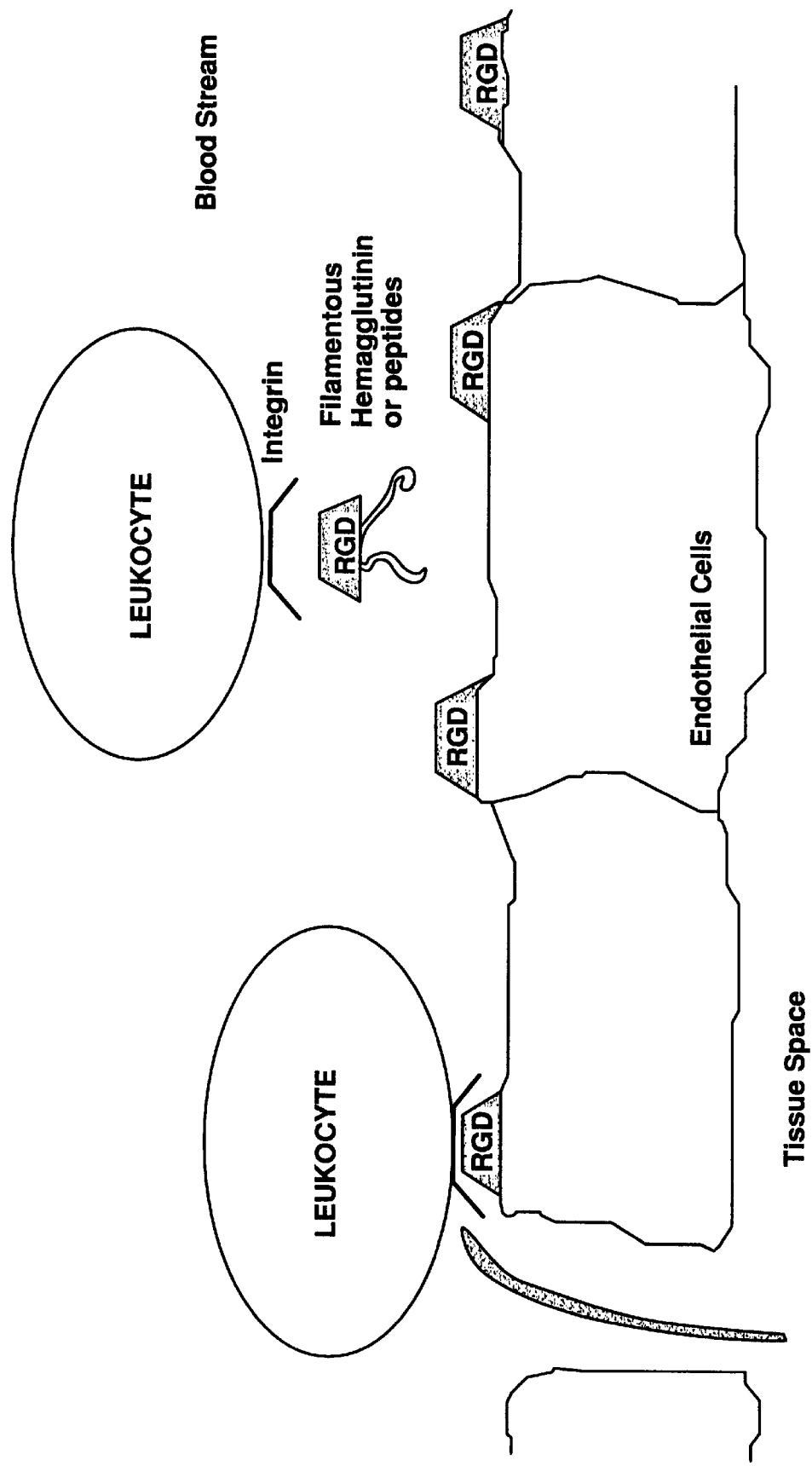
FIGS. 4–6 illustrate the use of FHA, peptides or antibodies of the invention as antiinflammatory agents.

The peptides of this invention, particularly those with binding properties of normal molecules in animals, as listed in FIG. 2 (SEQ ID NO: 4 TO SEQ ID NO: 10) or Region B of FHA will be valuable for quality control procedures in the production of BP vaccines as well as other vaccines, for example antiviral or antibacterial vaccines, to detect components of these vaccines which generate antibodies which crossreact to endothelium, C3bi or Factor X. These peptides may be employed to test for the presence of antigens in vaccines which will generate toxic antibodies. The technique is illustrated in Examples 1 and 2.

To test for such potential toxicity, the candidate vaccine antigen will be employed to immunize an animal such as a rabbit. The antiserum from the immunized animal will be used to overlay human brain tissue slices or another surface coated with an integrin receptor protein containing, for example, RGD or a RGD mimicking peptide, C3bi or Factor X. Binding of the testing antibody to the tissue section or the immobilized peptide indicates that the vaccine antigen produces antibodies which cross react with the integrin receptor, C3bi or Factor X and that the vaccine will be considered to be toxic.

Conversely, the antibodies in a serum to be tested can be bound to a surface of a plate coated with Protein A. Addition of C3bi coated particles will lead to capture of the particles if the serum contains anti C3bi antibodies. Serums with a high capture capacity indicate the toxicity of the vaccine. This test is illustrated in Example 8. Its use with anti-FHA monoclonal antibodies for comparison purposes is shown in FIG. 12.

Any of a variety of tests may be employed to detect the binding of toxic antibodies. Typical tests include radioimmunoassay, enzyme linked immunoassay as well as direct and indirect immunofluorescence. These tests may employ competitive and sandwich type assays. Typically, the tests will employ detectable labels on an indicator antibody. Useful labels include fluorescent labels such as fluorescein, rhodamine or auramine. Radioisotopes such as $^{14}C$, $^{131}I$, $^{125}I$ and $^{35}S$ may be employed. Enzyme labels which may be utilized include, for example, β-D-glucamidase, β-D-glucosidase, β-D-galactosidase, urease, glucose oxidase plus peroxidase, and acid or alkaline phosphatase. Methods for labeling biological products such as cells, antibodies, antigens and antisera are well known and need not be described.

There are several currently available procedures for detecting these labels including, for example calorimetric, spectrophotometric, fluorospectrophotometric, photometric and gasometric techniques, as well as various instrumental methods of detecting isotopes.

All of these tests involve the formation of a detectable reaction product between the indicator antibody and the test toxic antibody which is reactive with the integrin receptor region on endothelial cells, Factor X or C3bi that is generated by an immunological response to a toxic antigen in a vaccine. The indicator antibody, i.e. the labeled antibody, may react directly with the toxic antibody; for example, in an enzyme linked immunoassay procedure (ELISA) or other sandwich type test.

COMPOSITIONS

The products of the invention may be provided as parenteral compositions, for example vaccines, for injection, infusion, or other parenteral procedures. Such compositions comprise a prophylactically effective amount of a selected peptide or antibody and a pharmaceutically acceptable carrier. They can, for example, be suspended in an inert oil, or in alum or other suitable adjuvant. Alternatively, they can be suspended in an aqueous isotonic buffer solution at a pH of about 5.6 to 7.1. Useful buffers include sodium phosphate-phosphoric acid.

The desired isotonicity may be accomplished using sodium chloride or other pharmaceutically acceptable agents such as dextrose, boric acid, sodium tartrate, propylene glycol or other inorganic or organic solutes. Sodium chloride is preferred particularly when buffers containing sodium ions are used.

If desired the solutions may be thickened with a thickening agent such as methyl cellulose. They may be prepared in emulsified form, either water in oil or oil in water. Any of a wide variety of pharmaceutically acceptable emulsifying agents may be employed including, for example acacia powder, or an alkaryl polyether alcohol sulfate or sulfonate such as a Triton.

The therapeutically useful compositions of the invention are prepared by mixing the ingredients following generally accepted procedures. For example, the selected components may be simply mixed in a blender or other standard device to produce a concentrated mixture which may then be adjusted to the final concentration and viscosity by the addition of water or thickening agent and possibly a buffer to control pH or an additional solute to control tonicity.

The dosage and method of administering the peptides of the invention may be varied due to patient condition, the result sought to be achieved and other factors readily evaluated by the attending physician or veterinarian. For example, while the presently preferred method of administering peptides comprising vaccines of the invention is parenteral administration, certain of them will be administered orally in a pharmaceutically acceptable oral carrier. The antigenic peptides thus administered will generate antibodies in the lymph nodes of the intestine. These antibodies will be distributed systemically to produce a prophylactic effect.

The following non-limiting examples are given by way of illustration only.

EXAMPLE 1

Binding of Rabbit and Goat Polyclonal Anti-FHA Antibodies to Cerebral Capillary Endothelia.

Cerebral capillary endothelial cells harvested from rabbit brains or cryostat sections from human brains were mounted onto glass slides in the following manner.

Human brain samples were quick frozen 1–3 hrs post mortem; those of animals were frozen at the time of sacrifice. For preparation of human and animal tissue slices, cerebral cortex was cut in 20$\mu$ sections; for some experiments, rabbit cerebral capillaries were extracted from homogenized tissues by centrifugation in 15% dextran. Capillaries or tissue slices were fixed onto glass slides with acetone at room temperature for 10 min and stored at −80° C. until used. Antisera were diluted into phosphate buffered saline (PBS) at 1:20. Rabbit capillary staining was visualized with a 1:40 dilution of fluoresceinated anti-Fc antibody to the appropriate species (Boehringer Chemical, Indianapolis, Ind.). For tissue slices, the Vector ABC Elite immunohistochemistry kit for peroxidase was used to visualize capillary staining. Brain slices were incubated at room temperature in the following: PBS (10 min), 0.3% peroxide/methanol (30 min), PBS (10 min), 0.25% α-methyl mannoside/0.25% nonfat dry milk in PBS (15 min), PBS (10 min). Primary antibody was then applied either at room temperature for 2 hrs or at 4° C. for 16 hrs. Slices were rinsed for 10 min in PBS and then treated with the following at room temperature: Vector biotinylated secondary antibody (30 min), PBS (10 min), Vector avidin-peroxidase mixture (30 min), PBS (10 min), peroxidase substrate until color was seen (2–7 min). Purified monoclonal antibodies to human or rat transferrin receptor were always used as a positive control and all observed experimental staining was graded with respect to the positive control. Negative controls included goat serum (because the biotinylated anti-rabbit antibodies are made in goat) and horse serum (because the biotinylated anti-rabbit antibodies are made in horse).

Preparations from at least two different individuals were incubated with the antibody at 1:20 dilution (or greater) at room temperature for 2 hrs, rinsed, and incubated for 30 min with either a Vector biotinylated secondary antibody (Vector Elite ABC Immunohistochemistry Kit) for human specimens or a fluoresceinated anti-Fc antibody for rabbit specimens. After rinsing, rabbit specimens were viewed with a fluorescence microscope; for human specimens, the Vector avidin-peroxidase mixture was applied for 30 min, followed by rinsing and application of the substrate. The stained tissue preparations were viewed under a light microscope. (+ indicates detectable staining comparable to control). The results are shown below.

TABLE 2

Cross Reactivity Antibodies to *B. Pertussis* Antigens with Cerebral Capillaries of Mammalian Brain

|  |  | Rabbit | Human |
|---|---|---|---|
| Goat antisera |  |  |  |
|  | to: native purified FHA | + | + |
|  | native purified pertussis toxin | 0 | nd |
| Rabbit antisera |  |  |  |
|  | to: native purified FHA | + | + |
|  | glutaraldehyde-treated FHA | 0 | 0 |
| Human antisera: | pooled cord serum | 0 | 0 |
|  | pre-immune (n = 8) | 0 | 0 |
|  | post-primary DPT (n = 2) | + | + |
|  | post-infection (n = 5) | 3 of 5+ | 3 of 5+ |
|  | post-infection absorbed with BP | 0 | 0 |
|  | pertussis immune globulin (PIG) | + | + |
|  | PIG absorbed with BP | 0 | 0 |
| controls: | anti-human transferrin receptor | nd | + |
|  | rabbit, goat or horse serum | 0 | 0 |

These results demonstrate that rabbit and human antibodies to FHA of *B. pertussis* cross-react respectively with cerebral capillary endothelial cells of these animal species. This indicates that there are regions on FHA and the cerebral capillary endothelial cell surface that are immunologically similar enough to be antigenically recognized by the same ligand.

EXAMPLE 2

Binding of Anti-FHA Antibodies which Recognize the RGD Region of FHA to Cerebral Capillaries.

Monoclonal antibodies were used undiluted as supernatant fluids. Staining of human cerebral capillaries was detected as in Example 1. Each antibody was tested at least two times at 24° C. and at 4° C. Staining of capillaries was accompanied by staining of large vessels. The number of + indicates relative degree of staining; antibodies were tested on samples from at least two humans. nd=not determined. Staining of cultured human umbilical vein endothelial cells was performed using the peroxidase-anti-peroxidase technique Muller et al,. *J. Exp. Med.* 170: 399–404, 1989. The ability of antibodies to bind C3bi was tested in an ELISA assay in which wells were coated with antibodies (10 μg/ml), washed and then incubated for 30 min with erythrocytes coated with C3bi (made as described in Example 8). Captured C3bi-coated erythrocytes were detected visually. The ability of antibodies to block binding of FHA to carbohydrates was performed in an overlay assay as described using glycolipid standards separated by thin layer chromatography (Tuomanen et al., *J. Exp. Med.*, 168:267–277, 1988). The results are shown below.

TABLE 3

Ability of Monoclonal Anti-FHA Antibodies to Cross-React with Endothelium, C3bi and Inhibit Interaction of FHA with Carbohydrates in vitro

|  | Stain Human | | | |
|---|---|---|---|---|
|  | Cerebral Capillaries | Umbilical Vein | Bind C3bi | Inhibit FHA-Carbohydrate |
| Region A |  |  |  |  |
| 13.6E2 | +++ | -- | nd | -- |
| 12.5A9 | -- | -- | + | + |
| 12D1 | -- | -- | nd | + |
| Region B |  |  |  |  |
| 12.1F9 | -- | -- | +++ | -- |
| Region C |  |  |  |  |
| 12.1B11 | + | + | ++ | -- |
| Region D |  |  |  |  |
| 12.6F8 | ++ | + | ++ | -- |
| Other |  |  |  |  |
| G9 | nd | -- | nd | -- |
| A12 | nd | -- | nd | -- |

These results demonstrate that antibodies to different regions of FHA have immunoreactivities which differentially correlate with binding to other identifiable biological features. Particular antibodies to FHA, e.g. mAb 13.6E2, recognize cerebral capillary endothelial cells but not the region of FHA that recognizes carbohydrates (which, conversely, is particularly recognized by other monoclonal antibodies, e.g. mAb 12.5A9 and 12D1. In addition, particular antibodies, such as mAb 13.6E2, have further preferred affinity for cerebral vessels as opposed to peripheral vessels as exemplified by umbilical vein endothelial cells. Other particular antibodies to FHA recognize C3bi but not cerebral capillary endothelial cells or umbilical vein cells nor the region of FHA that recognizes carbohydrates. Still other particular antibodies to FHA recognize more than one of these biological features. These results indicate that FHA contains immunologically recognizable regions that are uniquely cross-reactive with other biological features such as brain capillary endothelial cells or C3bi.

EXAMPLE 3

Blocking of Influx of Leukocytes into Rabbit Cerebrospinal Fluid by Intravenous Administration of Antibody to FHA Rabbits were inoculated intracisternally with $10^8$ pneumococci and the generation of an inflammatory response in cerebrospinal fluid (CSF) was followed over time by measuring the appearance of leukocytes and protein in CSF. Animals were treated with the antibodies intravenously (2 mg/kg of culture supernatant fluid) at the same time as the intracisternal challenge was given. The results are shown in Table 4.

TABLE 4

Inhibition of Leukocyte Influx into
CSF by Administering an Anti-FHA Antibody

|  | Leukocyte Number* (x 10³/ml CSF) | | | Protein** (mg/dl) | |
| --- | --- | --- | --- | --- | --- |
|  | 0 | 4 | 5 hrs | 4 | 6 hrs |
| no antibody | 112 | 3661 | 6538 | 1.9 | 2.2 |
| TnAb 13.6E2 |  |  |  |  |  |
| (rabbit A) | 162 | 1452+ | 3322+ | 2.9 | 3.3 |
| (rabbit B) | 95 | 1024+ | 2413+ | 1.4 | 3.1 |
| (rabbit C) | 111 | 1098+ | 4435 | 1.4 | 1.8 |
| anti-pertussis toxin |  |  |  |  |  |
| control Ab | 119 | 3641 | 6245 | 2.3 | 2.8 |

*normal = 120;
**normal = 1.0
+significantly different from control

These results are interpreted to show that intravenous anti-FHA mAB 13.6E2 significantly decreases the influx of leukocytes into CSF of rabbits challenged with an inflammatory amount of pneumococci. Antibody to pertussis toxin does not. Accumulation of protein in CSF was augmented in antibody treated animals indicating increased blood brain barrier permeability. This latter observation is consistent with Example 4.

EXAMPLE 4

Permeability Enhancement of the Cerebral
Capillary Endothelium by Intravenous
Administration of Antibody to FHA Rabbits were injected intravenously with antibodies and the influx of protein into the CSF was followed over time. Such influx occurs only when the permeability of the cerebral capillary endothelium is enhanced. As shown in Example 3, such protein influx was enhanced during the inflammatory response to bacterial products in CSF in antibody treated animals. In this example, this activity was demonstrated in the absence of an inflammatory stimulus as shown in Table 5.

TABLE 5

Enhancement of Cerebral Permeability to
Protein by Administering an Anti-FHA Antibody

|  |  | Protein (mg/dl) | |
| --- | --- | --- | --- |
|  |  | 4 | 6 hrs |
| no antibody |  | 0.8 | 0.8 |
| mAb 13.6E2 | (rabbit A) | 2.2 | 3.7 |
|  | (rabbit B) | 2.0 | 1.8 |
|  | (rabbit C) | 1.4 | 1.8 |
| polyclonal anti FHA Ab |  | 1.2 | 1.2 |

These results are interpreted to show that anti-FHA antibodies, particularly the monoclonal antibody 13.6E2, enhance the permeability of cerebral capillary endothelia sufficiently to allow passage of serum proteins into CSF. This permeability enhancement is evident at least as early as 4 hours after the anti-FHA antibodies are administered.

EXAMPLE 5

Figure 13:
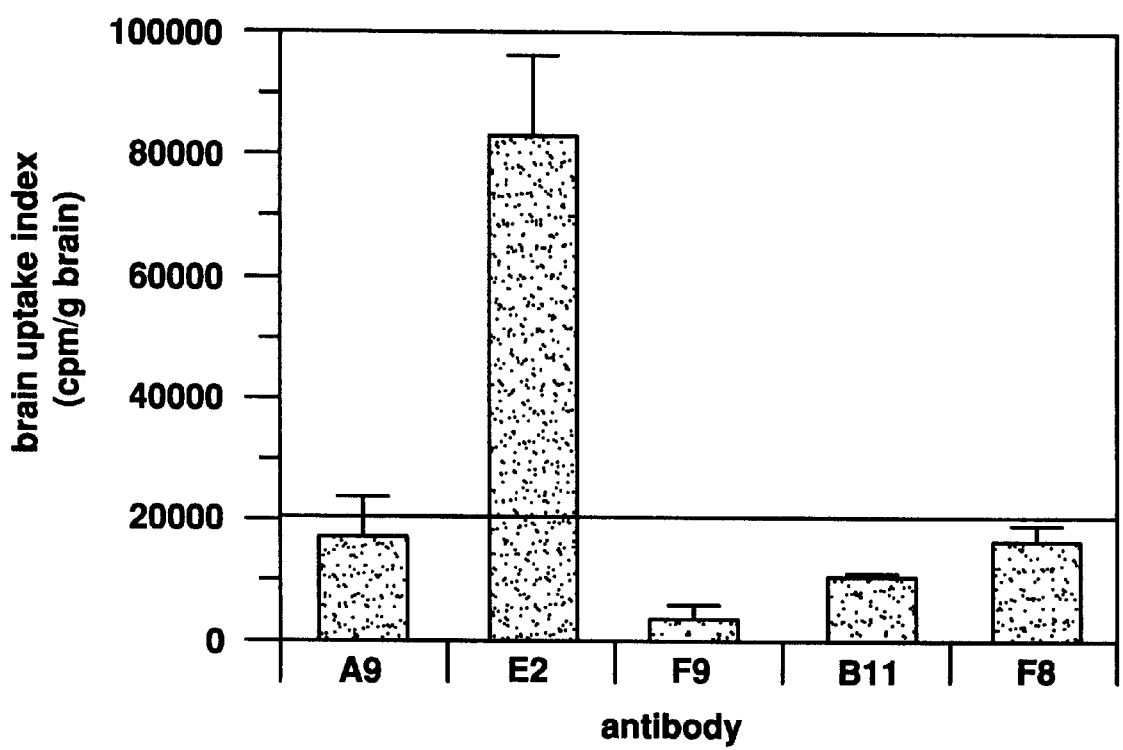
FIGS. 13 and 14A and 14B refer to Examples 5 and 6 respectively.

Penetration Enhancement of [³H] Penicillin from
Serum to Brain by Intravenous Administration of
Antibodies to FHA Rabbits (n=at least 2 per condition) were injected with the selected antibodies identified in Example 2 (10 µg/kg) intravenously; 4 hours later, ³H penicillin (1.04 mCu/50 µg/rabbit; Merck, Sharp and Dohme, Rahway, N.J.) was injected intravenously and after 30 min, blood and brain harvested. Approximately one gram of right parietal cortex was excised, weighed, homogenized, solubilized with Soluene 350 (Packard, Boston, Mass.), and ³H cpm in brain and serum samples were counted. Blood volume per gram of brain was determined to be 300±73 µl from a set of 6 saline-treated control animals. A brain uptake index indicates the amount of radiolabel in brain tissue after subtraction of values from blood (BUI=cpm per gram brain homogenate—[cpm per µl blood×300 µl blood/gram homogenate]). Results are shown in FIG. 13. The horizontal line indicates the maximum uptake observed in the IV saline control group (n=6). The ³H penicillin is ±80% bound to albumin and thus, accumulation of radiolabel in this model reflects permeability of the BBB to large soluble molecules the size of albumin (70 kD). Only anti-FHA antibody 13.6E2 increased the passage of penicillin into brain.

EXAMPLE 6

Figure 14A:
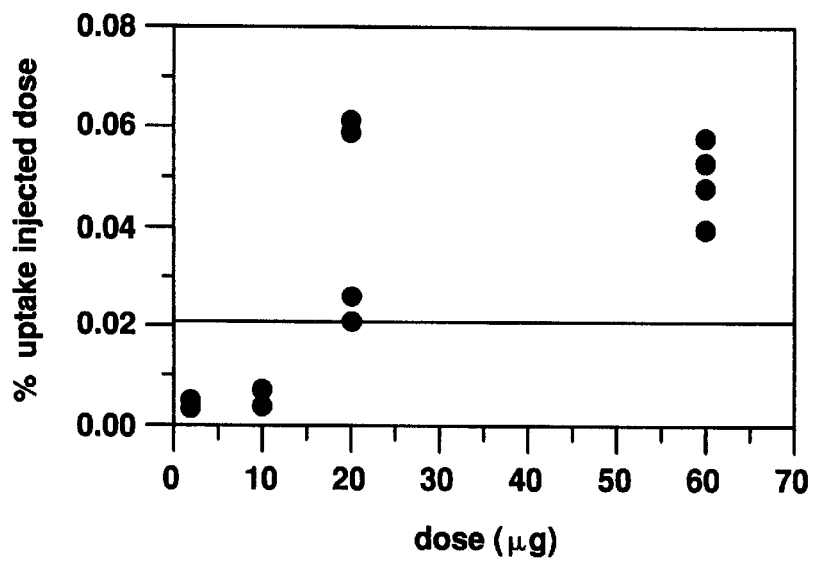
Figure 14B:
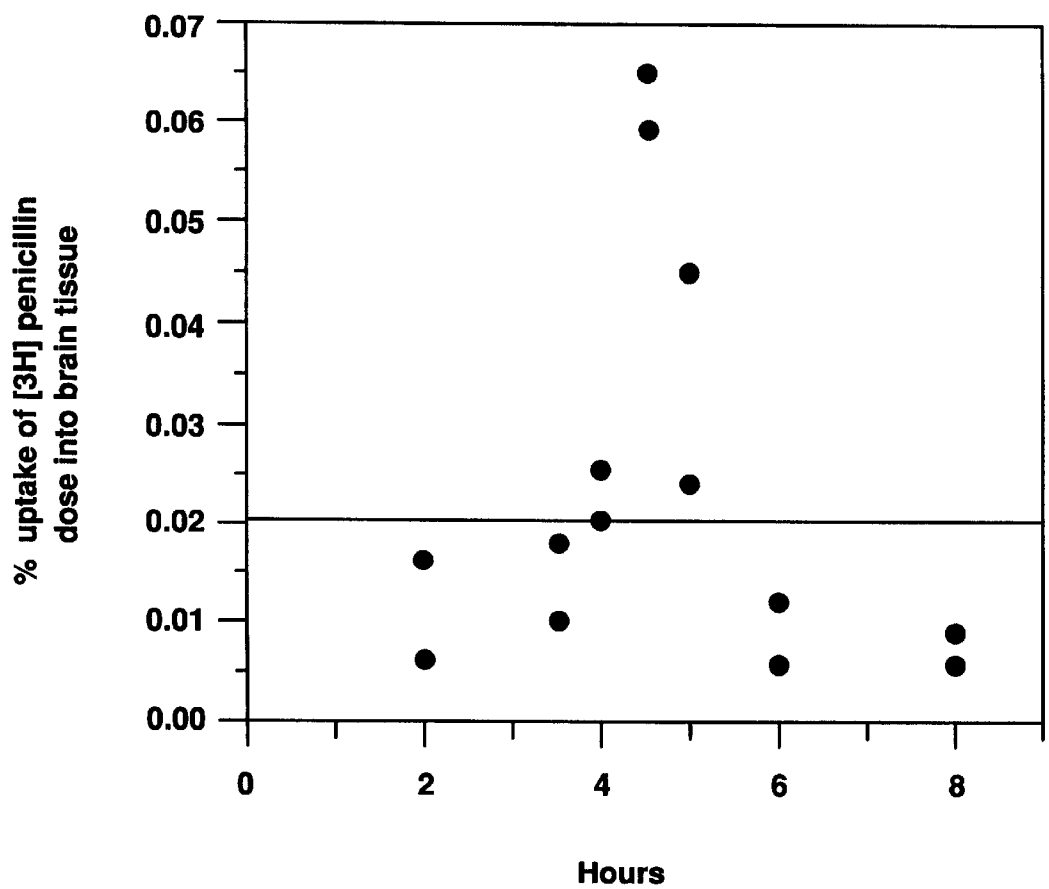

Reversible, Time Dependent Manner of
Permeability Enhancement of the Cerebral
Capillary Endothelium Following the Intravenous
Administration of an Antibody to FHA Healthy animals received antibody 13.6E2 intravenously (10 µg/kg) followed at various times thereafter by ³H penicillin intravenously. Thirty minutes after the penicillin administration, blood and brain were harvested and analyzed as in Example 5. Results from each animal are plotted individually in FIGS. 14A and 14B; cpm/g brain was converted to percent of the initial injected dose of radiolabel/ entire brain weight. These results indicate that the cerebral capillary endothelium becomes transiently permeable following the intravenous administration of anti-FHA antibodies.

EXAMPLE 7

The following formulations are antibiotic solutions which are to be co-administered with the peptides, polypeptides and antibodies of the present invention when conventional antibiotic therapy and the therapies described in the present disclosure are desired by the medical practitioner.

| Intravenous Formulation I | |
| --- | --- |
| Ingredient | mg/ml |
| cefotaxime | 250.0 |
| monoclonal antibody 12.5D1 | 10.0 |
| dextrose USP | 45.0 |
| sodium bisulfite USP | 3.2 |
| edetate disodium USP | 0.10 |
| water for injection q.s.a.d. | 1.00 ml |

Intravenous Formulation II

| Ingredient | mg/ml |
|---|---|
| ampicillin | 250.0 |
| monoclonal antibody 12.1F9 | 10.0 |
| sodium bisulfite USP | 3.2 |
| disodium edetate USP | 0.1 |
| water for injection q.s.a.d. | 1.00 ml |

Intravenous Formulation III

| Ingredient | mg/ml |
|---|---|
| gentamicin (charged as sulfate) | 40.0 |
| monoclonal antibody 12.1B11 | 10.0 |
| sodium bisulfite USP | 3.2 |
| disodium edetate USP | 0.1 |
| water for injection q.s.a.d. | 1.00 ml |

EXAMPLE 8

C3bi Capture Toxicity Test

The following procedure is used to detect the presence of toxic antibodies in the sera of animals or patients who have received a *Bordatella pertussis* vaccine or who have had the whooping cough disease.

1. C3bi coated erythrocytes ($E^{C3bi}$) are prepared by the following procedure:
   a. $E^{IgM}$ (amount see below) is put in a 15 ml tube and spun for 5 min at 2000 rpm;
   b. the supernatant is aspirated;
   c. the pellet is resuspended in Dulbecco's Glucose veronal buffer with divalent cations (DGVB++) (amount see below);
   d. C5 deficient serum is added (amount see below).

| Designation | Amount $E^{IgM}$ | Amount of DGVB++ | Amount C5 def. Serum |
|---|---|---|---|
| Super | 250 μl | 250 μl | 40 μl |
| High | 250 μl | 250 μl | 25 μl |
| Medium | 500 μl | 250 μl | 25 μl |
| Low | 250 μl | 80 μl | 8 μl |

2. The tubes containing $E^{C3bi}$ are incubated for 60 min at 37° C., the tubes are agitated after 30 min.
3. The erythrocyte coating reaction is stopped with 500 μl EDTA/G veronal buffer without divalent cations (GVB--).
4. The tubes are incubated for 10 min at 0° C. (on ice).
5. The tubes are centrifuged and the pellets are washed 4× in DGVB++. Thereafter, 5 ml DVGB++ is added and the tubes spun for 5 min at 2000 rpm at 4° C.; the supernatant us aspirated,
6. The results are resuspended in:

| | |
|---|---|
| Super | 2.5 ml DGVB++ |
| High | 2.5 ml DGVB++ |
| Medium | 5.0 ml DGVB++ |
| Low | 2.5 ml DGVB++ |

Concentration of $E^{C3bi}$ is now $1\times10^8$/ml

7. Finally, for storage of $E^{IgM}$ and $E^{C3bi}$, 1 μl penicillin/streptomycin is added per 100 μl of suspension. These preparations are stored on ice. The suspensions are usable for 3 weeks.

The $E^{C3bi}$ suspensions are used in an IgG capture on Protein A as a Toxicity Test for the sera of the animals or patients as follows:

(a) Each well of a 60 well high profile Terasaki tray (1003-01-0) is coated with 5 μl of commercial protein A solution (conc 50 ug/ml) for 2 hr. at RT.
(b) The pH of the serum/fluid is adjusted to 8.0 by adding 1/10 volume of 1.0 M Tris pH 8.0.
(c) The wells are washed 2 times with Tris (1M) pH 8.0; all fluid is aspirated.
(d) The undiluted test serum (5 μl) is added and left for 2 hr.
(e) The supernatant is aspirated and the wells are washed 2 times with PBS pH 7.4.
(f) The fluid is removed by aspiration.
(g) 5 μl of $E^{3bi}$ prepared as above is added to each well.
(h) The samples are incubated for 30 min at 37° C. in an incubator.
(i) After 30 min incubation, the plates are turned upside down for 10 min at 37° C. to allow gravity to remove unbound erythrocytes.
(j) The wells are washed with PBS 3 times, slammed on paper, and washed once more.
(k) The fluid is removed by aspiration.
(l) Glutaraldehyde (2.5%) in PBS is added for 2 minutes.
(m) The glutaraldehyde is removed and the wells are washed with PBS 3 times.
(n) $E^{C3bi}$ binding is counted at magnification of 400 (100 fields).

PBS=with Ca and Mg.
PBS/glutaraldehyde=1 ml 25% glutaraldehyde into 9 ml PBS.
Binding at or above the level of the positive control commercially available anti-C3bi or mAbF9 indicates toxic antibodies are present.

The same sera as used in Example 1 for detecting cerebral capillary endothelia binding of antibodies to FHA was used in a just described $E^{C3bi}$ binding assay. The results of this assay are shown in the following table:

TABLE 6

Ability of anti-*B. Pertussis* antisera to bind cerebral capillaries and C3bi

| Antigen | Species | Brain Cap* | C3bi Capture |
|---|---|---|---|
| preimmnune | guinea pig | -- | -- |
| | rabbit | | -- |
| | human | -- | -- |
| diptheria | guinea pig | +++ | + |
| pertussis | rabbit | | ++ |
| tetanus (DPT) | human | +++ | + |
| (Whole Cell) | | | |
| pertussis toxin | guinea pig | ++ | -- |
| (PT) (MAPT) (JNIH-7) | human | ++ | -- |
| Native FHA | guinea pig | + | + |
| | rabbit | | + |
| | human | | |
| Formalin FHA | guinea pig | + | + |
| | rabbit | | -- |
| | human | | |

TABLE 6-continued

Ability of anti-*B. Pertussis* antisera to bind cerebral capillaries and C3bi

| Antigen | Species | Brain Cap* | C3bi Capture |
|---|---|---|---|
| JNIH-6 | guinea pig | (--) | (--) |
| | rabbit | | |
| | human | + | + |
| FHA, trinitro-methane (TNM) (an inactivator of FHA) | guinea pig | ++ | -- |
| | rabbit | | |
| | human | | |

*Binding to cerebral capillaries was performed as described in Example 1.

These results show that antisera generated by immunization with FHA antigen can elicit antibodies which are immunoreactive with C3bi and with brain capillary endothelial cells. Antisera generated by immunization with non-FHA antigens are not immunoreactive with C3bi or brain capillary endothelial cells. In some instances, immunoreactivity was reduced for antisera generated from chemically modified FHA which indicates that such treatment of FHA improves the safety of such vaccines.

EXAMPLE 9

Inhibition of Leukocyte-Endothelial Cell Interactions by Peptides Derived from FHA Which Interact with CD11b/CD18 in the Same Manner as Factor X.

Experimental Procedures
Peptides

Purified FHA of *B. pertussis* was obtained from List Biologicals, Campbell, Calif. Eleven peptides derived from FHA and the CD11b/CD18 binding sites of Factor X were synthesized by the Rockefeller University Protein Sequencing facility using FMOC chemistry and purified by HPLC (Table 7). A scrambled FHA peptide of sequence DEETVK (SEQ ID NO: 19) was used as a control.

Binding of Factor X to Neutrophils

Human Factor X (Sigma or Hematologic Technologies Inc.) was labeled with $^{125}I$ using Iodogen (Pierce Chemical Co.) Human neutrophils were isolated from heparinized blood according to the manufacturer's specification using Neutrophil Isolation Medium (Cardinal Associates, Santa Fe, N.Mex.) and washed three times with 5 mM EDTA-phosphate-buffered saline (PBS), pH 7.2, at 4° C. To eliminate platelet contamination, neutrophils were incubated with autologous serum containing 5 mM EDTA for 30 mins. at 37° C., washed three times with ice-cold PBS, pH 7.2, and resuspended in RPMI 1640 tissue culture medium (Whittaker M. A. Bioproducts, Walkersville, Md.) at 4° C. Binding of $^{125}I$-Factor X to neutrophils was measured based on a method described by Altieri et al. (1991) *Science* 254: 1200–1202. Briefly, 200 $\mu$l of neutrophils ($1.5\times10^7$/ml) were supplemented with 17.5 $\mu$l of 50 mM $CaCl_2$, stimulated with 3.5 $\mu$l of 100 $\mu$M $NH_2$-formyl-Met-Leu-Phe (Sigma), and mixed with 30 $\mu$l of 10.3 $\mu$g/ml $^{125}I$-Factor X and 100 $\mu$l of 1.75 mM of peptide. Buffer alone and a peptide of scrambled sequence served as controls in each of the 3 experiments. After incubation for 20 mins. at room temperature, neutrophil-bound $^{125}I$-Factor X was separated from unbound $^{125}I$-Factor X by centrifugation of 300 $\mu$l aliquots through 50 $\mu$l of a mixture of Hi phenyl silicone oil DC 550 and methyl silicone oil DC 200 5:1 (Nye Inc. Specialty Lubricants, New Bedford, Mass.) at 12,000×g for 2 mins. Aliquots of the supernatant (cell free $^{125}I$-Factor X) and the cell pellet (cell bound $^{125}I$-Factor X) were counted in a gamma-counter. Nonspecific binding (~50,000 cpm) was determined by adding a 100 fold excess of unlabeled Factor X, and subtracted from total radioactivity (~500,000 cpm for controls).

Adherence of Neutrophils to Cultured Endothelial Cells

Human umbilical vein endothelial cells (HUVEC, first passage, Clonetics, San Diego, Calif.) were subcultured at confluence into Terasaki tissue culture wells. After 24 hours, confluent monolayers were used for adherence assays. Monolayers were stimulated with 10 ng/ml TNF alpha (Boehringer Mannheim, Indianapolis, Ind.) at 37° C. for four hours. 30 $\mu$l of human neutrophils ($10^6$/ml) were labeled with fluorescein by the method of Lo et al. (1991), *J. Exp. Med.* 173 1493–1500, and preincubated for 15 minutes at 37° C. with 20 $\mu$l of peptides (0.5 mM in HAP) or HAP (phosphate buffered saline containing 0.5 mg/ml human serum albumin, 3 mM glucose, and 0.3 U/ml aprotinin) as a control buffer. For some experiments, endothelial cells were pretreated from 10 minutes with Factor X or antibodies against Factor X receptor (EPR-1; Altieri et al. (1990), *J. Immunol.* 145, 246–253) 12H1 and 9D4 (obtained from Dr. D. Altieri, Scripps Research Institute, Lajolla, Calif.) and then washed. Neutrophils were allowed to adhere to the monolayer for 15 mins. at 37° C. and unbound cells were removed by submersion of the plate in PBS buffer. The number of adherent neutrophils was counted in a 40× microscope field and expressed as a percentage of adherence in control wells with neutrophils treated with HAP buffer alone. The mAb IB4 against CD18 (50 $\mu$g/ml; Merck Inc., Rahway, N.J.) served as a positive control.

Transendothelial Migration of Neutrophils

Transendothelial migration of neutrophils was studied based on a method described by Muller et al. (1992), *J. Exp. Med.* 176: 819–828. Briefly, human neutrophils suspended in ice-cold Hanks balanced salt solution (HBSS) containing $Ca^{++}$ and $Mg^{++}$ (Sigma) were fluoresceinated by adding 3.3 $\mu$l/ml 5-(and 6-)carboxyfluorescein diacetate, succinimidyl ester (CFSE, Molecular Probes Inc., Oreg.). After incubation for 30 mins. on ice, neutrophils were washed twice in cold HBSS with $Ca^{++}$ and $Mg^{++}$ and resuspended in cold Medium 199 (M199, Sigma) to a final concentration of $10^6$/ml. Human umbilical vein endothelial cells were subcultured at confluence into 96-well tissue culture plates (Becton Dickinson Labware, Lincoln Park, N.J.) that were coated with hydrated collagen gel (Vitrogen; Collagen Corporation, Palo Alto, Calif.) and fibronectin. Endothelial cells were stimulated with 10 ng/ml TNF-alpha for 4 hours and washed three times with warm M199. Neutrophils ($10^6$/ml) were preincubated with 0.01 mM of peptides or with 1 $\mu$M of native FHA in M199 for 5 mins. on ice before they were added in 100 $\mu$l aliquots to the endothelial cells. For positive control, neutrophils were pre-incubated with 25 $\mu$g/ml anti-CD18 mAb IB4. For negative control, neutrophils were treated with 25 $\mu$g/ml mAb W6/32 against HLA class I antigen (Dako, Carpinteria, Calif.). The cells were incubated for 1 hour at 37° C., 5% $CO_2$. To terminate transmigration, the supernatant fluid was aspirated and the wells were filled with warm 1 mM EGTA (Sigma) in HBSS without Ca and Mg. The plates were covered with plate sealers (Dynatech, Alexandria, Va.) and centrifuged in an inverted position at 250 g for 3 mins. at room temperature. To remove residual non-transmigrated neutrophils from the endothelial cells, monolayers were washed twice with 200 $\mu$l of warm Hanks solution without Ca and Mg. Fluorescence was quantitated using a fluorescence counter (Millipore Cytofluor™ 2300). The percentage of transmigrated neutrophils was determined by comparing the amount of fluorescence of test wells with that measured in collagen- and fibronectin-coated wells without endothelial cells. Fluorescence counts were corrected for contamination of the neutrophil preparation with lymphocytes (<10%) which do not transmigrate; contamination with monocytes as assessed by light microscopy was <5%. Percent inhibition of transendothelial migration of neutrophils was calculated by comparing the number of transmigrated cells in wells containing neutrophils treated with peptide to neutrophils treated with M199 alone and arbitrarily set at 100% transendothelial migration (TEM).

Generation of Factor Xa by Monocytes

Factor Xa generation was determined by a modification of the method of Miletich et al. (1978), *J. Biol. Chem.* 253: 6908–6916. THP-1 cells (ATCC; 3×10$^7$/ml) resuspended in RPMI 1640 (Bio Whittaker, Walkersville, Md.) were incubated with 100 µM ADP (Sigma), 2.5 mM CaCl$_2$, 1 or 5 µg/ml Factor X (Hematologic Technologies Inc.) and 0.5 mM peptides at room temperature. After 20 minutes, 100 µl of the reaction mixture was transferred to 37° C. and supplemented with 100 µl of bovine factor VII- and Factor X-deficient plasma (Sigma). Coagulation was initiated by adding 100 µl of 25 mM CaCl$_2$ and the clotting time was determined. Factor Xa procoagulant activity (ng/ml) was calculated by means of a standard curve constructed by serial concentrations of Factor Xa (Hematologic Technologies Inc.) from 50 to 250 ng/ml.

Results

Sequence Similarity Between FHA and the CD11b/CD18 Binding Sites of Factor X

The amino acid sequence of FHA was compared to that of the 3 regions of human coagulation Factor X that are known to bind to the leukocyte integrin CD11b/CD18. Sequence similarity was found between amino acid residues 238–246, 366–374, and 422–430 of Factor X (according to Fung et al., (1985)) *Proc. Natl. Acad. Sci. USA* 82, 3591–3595) and FHA residues 1979–1984, 2063–2068, 34–36, and 2528–2533 (according to Relman et al. (1989) *Proc. Natl. Acad. Sci. USA* 86, 2637–2641). These sequence similarities are evident from the sequence groupings displayed in Table 6; i.e., residues 238–246 of Factor X with residues 1979–1984 and 2523–2533 of FHA; residues 366–374 of Factor X with residues 2062–2068 of FHA; and residues 422–430 of Factor X with residues 32–36 of FHA.

FHA Peptides Block Factor X Binding to Leukocytes

Figure 15:
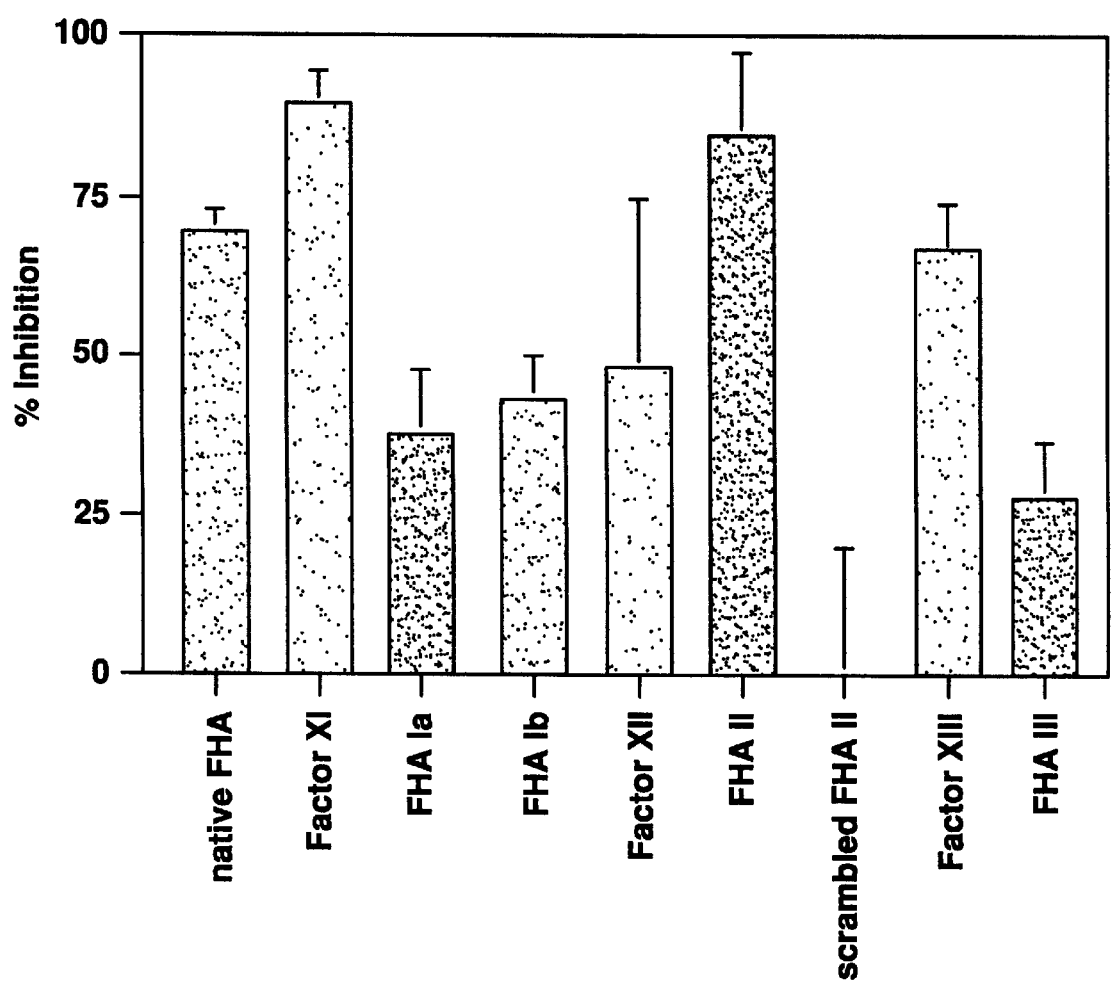
FIG. 15 is a bar graph representation of the inhibition of $^{125}$I-Factor X binding to neutrophils by FHA, FHA- or Factor X-peptides as identified in Table 6. The concentration of inhibiting substances was: peptides 0.5 mM, native FHA 0.3 $\mu$M. Values represent the mean±standard deviation of triplicate experiments.
Figure 16:
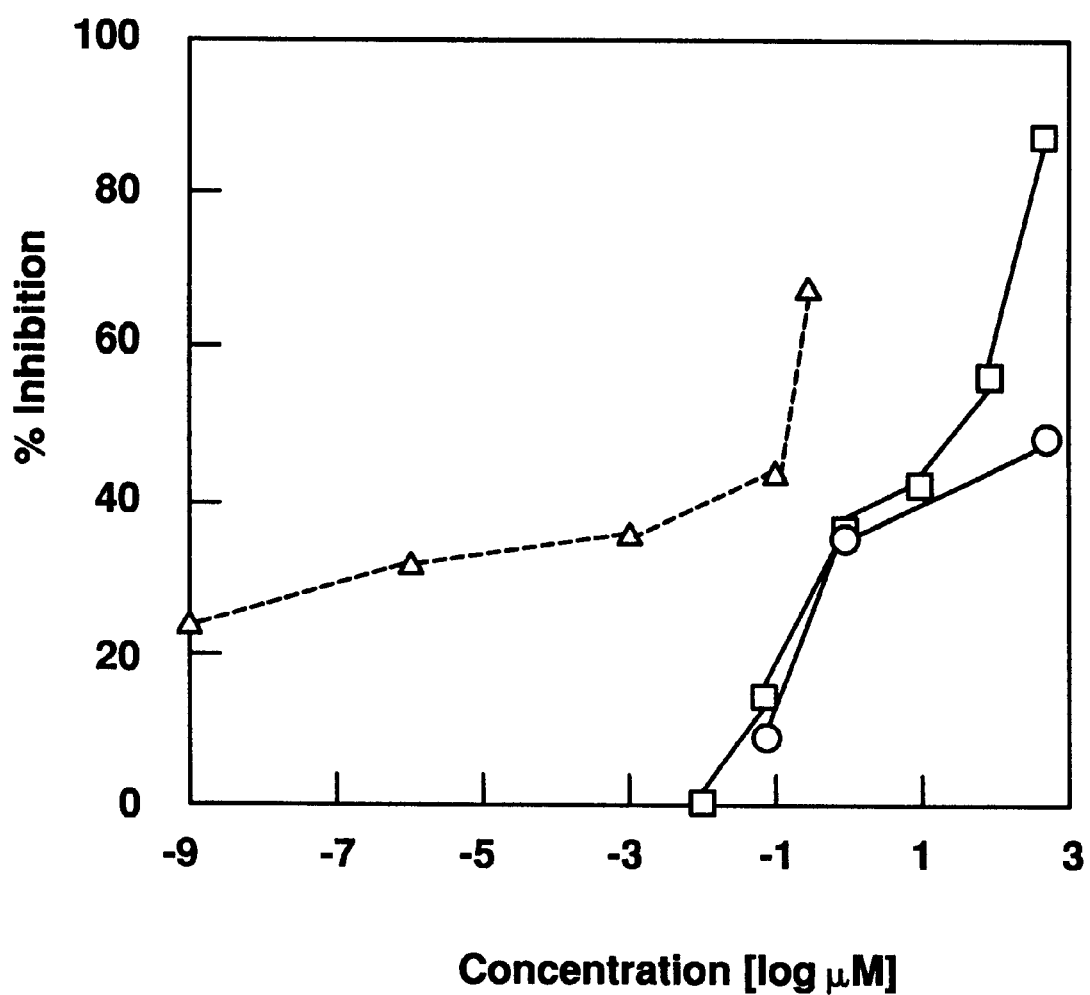
FIG. 16 is a graphical representation of the FHA, FHA- or Factor X-peptide concentration effect on the inhibition of $^{125}$I-Factor X binding to neutrophils. FHA peptide II (Square) and Factor X peptide II (Circle) at $10^{-2}$ to $5\times10^2$ $\mu$M; FHA at $10^{-6}$ to $3\times10^2$ $\mu$M (triangle). Values are representative of triplicate experiments (standard deviations <15%).

Three peptides from Factor X inhibited $^{125}$I-Factor X binding to leukocytes by 50 to 90% (FIG. 15, stippled bars). Native FHA and FHA peptide II showed strong inhibition of $^{125}$I-Factor X binding to neutrophils of 70± 4% and 87±8%, respectively (FIG. 15, shaded bars). The other FHA peptides also demonstrated significant inhibition, but to a lesser extent than the corresponding Factor X peptides. The mAb IB4 (100 µg/ml, positive control), reduced $^{125}$I-Factor X binding by 53±1%. Native FHA, FHA peptide II and the corresponding Factor X peptide II inhibited $^{125}$I-Factor X binding in a concentration dependent manner (FIG. 16). The IC$_{50}$ of native FHA was 0.1 µM, that of FHA peptide II was 10 µM while the IC$_{50}$ of Factor X peptide II was 500 µM.

FHA Peptides Inhibit Adherence and Transendothelial Migration of Leukocytes

Figure 17:
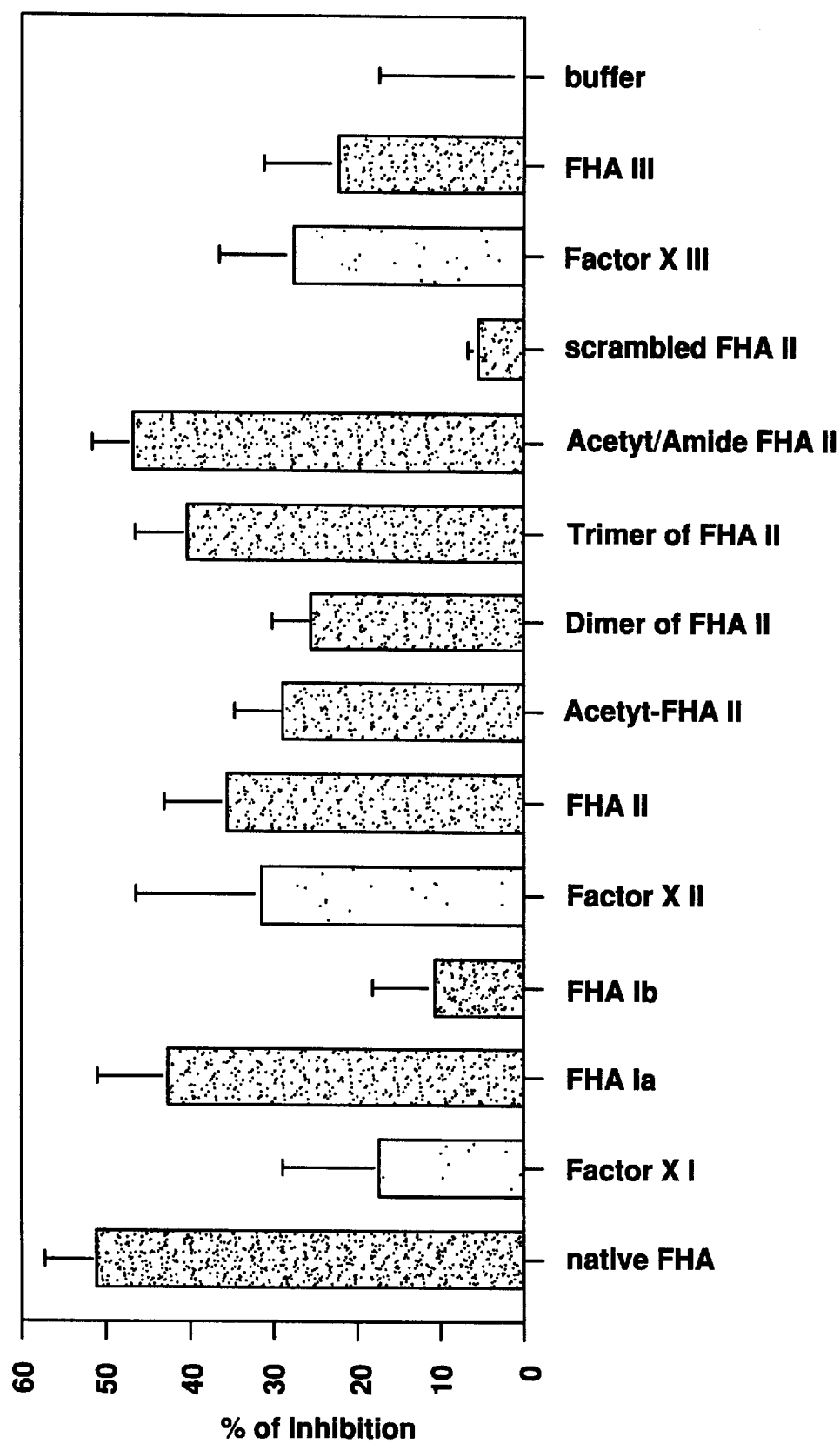
FIG. 17 is a bar graph representation of the inhibition of neutrophil adherence to activated endothelial cells by FHA, Factor X- and FHA- derived peptides. The concentration of inhibiting substances was: peptides 0.5 mM, native FHA 0.3 $\mu$M. Values represent the mean±standard deviation of 4 experiments with 5 wells/peptide.
Figure 18:
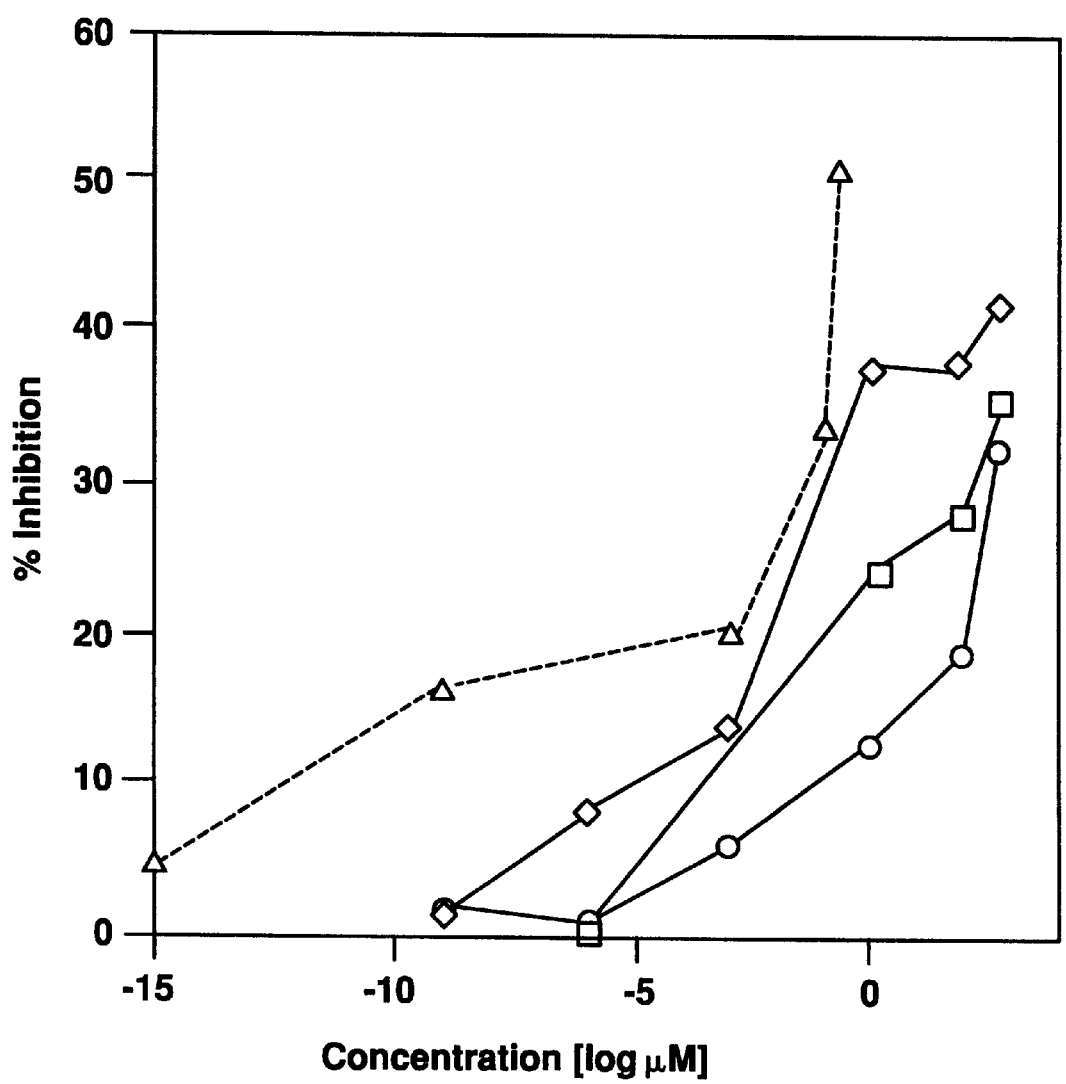
FIG. 18 is a graphical representation of the FHA, FHA- or Factor X-peptide concentration effects on the inhibition of neutrophil adherence to activated endothelial cells. FHA peptide II monomer (Square) and trimer (Diamond), Factor X peptide II (Circle) at $10^{-9}$ $\mu$M to 0.5 mM; native FHA at $10^{-6}$ to $3\times10^2$ $\mu$M (triangle). Values represent the mean of 3 experiments with 5 wells/peptide (standard deviations <15%).

FHA peptides were tested for their ability to interfere with neutrophil adherence to stimulated HUVEC (FIG. 17). Native FHA (25 µg/ml=0.3 µM) reduced neutrophil binding by 51±8%. The anti-CD18 mAb IB4 (50 µg/ml), inhibited neutrophil adherence to HUVECs by 38±10% (not shown). The FHA peptide Ia was significantly more active than the Factor X peptide I, whereas the FHA peptide II and Factor X peptide II demonstrated similar strong activities. FHA III peptide was less effective than the corresponding Factor X derived peptide. The scrambled FHA II peptide did not interfere with neutrophil binding. As shown in FIG. 18, native FHA, Factor X- and FHA-peptides were found to inhibit neutrophil adherence in a concentration dependent manner.

The most effective peptide, FHA II, consists of only 7 amino acids. To determine if increased length, acetyl modification, or acetyl and amide modifications of the peptide enhanced bioactivity, FHA peptide II was modified by synthesizing dimers and trimers of this peptide and by protecting the ends of the peptide by attaching an acetyl group to the N-terminus or by attaching an acetyl group to the N-terminus and an amide group to the C-terminus (acetyl/amide derivative). Except for the acetyl/amide derivative, these modifications did not significantly change the ability of the FHA peptide II to block neutrophil adherence to endothelia in vitro (FIG. 17). The acetyl/amide modifications significantly enhanced the ability of peptide FHA II to block neutrophil adherence to endothelia.

Figure 19A:
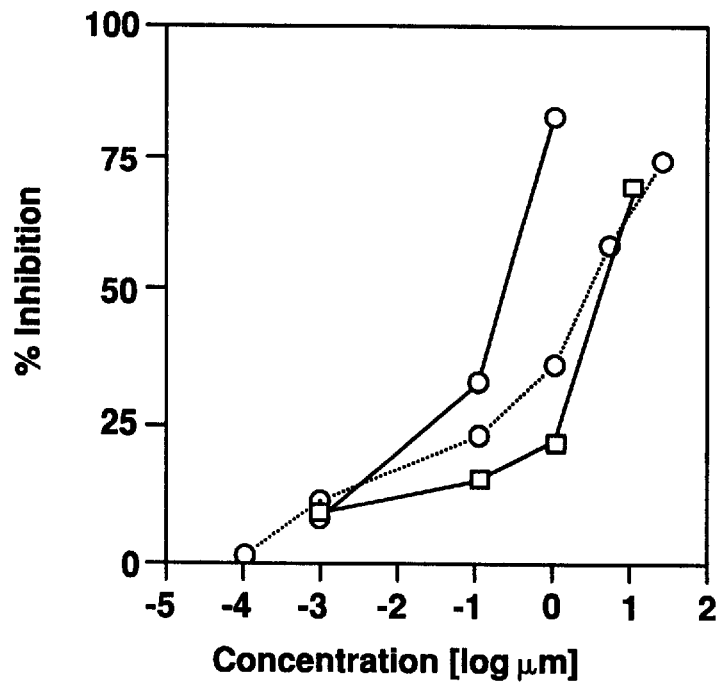
FIG. 19A is a graphical representation of the effect of trimeric FHA II, native FHA and mAb IB4 on transendothelial migration of neutrophils. Fluoresceinated human neutrophils were incubated with $10^{-3}$–10 $\mu$M of the trimeric FHA II (circle, dotted line), $10^{-3}$–1 $\mu$M of native FHA (circle, solid line), and $10^{-4}$–10 $\mu$g/ml of mAb IB4 (square). Values represent mean±standard deviation of 6 wells.
Figure 19B:
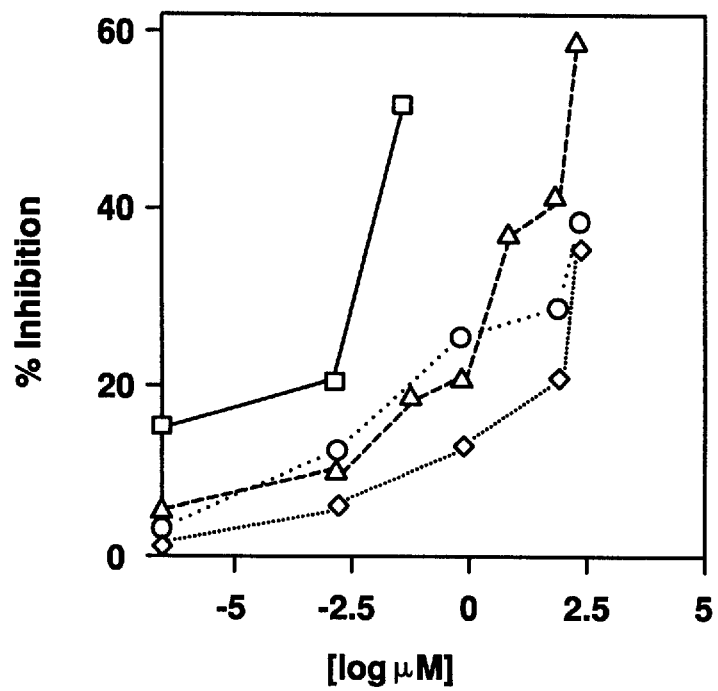
FIG. 19B is a graphical representation of the effect of FHA peptide II, acetyl/amide-FHA peptide II, Factor X peptide II and native FHA. Fluoresceinated human neutrophils were were incubated with $10^{-6}$–500 $\mu$M FHA peptide II (circle, dashed line), $10^{-6}$–500 $\mu$M acetyl/amide-FHA peptide II (triangle, dashed line), $10^{-6}$–500 $\mu$M Factor X peptide II (diamond, dotted line), and $10^{-6}$–$10^{-1}$ $\mu$M native FHA (square, solid line). Values represent the mean of 3 experiments with 5 wells/peptide (standard deviations <15%).

Since CD18-dependent leukocyte adherence to activated endothelia is a prerequisite to transendothelial migration, FHA and the corresponding Factor X peptides were tested for their ability to prevent neutrophil transmigration in vitro (Table 7). In control wells containing M199 alone, 51±10% of the neutrophils transmigrated. Monoclonal Ab W6/32 (25 µg/ml, negative control) did not inhibit transendothelial migration significantly (6±6%); monoclonal Ab IB4 (25 µg/ml, positive control), reduced transendothelial migration by 73±14% (n=6) (not shown). The trimer of FHA peptide II and the acetyl/amide modified FHA peptide II were the most effective peptides, leading to an inhibition of 68±9% and 61±6%, respectively; all other tested peptides showed an inhibition of <25% (Table 7); the % inhibition values in this Table represent mean±standard deviation of at least 3 experiments with 6 wells/peptides. The trimer of FHA peptide II, native FHA and the mAb IB4 reduced transendothelial migration of neutrophils in a concentration dependent fashion (FIG. 19A), as did FHA peptide II, acetyl/amide FHA II and Factor X peptide II (FIG. 19B). The native FHA was more active than all the tested peptides, resulting in an inhibition of transendothelial migration by 82±1% at a concentration of 1 µM. Similar inhibitory activity required 10 µM of the trimer of FHA peptide II.

TABLE 7

| Peptide | Amino Acid Sequence | % Inhibition of TEM |
|---|---|---|
| native FHA | | 82 ± 1 |
| Factor X I | $^{236}$GLYQAKRFKVG$^{246}$ (SEQ ID NO: 3) | 10 ± 6 |
| | | 23 ± 5 |
| FHA Ia | $^{1979}$LGYQAK$^{1984}$ (SEQ ID NO: 10) | |
| FHA Ib | $^{2523}$GLIQGRSVKVD$^{2533}$ (SEQ ID NO: 9) | 7 ± 10 |
| Factor X II | $^{366}$GYDTKQEDG$^{374}$ (SEQ ID NO: 1) | 14 ± 9 |
| FHA II | $^{2062}$ETKEVDG$^{2068}$ (SEQ ID NO: 7) | 21 ± 10 |
| Acetyl-FHA II | | 7 ± 1 |
| Acetyl/Amide-FHA II | | 61 ± 6 |
| Dimer of FHA II | | 15 ± 6 |
| Trimer of FHA II | | 68 ± 9 |
| scrambled FHA II | DEETVK (SEQ ID NO: 19) | 4 ± 5 |

TABLE 7-continued

| Peptide | Amino Acid Sequence | % Inhibition of TEM |
|---|---|---|
| Factor X III | $^{422}$IDRSMKTRG$^{430}$ (SEQ ID NO: 2) | 5 ± 7 |
| FHA III | $^{32}$GRTRG$^{36}$ (SEQ ID NO: 8) | 5 ± 6 |

The ability of FHA peptides and anti-CD18 or anti-Factor X receptor antibodies to interact cooperatively to inhibit neutrophil adherence to endothelial cells was assessed by measuring neutrophil adherence to endothelial cells in the presence of antibody as well as antibody plus peptide. Anti-CD18 mAb IB4 was added to leukocytes at 10 µg/ml 10 min before the assay. Anti-Factor X receptor mAb 12H1 (10 µl of ascites) or 9D4 (10 µg/ml) were added to the endothelial cell monolayers 10 min before the assay. The peptides were added at 5 µg/ml. The results are shown in Table 8 where the numerical values are in % of control binding.

TABLE 8

| | antibody | | | |
|---|---|---|---|---|
| Peptide | none | IB4 | 12H1 | 9D4 |
| none | 100 | 39 ± 8 | 57 ± 22 | 50 ± 18 |
| FHA Ia | 63 ± 12 | 20 ± 7 | 64 ± 12 | 63 ± 17 |
| FHA II | 40 ± 23 | 11 ± 6 | 67 ± 13 | 45 ± 9 |

In control wells, 228±46 neutrophils were adherent per 40X field. Maximum inhibition of antibody or peptide alone was about 40–60% of control values. Preincubation of neutrophils with FHA peptides Ia or II together with the anti-CD18 mAb IB4 (50 µg/ml) resulted in an additive reduction of neutrophil adherence to >80±10%. Antibodies to Factor X receptor did not demonstrate an additive inhibition of neutrophil adherence to endothelial cells when the antibodies were incubated together with FHA peptides Ia or II.

FHA Peptides Inhibit Factor Xa Procoagulant Activity on Monocytes

Binding of Factor X to leukocytes is followed by conversion to Factor Xa and initiation of coagulation. Factor Xa generation on activated THP-1 cells in the presence of the scrambled, control FHA II peptide was 165 ng/ml. FHA peptide Ib and III (0.5 mM) reduced Factor Xa production by 81% and 74%, respectively (p<0.05, t-test) (Table 9). Although monomeric FHA peptide II did not interfere with the generation of Factor Xa procoagulant activity, the trimer reduced Factor Xa generation by 58% (p<0.05). Factor X peptide II decreased Factor Xa production by >90% (p<0.05), while Factor X peptides I and III caused a substantial reduction that did not reach statistical significance.

TABLE 9

| Peptide | Clotting time (sec) | Factor Xa (ng/ml) |
|---|---|---|
| Factor X I | 37.0 ± 4.0 | 37.8* |
| FHA Ia | 34.1 ± 1.1 | 57.4* |
| FHA Ib | 38.0 ± 7.6 | 31.3* |
| Factor X II | 55.2 ± 4.0 | <10* |
| FHA II | 30.0 ± 5.0 | 86.0 |
| Acetyl-FHA II | 29.8 ± 3.3 | 85.9 |
| Acetyl/Amide-FHA II | 40.0 ± 3.0 | 28.5* |

TABLE 9-continued

| Peptide | Clotting time (sec) | Factor Xa (ng/ml) |
|---|---|---|
| Dimer of FHA II | 18.7 ± 0.6 | 159.8 |
| Trimer of FHA II | 32.2 ± 4.1 | 69.9* |
| scrambled FHA II | 23.1 ± 1.0 | 165.0 |
| Factor X III | 26.5 ± 2.4 | 107.5 |
| FHA III | 36.2 ± 2.7 | 43.4* |
| HAP Buffer | 26.0 ± 2.0 | 112.2 |
| Leupeptin | 63.0 ± 4.0 | <10.0* |

Values represent mean ± standard deviation of at least 3 experiments.
*Statistically significant difference as compared to scrambled FHA peptide II at $p < 0.05$ (t-test.)

EXAMPLE 10

Reduction of Inflammation in an Experimental Meningitis Model by Peptides Derived from FHA Which Interact with CD11b/CD18 in the Same Manner as Factor X.

Materials and Methods

Peptides

Filamentous hemagglutinin (FHA) of *Bordetella pertussis* (List Biologicals, Campbell, Calif.), seven peptides derived from regions of FHA and Factor X with sequence similarity as identified in Table 7 of Example 9, and a scrambled FHA peptide of sequence DEETVK (SEQ ID NO: 19) as a control, were used in the procedures of this Example. Specifically, FHA Ia, Factor X II, FHA II, acetyl-FHA II, acetyl/amide-FHA II, dimer of FHA II and trimer of FHA II were the seven FHA and Factor X peptides used in these procedures.

Rabbit Model for Meningitis

The rabbit model was performed according to an established protocol. Specific pathogen free, New Zealand white rabbits (2 kg; Hare Marland, Nutley, N.J.) were anesthetized with valium (2.5 mg/kg, subcutaneously, Hoffman-LaRoche, Nutley, N.J.), ketamine (35 mg/kg, intramuscularly, Aveco, Fort Dodge, Iowa) and xylazine (5 mg/kg, intramuscularly, Miles Laboratories, Shawnee, Kans.) and a helmet of dental acrylic was affixed to the calvarium. Twenty four hours later, the rabbits were anesthetized with ethyl carbamate (1.75 g/kg; Aldrich Chemical Co., Milwaukee, Wis.) and pentobarbital (15 mg/kg; Abbott Laboratories, Abbott Park, Ill.) and placed in a stereotaxic frame. A spinal needle was introduced into the cisterna magna and 300 µl of CSF was withdrawn. The animals were challenged intracisternally with $10^8$ heat killed, unencapsulated pneumococcus strain R6 introduced in 200 µl of saline (time 0). One hour later, animals were treated with peptides dissolved in 1 ml of saline by intravenous injection into the right marginal ear vein. The concentration of FHA was 0.1 µM and that of the FHA Ia, Factor X II, and scrambled FHA II peptides was 10 µM. For the acetyl-FHA II, acetyl/amide-FHA II, dimer of FHA II and trimer of FHA II peptides, the concentration was $10^{-3}$ µM. The concentration of FHA II is given in the results section. Samples of CSF were withdrawn at hourly intervals after pneumococcal inoculation and leukocyte density was measured using a cell counter (Coulter Electronics Inc., Hialeah, Fla.). CSF samples were centrifuged at 10,000×g for 5 minutes and the supernatant was stored at −70° C. until assayed for protein concentration using the bicinchoninic acid method (BCA Kit, Pierce Chemical Co., Rockford, Ill.) and for lactate concentration (Lactate Detection Kit, Sigma, St. Louis, Mo.). Statistically significant differences between treatments were determined by a one way analysis of variance test.

Results

The Anti-inflammatory Effect of FHA Peptides with Factor X Homology in vivo

Based on the in vitro results of the inhibition of both leukocyte adherence and transendothelial migration of Example 9, FHA peptides of residues 1979–1984 (FHA Ia) and 2062–2068 (FHA II), and the Factor X peptide of residues 366–374 (Factor X II) were predicted to exert an anti-inflammatory effect in vivo. These peptides were tested in an animal model of pneumococcal meningitis for their capacity to prevent leukocyte extravasation from the bloodstream into the cerebrospinal fluid (CSF). In this model, leukocyte migration into the CSF has been documented to be strongly CD18-dependent (Quagliarello et al., (1992), *N. Engl. J. Med.* 327, 864–872)

Figure 20A:
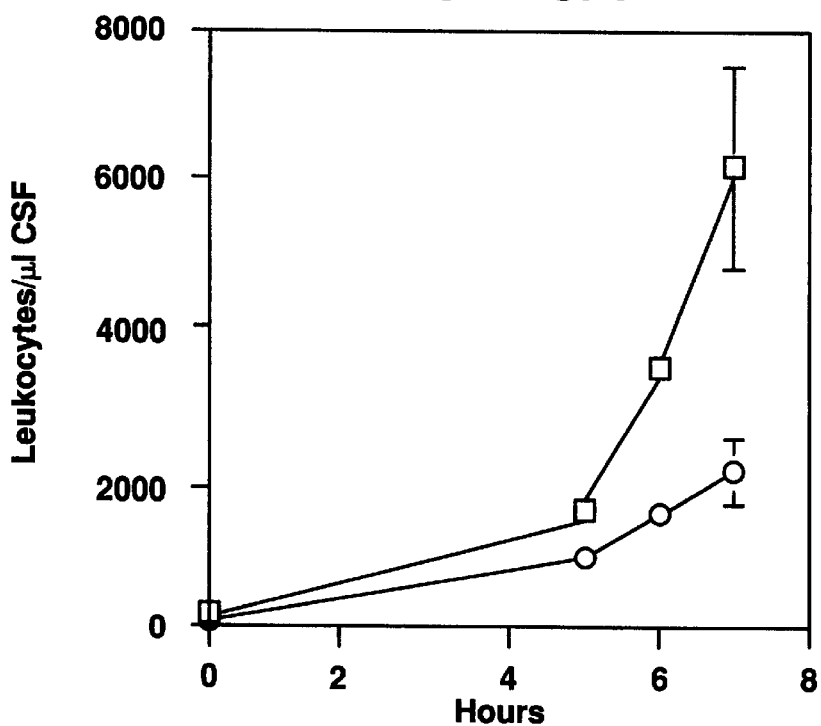
FIG. 20A: FHA O; Control □.
Figure 20B:
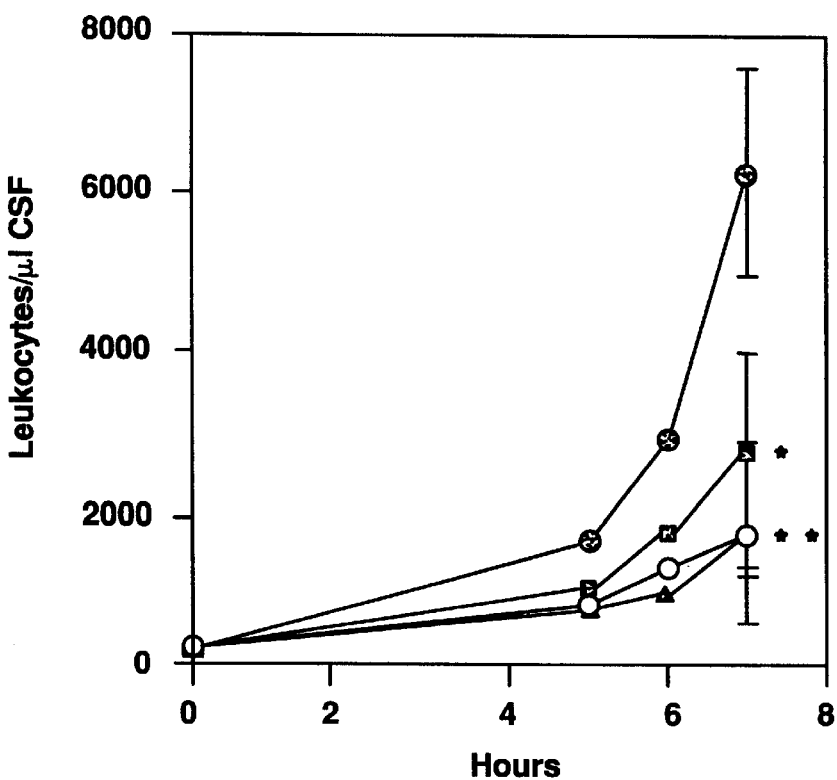
FIG. 20B: FHA peptide Ia O; FHA peptide II ■; Factor X peptide II ▲; scrambled FHA peptide II ●.

Native FHA, and FHA- and Factor X-derived peptides were injected intravenously one hour after intracisternal challenge with pneumococci. FIGS. 20A and 20B depict the leukocyte response over 7 hours. Consistent with the in vitro data, native FHA, FHA peptide Ia, FHA peptide II, and Factor X peptide II resulted in a significant reduction of CSF leukocytosis. Animals which received FHA (25 μg per 2 kg; 0.1 μM) had a mean leukocyte concentration of 2096±450/μl CSF 7 hours after challenge with pneumococci as compared to 6159±1334 for control animals which received buffer (p<0.05, Mann-Whitney test). At this point, mean leukocyte concentrations/μl CSF of animals treated with 10 μM of FHA peptide Ia, FHA peptide II, and Factor X peptide II were 1640±1210, 2645±1412, and 1622±521, respectively. (P<0.01) (FIG. 20, Panel B). These results show that the intravenous injection of native FHA, FHA peptide Ia, FHA peptide II or Factor X peptide II result in a significant reduction of CSF leukocytosis of >60%. The scrambled FHA peptide II was ineffective (6431±1380 leukocytes/μl CSF 7 hours after injection of pneumococci, p>0.05). When peptide concentrations were reduced from 10 to 0.1 μM, FHA and FHA peptide II displayed more potent anti-inflammatory activity than the corresponding Factor X peptide II (FIG. 21). Intravenous application of $10^{-3}$ μM FHA or FHA peptide II was ineffective.

To determine if modifications of FHA peptide II, which prolong its half life in serum, enhanced its anti-inflammatory activity in vivo, rabbits were treated with $10^{-3}$ μM of the acetylmonomer, the dimer and the trimer of FHA II. This dose was chosen to be below the active threshold for the monomer (FIGS. 21 and 22). As shown in FIG. 22, the acetylmonomer and the trimer of FHA peptide II resulted in a significant reduction of leukocyte migration into the CSF: mean leukocyte concentration/μl CSF 7 hours after challenge with pneumococci was 2145±922, and 2223±1057, respectively (p<0.01). The dimer of FHA peptide II did not prevent leukocyte recruitment into the CSF at this dose.

To determine the stability of the FHA II peptide, the unmodified or the acetylated-amidated peptide were incubated in 50% rabbit plasma at 37° C. The concentration of unprotected FHA peptide II was decreased by half in 4–6 hours, whereas the concentration of the acetylated/amidated derivative remained unchanged over 48 hours. Rabbits (n=10) were treated with 10 nmoles of the acetyl-amide-FHA II. Control animals (n=10) exhibited a mean of 6480±684 leukocytes/μl CSF at 6 hours post-pneumococcal challenge. In contrast, animals receiving the acetyl-amide-FHA II demonstrated a significant reduction of leukocyte migration into the CSF to 3011±684 cells/μl (p=0.0015, ANOVA) (FIG. 23).

Protection Against Blood Brain Barrier Permeability Afforded by FHA Peptides

Loss of barrier function of the cerebral capillary endothelium during inflammation is reflected by an influx of serum proteins into the CSF. Impaired cerebral metabolism has been shown to correlate with increased lactate concentrations in CSF (Tuomanen et al., 1985, *J. Infect. Dis.* 151: 859–868). To examine if the peptides were able to ameliorate these measures of cerebral injury, CSF protein and lactate concentrations were measured hourly in peptide-treated and control animals (Table 10). Ten μM FHA peptide II or acetyl/amide-FHA peptide II significantly reduced protein influx into the CSF and generation of lactate (p<0.02, Mann-Whitney test) while FHA was also significantly protective for protein influx and lactate generation. FHA peptide Ia, and Factor X peptide II caused no significant reduction.

TABLE 10

Effect of Peptides on Blood Brain Barrier Permeability and Lactate Metabolism During Meningeal Inflammation

| Peptide | Lactate (mg/100 ml) | Protein (mg/ml CSF) |
| --- | --- | --- |
| Control | 38.7 ± 4.8 | 2.1 ± 0.4 |
| FHA | 25.0 ± 5.3 | 1.3 ± 0.3* |
| FHA Ia | 36.0 ± 6.7 | 1.8 ± 0.4 |
| Factor X II | 37.6 ± 6.9 | 1.6 ± 0.7 |
| FHA II | 25.5 ± 4.1* | 1.4 ± 0.6* |
| Acetyl/Amide FHA II | 24.3 ± 3.2* | 1.2 ± 0.6* |
| scrambled FHA II | 40.7 ± 5.8 | 1.9 ± 0.3 |

Mean values for CSF lactate and protein at time 0 were 18.6 ± 5.8 and 0.8 ± 0.2 respectively. Ten control animals received phosphate-buffered saline.
The concentration of FHA II intravenously injected one hour after challenge with pneumococci was 10 μM.
Values represent mean ± standard deviation of concentrations in CSF at 6 hours after pneumococcal challenge (n ≦ 4 for peptide treated animals; n = 4 for FHA).
*Statistically significant difference as compared to control at p < 0.02 (Mann-Whitney test).

Attachment of the acetyl-group to the N-terminus augmented this protective activity: $10^{-3}$ μM Acetyl-FHA peptide II still significantly inhibited accumulation of proteins in the CSF and the generation of lactate (p<0.01) in contrast to FHA peptide II that was ineffective at this dose (p>0.5) (Table 11). Seven hours after intracisternal challenge with pneumococci, protein concentrations in the CSF of all peptide-treated rabbits were not significantly lower than those of control animals (p>0.02) indicating escape from the bioactivity of the peptides.

TABLE 11

Effect of variation of peptide II structure on parameters of injury during meningeal inflammation.

| Peptide | Lactate (mg/100 ml) | Protein (mg/ml CSF) |
| --- | --- | --- |
| Control | 38.7 ± 4.8 | 2.15 ± 0.41 |
| FHA II | 35.3 ± 6.7 | 2.45 ± 0.22 |
| Acetyl-FHA II | 27.2 ± 4.4* | 1.42 ± 0.47* |
| Dimer of FHA II | 34.2 ± 5.6 | 1.69 ± 0.41 |
| Trimer FHA II | 44.6 ± 6.8 | 1.56 ± 0.24 |

Again, mean values for CSF lactate and protein at time 0 were 18.6 ± 5.8 and 0.8 ± 0.2, respectively. Ten control animals received phosphate-buffered saline.
The concentrations of FHA II intravenously infected was $10^{-3}$ μM.
Values represent mean ± standard deviation of concentrations in CSF at 6 hours after pneumococcal administration (n ≦ 4 per group).
*Statistically significant difference as compared to control at p < 0.02 (Mann-Whitney test).

EXAMPLE 11
Peptide Derivatives of RGD Region of FHA Which Inhibit Leukocyte Adherence to Endothelial Cells and Transmigration Across Endothelial Monolayers.

Materials and Methods

Peptides

Filamentous hemagglutinin (FHA) of *B. pertussis* (List Biologicals, Campbell, Calif.) was tested as purified protein. Six synthetic 45-mers and one 50-mer were obtained from Lederle-Praxis Biologics, W. Henrietta, N.Y.: FHA A (SEQ ID NO: 20), B (SEQ ID NO: 21), and C (SEQ ID NO: 22) spanned the region containing the RGD motif (FIG. 24); FHA D, E, F, and G spanned the contiguous amino acid residues 1142–1146, 1147–1191, 1192–1235, and 1236–1285 respectively. See FIG. 3 for the relative location of these peptide and polypeptide fragments. Four 20-mers (FHA C a-d) (SEQ ID NO: 23 to SEQ ID NO: 26) derived from FHA C residues 1097–1136 (FIG. 24) were synthesized by the Rockefeller University Protein Sequencing facility using FMOC chemistry utilizing HBTU activation coupled with NMP. All peptides were purified by high performance liquid chromatography to >95% purity.

Adherence of Neutrophils to Cultured Endothelial Cells and Transendothelial Migration of Neutrophils The procedures for determining the neutrophil adherence to cultured endothelial cells and the transendothelial migration of neutrophils were identical with those of Example 9. Control values were the same as those shown in Example 9.

Downmodulation of CD11b/CD18

Human monocytes were purified from buffy coats on Percoll gradients and cultured in 12.5% human serum in Teflon beakers. Macrophages were harvested from Teflon beakers after 6–8 days and suspended in HAP buffer. Terasaki wells were coated with 5 $\mu l$ of peptides (0.5 mM) or anti-CD18 mAb IB4 (50 $\mu g/ml$). Control wells were coated with HAP. After 2 hours of incubation at RT, 5 $\mu l$ of macrophages ($5\times10^5$/ml HAP) were added and allowed to spread for 45 mins. at 37° C. Binding of macrophages to surfaces coated with ligands has been shown to downmodulate receptors in the membrane so that the apical surface becomes depleted of receptors (Wright, et al. (1983), *Proc. Natl. Acad. Sci. USA* 80, 5699–5703, and Michl, et al. (1983), *J. Exp. Med.* 157, 2121.) To assay for residual CD11b/CD18 not engaged by the peptide, wells were washed and 5 $\mu l$ of C3bi-coated erythrocytes ($5\times10^6$/ml; C3bi is a specific ligand for the integrin CD11b/CD18), were added for 30 mins. at 37° C. IgM-coated erythrocytes in buffer served as negative control. After washing, the number of erythrocytes bound per 100 leukocytes (adherence index) was quantitated visually under an inverted microscope.

Rabbit Model for Meningitis

The anti-inflammatory effects of the administered peptides were assessed in the rabbit model for meningitis by the procedures described in Example 10. The animals received 1 ml of 1 uM peptide intravenously. In a slight departure from the protocol described in Example 10, samples of blood were drawn from the left marginal ear vein 30 minutes after the administration of the peptides to determine peripheral leukocyte concentrations.

Results

FHA Peptides Inhibit Adherence and Transendothelial Migration of Leukocytes in vitro Native FHA (50 ug/ml; 0.2 uM) inhibited adherence of human neutrophils to cultured endothelial cells by 51±7%. FHA peptide C (residues 1097–1141; 1 mg/ml; 0.2 mM) reduced neutrophil adherence by 62±12% (mean±standard deviation of 4 independent experiments with 5 wells/peptide). In contrast, FHA peptide B (residues 1076–1120) showed a reduction of 29±14%, while FHA peptides A (residues 1055–1099), D (residues 1141–1185), E (residues 1171–1215), F (residues 1201–1245), and G (residues 1231–1285) were ineffective (inhibition <15%). These results led us to focus this study on FHA peptide C.

To further dissect the activity of peptide C, its two composite 20-mer peptides (FIG. 24) spanning residues 1097–1116 (FHA Ca) (SEQ ID NO: 23) and 1117–1136 (FHA Cd) (SEQ ID NO: 26) were compared for the ability to block leukocyte adherence to endothe-lial cells. FHA peptide Ca was highly effective: 47±7% inhibition at 0.5 mM. This value was similar to the maximum obtained for native FHA (FIG. 25A) and the control anti-CD18 mAb IB4 (38±10% at 50 $\mu g/ml$). FHA peptide Cd was significantly less active (<15% inhibition at 0.5 mM). As shown in FIG. 25B, native FHA and FHA peptide Ca inhibited neutrophil binding to HUVECs in a concentration dependent fashion. The native protein and the peptide both showed maximal inhibition of neutrophil attachment of ~50%. Loss of activity (≦20% inhibition) occurred at 1 and $10^{-3}$ $\mu M$ for the peptide and the native protein, respectively.

The role of the RGD triplet in blocking neutrophil adherence by the Ca peptide was determined by comparing corresponding FHA peptides Cb and Cc in which RGD was replaced by RAD or AAD, respectively (FIG. 24). When RGD was altered to RAD, activity was decreased by half, a level statistically different from the RGD peptide and significantly above control (FIG. 25A). When RGD was changed to AAD, activity was detectable above background but was not statistically different from buffer alone.

Since migration of leukocytes across an endothelial cell barrier has been shown to involve CD18 (Tuomanen, et al (1989), *J. Exp. Med.* 170, 959), FHA and the FHA C peptides were tested for the ability to block neutrophil transmigration in vitro. FHA peptide Ca inhibited transendothelial migration by 83±8%, a value comparable to the control anti-CD18 mAb IB4 (73±14%) (Table 12). All other peptides were ineffective. FHA peptide Ca, native FHA, and mAb IB4 blocked transendothelial migration in a concentration dependent manner (FIG. 26). Intact FHA was somewhat more active than peptide Ca, achieving 82±1% inhibition at 1 $\mu M$, a value requiring 10 $\mu M$ of peptide Ca.

TABLE 12

Inhibition of transendothelial migration of neutrophils by FHA and FHA-derived peptides.

| Peptide | Amino Acid Sequence | % Inhibition of TEM |
|---|---|---|
| FHA | | 82 ± 1 |
| FHA Ca | $^{1097}$RGDPHQGVLAQGDIIMDAKG$^{1116}$ (SEQ ID NO: 23) | 83 ± 8 |
| FHA Cb | RADPHQGVLAQGDIIMDAKG (SEQ ID NO: 24) | 8 ± 9 |
| FHA Cc | AADPHQGVLAQGDIIMDAKG (SEQ ID NO: 25) | 11 ± 11 |
| FHA Cd | $^{1117}$GTLLLRNDALTENGTVTISA$^{1136}$ (SEQ ID NO: 26) | 6 ± 6 |

Values represent mean ± standard deviation of at least 3 experiments with 6 wells/peptide.

These results indicate that peptide FHA Ca has the best inhibitory activity of the peptides tested. However, peptides FHA Cb, FHA Cc, and FHA Cd are not devoid of inhibiting activity, as can be seen from the data presented in Table 13, infra.

FHA Peptides Interact with CD11b/CD18

To determine the ability of the peptides to ligate and downmodulate the integrin CD11b/CD18, macrophages were allowed to adhere to wells coated with peptide. CD11b/CD18 receptors not captured under the cell were detected with C3bi-coated erythrocytes. FHA peptide Ca and the control anti-CD18 mAb IB4 reduced the binding of C3bi-coated erythrocytes to macrophages by 61±7% and 67±3%, respectively (FIG. 27). FHA peptides Cb, Cc and FHA peptide Cd showed no significant effect.

The Anti-inflammatory Activity of FHA Peptides in Experimental Meningitis

Based on these in vitro experiments, we reasoned that of the tested peptides, FHA peptide Ca would have the potential for the strongest anti-inflammatory activity in vivo. To study this hypothesis, the peptides were tested in an animal model of bacterial meningitis for the ability to prevent leukocyte migration from the bloodstream into the cerebrospinal fluid (CSF) in response to intracisternal inoculation of pneumococci. FHA and FHA peptides were injected intravenously one hour after intrathecal pneumococcal challenge. Intact FHA (0.1 $\mu$M; 25 $\mu$g/animal) reduced CSF leukocytosis significantly: mean leukocyte density/$\mu$l CSF 7 hours after challenge with pneumococci was 2096±450 as compared to 6159±1334 for untreated controls (p<0.02; Mann-Whitney test). FHA peptides Ca and Cb showed similarly potent effects: 2137±1498 and 2788±1022 cells/$\mu$l CSF, respectively (FIG. 28). FHA peptide Cd had no effect on the leukocyte recruitment into the CSF (p>0.5). When the peptide doses were reduced, it became evident that FHA peptide Ca was clearly more active than FHA Cb; a dose of 0.1 $\mu$M FHA peptide Ca still significantly reduced leukocyte migration into the CSF (p<0.01) in contrast to FHA peptide Cb that was ineffective at this dose (p>0.5) (FIG. 29).

Leukocyte migration into the CSF in bacterial meningitis is associated with loss of barrier function of the cerebral capillary endothelium, resulting in influx of serum proteins into the CSF. To determine whether FHA peptides were able to prevent this leukocyte-dependent injury, protein concentrations in the CSF were measured throughout the course of inflammation in peptide-treated and control animals. As expected, the peptide that blocked leukocyte migration into the CSF most effectively, FHA peptide Ca, reduced the influx of serum protein significantly during the entire observation period (Table 13).

TABLE 13

Effect of peptides on blood brain barrier permeability associated with meningeal inflammation.

| Peptide | Total protein in CSF (mg/ml) | |
|---|---|---|
| | 6 hours[1] | 7 hours |
| intact FHA | 1.70 ± 0.33 | 1.86 ± 0.76 |
| FHA Ca | 1.18 ± 0.39* | 1.69 ± 0.41* |
| FHA Cb | 1.91 ± 0.24 | 2.28 ± 0.28 |
| FHA Cc | 1.36 ± 0.16 | 1.90 ± 0.22 |
| FHA Cd | 1.71 ± 0.19 | 2.03 ± 0.57 |
| Control | 2.15 ± 0.41 | 2.30 ± 0.31 |

Values represent mean ± standard deviation of at least four animals per group.
[1]Time after intracisternal inoculation of pneumococci.

EXAMPLE 12

Cross-Reactivity of Monoclonal Antibodies to FHA with Complement Component C3bi

Materials and Methods

Reagents

Four previously described (Delisse-Gathoye et al. (1990), Infect. Immun. 58: 2895–2905) monoclonal antibodies to distinct domains of FHA were used: antibody 12.5A9 to the region 1141–1279, antibody 12.1F9 to the region 1279–2011, and antibodies 12.2B11 and 12.6F8 to the region 2011 to the carboxyterminus. All monoclonals were of the IgG1 isotype and were kindly provided by Drs. Iver Heron and Per Ibsen, Statens Seruminstitut, Copenhagen, Denmark. Monoclonal anti-human von Willebrand Factor antibody was purchased from Dako, Carpinteria, Calif. Monoclonal anti-human C3bi antibody was purchased from Quidel, San Diego, Calif.

Human sera were obtained from Dr. Marta Granstrom, Stockholm, Sweden, or from the Rockefeller University collection. All sera were heated for 30 mins. at 56° C. before use.

Peptides (Table 13) were synthesized and purified by the Protein Sequencing Facility of the Rockefeller University. Peptide C3/12, an RGD-containing peptide derived from C3bi, was a generous gift from Dr. S. Wright (Rockefeller University, New York, N.Y.). FHA was obtained from List Biologicals, Campbell, Calif.

C3bi-coated Erythrocytes

C3bi-E were produced using an adaptation of the procedure of Wright et al. (1982) J. Exp. Med. 156: 1149–1164. Briefly, 5 ml sheep blood was washed and the erythrocytes ($E^{SH}$) were stored on ice at $10^9$ cells/ml. The $E^{SH}$ and sera were incubated with rabbit polyclonal IgM anti-sheep red cells (Diamedex Corp., Miami, Fla.) for 30 mins. at 37° C. and thereafter for 30 mins. at 0° C. to create $E^{IgM}$. For $E^{C3bi}$ high or medium titer, 80 $\mu$l or 25 $\mu$l, respectively, of human C5-deficient serum (Sigma Chemical Co., St. Louis, Mo.) was added to 500 $\mu$l of $E^{IgM}$. The $E^{IgM}$ and sera were incubated for 60 mins. at 37° C.; the reaction was stopped by incubation on ice for 10 mins. The resulting $E^{C3bi}$ were washed four times and stored on ice at 4° C. at $10^8$ cells/ml for up to 3 weeks.

Binding Assays

Sixty well Terasaki tissue culture plates (Robbins Scientific, Mountain View, Calif.) were coated with 5 $\mu$l of a 50 $\mu$g/ml solution monoclonal antibody for at least 1 hour at RT. Thereafter 5 $\mu$l of HAP-buffer (phosphate buffered saline with 3 mM D-glucose, 0.03 M calcium chloride, aprotinin (0.5 TIU/ml), human serum albumin (0.5 g/l)) was added to each well for 1 hour at RT. The wells were washed 6 times with phosphate buffered saline and the fluid was removed by aspiration. Five $\mu$l of $E^{C3bi}$ at $5\times10^5$ cells/ml (medium) was added for 30 mins. at 37° C. and then washed three times with strong agitation. The fluid was removed by aspiration and captured cells were fixed with glutaraldehyde (2.5%) for 2 minutes. The number of erythrocytes were counted visually at a magnification of 400× in 64 fields (adherence index). For peptide inhibition assays, the peptides were diluted to 50 $\mu$g/ml in HAP and added to the wells coated with the monoclonal antibody for 30 mins. at 37° C.; peptides remained present upon addition of $E^{C3bi}$. Sheep erythrocytes not incubated with C5 deficient serum were used as controls.

For assays with serum, the wells of microtrays (Robbins 1006-01-04) were first coated with 5 $\mu$l of protein A (50 $\mu$g/ml, Sigma, St. Louis, Mo.) for 2 hours at RT. The pH of each serum was adjusted to 8.0 by addition of 1/10 volume of 1 M Tris (pH 8). The wells were washed twice with Tris, and after aspiration of the fluid, 5 $\mu$l of serum was added and incubated for 2 hours. The wells were washed twice with phosphate buffered saline, the fluid was aspirated, and $E^{C3bi}$ (high) were added as described above.

Results 12.1F9 Antibody to FHA Binds C3bi

The abilities of 4 anti-FHA monoclonal antibodies to bind $E^{C3bi}$ were compared. A mouse monoclonal antibody of the same isotype served as the negative control and a commercial anti-C3bi monoclonal antibody was used as a positive control. Antibody 12.1F9 captured $E^{C3bi}$ in a concentration dependent manner comparable to that of the commercial anti-C3bi antibody (FIG. 30). Control sheep erythrocytes showed no significant binding. A low but detectable level of binding occurred with other anti-FHA antibodies but no clear dose response was obtained. The 50% maximal binding for 12.1F9 was 0.5 ng/ml and for anti-C3bi was 5 ng/ml. For all other anti-FHA antibodies the 50% maximal binding values were >500 ng/ml.

Inhibition of Binding of 12.1F9 to $E^{C3bi}$ by Peptides

The antibody 12.1F9 maps to the region 1279–2011 of FHA. When the derived amino acid sequence of this region was compared to that of C3, a region of 11 amino acids with similar sequence was found between FHA residues 1408–1418 and C3 residues 1187–1197 (Table 14). To study the mechanism of the interaction between antibody 12.1F9 and C3bi, native FHA and several peptides from FHA and C3 were examined for their ability to competitively inhibit this interaction (Table 14). Native FHA blocked binding almost completely, while none of the RGD-containing peptides influenced binding significantly. However, the FHA-20-mer and the homologous C3-derived peptide blocked binding by up to 60%.

TABLE 14

Ability of Peptides to Block the Recognition of C3bi by 12.1F9

| Peptide | | Adherence index |
|---|---|---|
| none | | 100 |
| FHA RGD | VTVGRGDPHQG (SEQ ID NO: 27) | 85 ± 9 |
| C3/12 | TRYRGDQDATMS (SEQ ID NO: 28) | 127 ± 27 |
| FHA 1408-1418 | YTVSADAIALA (SEQ ID NO: 29) | 21 ± 11 |
| C3-pep 1187-1197 | YTVAIAGYALA (SEQ ID NO: 30) | 30 ± 16 |
| FHA (native) | | 16 ± 16 |

Values are normalized to a control value of 100; data are expressed as the mean±SD of 6 experiments with duplicate wells.

Ability of Anti *Bordetella pertussis* Antisera to Bind C3bi

To begin to address the possible significance of the C3bi cross-reactive antibodies, we examined sera from humans vaccinated with the whole-cell pertussis vaccine, a monocomponent pertussis toxoid vaccine (JNIH-7), or a two-component vaccine containing pertussis toxoid and FHA in equal proportions (JNIH-6). Binding of $E^{C3bi}$ was found in sera from humans vaccinated with the whole cell vaccine (4 of 4) and with JNIH-6 (1 of 3) (Table 15).

TABLE 15

Ability of Antisera from Vaccines to Bind C3bi-Coated Erythrocytes.

| Vaccine antigen (n) | Adherence index |
|---|---|
| Preimmune (7) | 24 ± 11 |
| Whole cell DPT (4) | 187 ± 32* |
| | 164 ± 24* |
| | 178 ± 36* |
| | 155 ± 33* |
| JNIH-7 (4) | 54 ± 23 |
| | 63 ± 22 |
| | 44 ± 12 |
| | 31 ± 29 |
| JNIH-6 (3) | 197 ± 43* |
| | 89 ± 38 |
| | 57 ± 28 |

*Significantly above control; DTP = Diphtheria-Tetanus-Pertussis vaccine; JNIH-7 = monocomponent toxoid vaccine (12 mg/l protein nitrogen); JNIH=6 = two component vaccine: 7.5 mg/l of protein nitrogen pertussis toxoid and 7.5 mg/l of protein nitrogen of FHA.

Wells were coated with the indicated undiluted serum. $E^{C3bi}$ (high) were added at $5 \times 10^8$/ml and the adherence index determined as the number of $E^{C3bi}$ bound as counted in 64 fields. Except for the values for the preimmune sera which were combined as a single mean, values are shown for individual sera as means±SD of triplicate wells and are represented of 4 experiments.

EXAMPLE 13

Inhibition of Experimental Bacterial Meningitis by Peptides Derived from FHA

One of the hallmarks of bacterial meningitis is the influx of polymorphonuclear neutrophils into the subarachnoid space. It may be possible to prevent this influx, and the consequences of subarachnoid space inflammation, by antagonism of adhesion receptor binding. Certain FHA-derived peptides were tested in a rat model of bacterial meningitis for their capacity to prevent leukocytosis in the CSF. The FHA peptides tested were FHA Ca (SEQ ID NO: 23), a scrambled FHA Ca 20-mer control peptide of sequence IDVPQHGGAMRDLGIAQGKD (SEQ ID NO: 37), acetylated/amidated FHA II (ac/am FHA II), or an acetylated/amidated scrambled FHA II control peptide of sequence VEEDTKG (SEQ ID NO: 38).

EXPERIMENTAL PROCEDURES

The experiments were performed according to established protocols (Wispelway et al., 1988, *J. Clin. Invest.,* 82: 1339–1346). Purified *Haemophilus influenzae* type b strain DL42 lipooligosaccharide (LOS) was prepared for inoculation by sonication for 30 minutes, dilution to the desired concentration (20 ng/50 μl) in normal saline or PBS, and sonication for an additional 15 to 30 minutes just prior to use.

Briefly, anesthetized female Wistar rats were placed under a micromanipulator and inoculated intracisternally with a 25 gauge needle. After removal of 50 μl of CSF (without visible blood contamination), rats were inoculated intracisternally with 50 μl (20 ng) of LOS using a 1 ml syringe with a 25 gauge needle. Ten to fifteen minutes after inoculation with LOS, the rats were treated by intravenous administration of the test substance: a solution of an FHA peptide in PBS, a solution of a control peptide in PBS, or an equal volume of PBS alone.

Three hours after LOS inoculation, 5 μCi of $^{125}$I-radiolabelled albumin in 50 μl normal saline was administered intravenously. One hour later, CSF was collected via intracisternal puncture and blood samples were collected via intracardiac puncture. CSF leukocytosis was determined by manually counting white blood cells using a hemacytometer, and blood-brain barrier permeability was determined as the percent of radioactivity in whole blood that was present in the CSF. Blood samples were obtained immediately prior to inoculation, immediately prior to treatment, and at 4 hours post-inoculation for determination of peripheral white blood cell concentrations.

RESULTS

The results of three separate experiments are shown in Table 16. In all cases, at 4 hours after LOS inoculation, the control animals treated with PBS alone had mean CSF leukocyte concentrations of approximately 20,000 cells/ml. Systemic administration of FHA Ca peptide at 50 nmol or 100 nmol resulted in statistically significant reduction in mean CSF leukocytosis, to approximately 9100 and 6800 cells/ml, respectively. In contrast, administration of the control peptide had no effect on CSF leukocytosis (approximately 20,000 cells/ml).

Systemic administration of acetyl/amide FHA II at 600 nmol resulted in reduction in mean CSF leukocytosis to approximately 10,000 cells/ml and the control peptide resulted in a CSF leukocyte concentration of approximately 14,000 cells/ml.

No neutropenia was observed following administration of FHA Ca or acetyl/amide FHA II. Inhibition of blood-brain barrier permeability appeared to be dose dependent in the case of FHA Ca, and was not observed in preliminary experiments using the acetyl/amide FHA II peptide (data not shown).

TABLE 16

Rat Meningitis Model

| Test Substances | Leukocytosis | BBB permeability |
|---|---|---|
| | Experiment #1 [50 nmol FHA Ca] | |
| PBS | 20,000 ± 6,500 (n = 8) | 5.9 ± 2.7 (n = 6) |
| FHA Ca | 9,100 ± 4,000 (n = 9) p < 0.001 | 5.8 ± 2.7 (n = 7) |
| | Experiment #2 [100 nmol FHA Ca vs. 100 nmol scrambled FHA Ca] | |
| PBS | 20,5000 ± 6,900 (n = 14) | 4.99 ± 1.89 (n = 14) |
| scrambled FHA Ca | 20,700 ± 7,400 (n = 9) | 6.74 ± 3.48 (n = 7) |
| FHA Ca | 6,800 ± 6,500 (n = 11) p < 0.001 p < 0.001 | 3.0 ± 2.2 (n = 10) p = 0.02 vs. saline p = 0.016 vs. scrambled Ca |
| | Experiment #3 [600 nmol acetyl/amide FHA II vs 600 nmol scrambled acetyl/amide FHA II] | |
| PBS | 18,083 ± 4450 (n = 6) | 8.90 ± 4.74 (n = 6) |
| scrambled ac/am FHA II | 14,287 ± 10,199 (n = 8) p = 0.4138 vs PBS | 7.74 ± 3.59 (n = 7) p = 0.6030 vs PBS |
| ac/am FHA II | 10,500 ± 8523 (n '2 8) p = 0.0719 vs PBS | 6.00 ± 5.14 (n = 8) p = 0.3020 vs PBS |

EXAMPLE 14

Reduction in Cerebral Infarct Volume in Rat Model by Peptides Derived from FHA

Certain FHA derived peptides were tested in a rat model of cerebral infarct resulting from transient middle cerebral artery occlusion (MCAO).

EXPERIMENTAL PROCEDURES

The experiments were performed according to an established protocol described by Chen et al., 1992, *Neuroscience Research Communications*, 11: 93–99. Peptide samples FHA Ca (SEQ ID NO: 23) and scrambled FHA Ca (control) (SEQ ID NO: 37) were prepared by reconstitution in saline to a concentration of 50 nmol peptide/100 µl.

Briefly, male Wistar rats were subjected to 2 hours of transient MCAO, and were treated intravenously with 100 µl of a peptide sample (50 nmol) or vehicle control immediately following reperfusion. At 2, 4, 6, 8, approximately 22, and approximately 30 hours after reperfusion, animals were treated by intraperitoneal administration of a 300 µl bolus of a peptide sample (150 nmol). Animals were sacrificed at 48 hours after reperfusion and coronal brain sections were obtained and stained with tetrazolium chloride (TTC) (Bederson et al., 1986, *Stroke* 17: 1304–1308) for histological evaluation.

RESULTS

The results in FIG. 31 indicate that the volume of the infarct in FHA Ca peptide treated animals was reduced to approximately 25% of the hemisphere compared to the infarct volume in control animals which was approximately 40% of the hemisphere.

Equivalents

Those skilled in the art will recognize or be able to ascertain using no more than routine experimentation many equivalents to the specific embodiments of the invention described herein. Such equivalents are intended to be encompassed within the scope of this invention.

What is claimed is:

1. A pharmaceutical composition for administration to a host for the purpose of increasing the permeability of the blood-brain barrier to a molecule, comprising:
   a) the molecule to be delivered from the blood to the brain;
   b) an antibody to FHA which immunologically binds with brain blood vessel endothelial cells thereby increasing the permeability of the blood-brain barrier to said molecule; and
   c) a pharmaceutically acceptable carrier.

2. A pharmaceutical composition for administration to a host for the purpose of increasing the permeability of the blood-brain barrier to a molecule according to claim 1 wherein said antibody to FHA is immunoreactive with the RGD region of FHA.

3. A pharmaceutical composition for administration to a host for the purpose of increasing the permeability of the blood-brain barrier to a molecule according to claim 1 wherein the pharmaceutically acceptable carrier is a carrier for intravenous administration.

4. An antibody to a peptide which inhibits adhesion between leukocytes and endothelial cells, said peptide being selected from the group consisting of:
   IGALKAGAVEAASPRRARRALRQDFFT-PGSVVVRAQGNVTVGRGDP (SEQ ID NO: 31),
   RQDFFTPGSVVVRAQGNVTVTRGDPM-QGVLAQGDIIMDAKGGTLL (SEQ ID NO: 5),
   RGDPMQGVLAQGDIIMDAKGGTLLLRN-DALTEMGTVTISADSAVL (SEQ IN NO: 6),
   RGDPHQGVLAQGDIIMDAKG (SEQ ID NO: 23),
   ETKEVDG (SEQ ID NO: 7),
   GRTRG (SEQ ID NO: 8),
   GLIQGRSVKVD (SEQ ID NO: 9),
   LGYQAK (SEQ ID NO: 10), and
   LEHSTIESKISQSVLAAKGDKGKPAV-SUKVAKKLFLNGTLRAVND (SEQ ID NO: 11),
   wherein said antibody inhibits adhesion between leukocytes and endothelial cells.

5. An antibody to said peptide according to claim 4 wherein said antibody is a polyclonal antibody.

6. An antibody to said peptide according to claim 4 wherein said antibody is a monoclonal antibody.

7. An antibody to a peptide which inhibits adhesion between bacteria and ciliated respiratory epithelial cells, said peptide selected from the group consisting of:
   AKKLFLNGTLRAVNDNNETMSGRQIDV-VDGRPQITDAVTGEARKD (SEQ ID NO: 12),
   GRPQITDAVTGEARKDESVVSDAAL-VADGGPIVVEAGELVSHAGGIG (SEQ ID NO: 32), and
   IVVEAGELVSHAGGIGNGRNKENGAS-VTVRTTGNLVNKGYISHG (SEQ ID NO: 33),
   wherein said antibody inhibits adhesion between bacteria and ciliated respiratory epithelial cells.

8. An antibody to said peptide according to claim 7 wherein said antibody is a polyclonal antibody.

9. An antibody to said peptide according to claim 7 wherein said antibody is a monoclonal antibody.

10. A therapeutic composition useful for inhibiting the influx of leukocytes into inflamed tissue comprising an antibody to a peptide of FHA selected from the group consisting of a peptide which contains the RGD region, a peptide which binds with leukocytes in a manner competitive with that of coagulation Factor X, and a peptide which binds with leukocytes in a manner competitive with that of complement fragment C3bi, wherein said antibody immunoreacts with blood vessel endothelial cells in such a manner that leukocyte migration from the blood stream into inflamed tissue is inhibited.

11. A therapeutic composition useful for inhibiting the influx of leukocytes into inflamed tissue according to claim 10 wherein the antibody is an antibody to a peptide selected from the group consisting of:
   IGALKAGAVEAASPRRARRALRQDFFT-PGSVVVRAQGNVTVGRGDP (SEQ ID NO: 31),
   RQDFFTPGSVVVRAQGNVTVTRGDPMQGVLAQ-GDIIMDAKGGTLL, (SEQ ID NO:21)
   RGDPMQGVLAQGDIIMDAKGGTLLLRNDALTEM-GTVTISADSAVL, (SEQ ID NO:22)
   LEHSTIESKISQSVLAAKGDKGKPAV-SUKVAKKLFLNGTLRAVND (SEQ ID NO: 11),
   GRTRG (SEQ ID NO: 8),
   ETKEVDG (SEQ ID NO: 7),
   GLIQGRSVKVD (SEQ ID NO: 9), and
   LGYQAK (SEQ ID NO: 10).

12. An antibody to a peptide derivative of FHA where said peptide derivative of FHA is selected from the group consisting of:
   LEHSTIESKISQSVLAAKGDKGKPAV-SUKVAKKLFLNGTLRAVND (SEQ ID NO:11),
   AKKLFLNGTLRAVNDNNETMSGRQIDV-VDGRPQITDAVTGEARKD (SEQ ID NO: 12),
   GRPQITDAVTGEARKDESVVSDAAL-VADGGPIVVEAGELVSHAGGIG (SEQ ID NO: 32),
   IVVEAGELVSHAGGIGNGRNKENGAS-VTVRTTGNLVNKGYISHG (SEQ ID NO: 33),
   PMQGVLAQGDIIMDAKGGTLLLRNDALT (SEQ IN NO: 34), and
   PMQGVLAQGDIIMDAKGGTLLLRN-DALTEMSTVTISADSAVL (SEQ ID NO: 35).

13. A therapeutic composition useful for preventing adherence of *Bordetella pertussis* to ciliated respiratory epithelial cells in mammals comprising an antibody to a peptide selected from the group consisting of:
   LEHSTIESKISQSVLAAKGDKGKPAV-SUKVAKKLFLNGTLRAVND (SEQ ID NO: 11),
   AKKLFLNGTLRAVNDNNETMSGRQIDV-VDGRPQITDAVTGEARKD (SEQ ID NO: 12),
   GRPQITDAVTGEARKDESVVSDAAL-VADGGPIVVEAGELVSHAGGIG (SEQ ID NO: 32),
   IVVEAGELVSHAGGIGNGRNKENGAS-VTVRTTGNLVNKGYISHG (SEQ ID NO: 33),
   PMQGVLAQGDIIMDAKGGTLLLRNDALT (SEQ IN NO: 34), and
   PMQGVLAQGDIIMDAKGGTLLLRN-DALTEMSTVTISADSAVL (SEQ ID NO: 35),
   wherein said antibody immunoreacts with ciliated respiratory epithelial cells such that *Bordetella pertussis* adherence to ciliated respiratory epithelial cells is inhibited.

14. A therapeutic composition of claims 10, 11, or 13 additionally containing a therapeutically effective amount of another therapeutic agent.

* * * * *